(12) United States Patent
Yasuma et al.

(10) Patent No.: US 7,585,880 B2
(45) Date of Patent: Sep. 8, 2009

(54) PHENYLPROPANOIC ACID DERIVATIVES

(75) Inventors: Tsuneo Yasuma, Osaka (JP); Shinobu Sasaki, Osaka (JP); Nozomu Sakai, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 258 days.

(21) Appl. No.: 10/584,730

(22) PCT Filed: Dec. 24, 2004

(86) PCT No.: PCT/JP2004/019749

§ 371 (c)(1),
(2), (4) Date: Jun. 23, 2006

(87) PCT Pub. No.: WO2005/063725

PCT Pub. Date: Jul. 14, 2005

(65) Prior Publication Data

US 2007/0155808 A1    Jul. 5, 2007

(30) Foreign Application Priority Data

Dec. 26, 2003  (JP) .............................. 2003-435089

(51) Int. Cl.
| | |
|---|---|
| A61K 31/443 | (2006.01) |
| A61K 31/4439 | (2006.01) |
| A61K 31/427 | (2006.01) |
| A61K 31/422 | (2006.01) |
| C07D 277/22 | (2006.01) |
| C07D 263/32 | (2006.01) |
| C07D 417/10 | (2006.01) |
| C07D 413/10 | (2006.01) |

(52) U.S. Cl. ..................... 514/340; 514/342; 514/365; 514/374; 546/268.7; 546/269.1; 548/146; 548/215

(58) Field of Classification Search ................. 514/340, 514/342, 365, 374; 546/268.7, 269.1; 548/146, 548/215
See application file for complete search history.

(56) References Cited

FOREIGN PATENT DOCUMENTS

| | | |
|---|---|---|
| EP | 1 559 422 | 8/2005 |
| JP | 7-505647 | 6/1995 |
| WO | 93/21166 | 10/1993 |
| WO | 97/31907 | 9/1997 |
| WO | 99/11255 | 3/1999 |
| WO | 00/64876 | 11/2000 |
| WO | 01/00603 | 1/2001 |
| WO | 01/55085 | 8/2001 |
| WO | 02/053547 | 7/2002 |
| WO | 02/083616 | 10/2002 |
| WO | 02/092590 | 11/2002 |
| WO | WO-02/092590 A1 * | 11/2002 |
| WO | 03/099793 | 12/2003 |
| WO | 2004/022551 | 3/2004 |
| WO | 2004/041266 | 5/2004 |

* cited by examiner

*Primary Examiner*—Rei-Tsang Shiao
*Assistant Examiner*—Janet L Coppins
(74) *Attorney, Agent, or Firm*—Wenderoth, Lind & Ponack, L.L.P.

(57) ABSTRACT

The present invention provides a novel compound having a GPR40 receptor function modulating action, which is useful as an insulin secretagogue, a drug for the prophylaxis or treatment of diabetes and the like.

A compound represented by the formula (I)

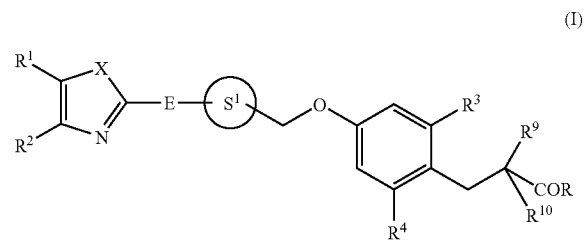

wherein each symbol is as defined in the specification, a salt thereof and a prodrug thereof have unexpectedly superior GPR40 receptor agonist activity and also show superior properties as a pharmaceutical product, such as stability and the like. Thus, they can be safe and useful drugs for the prophylaxis or treatment of GPR40 receptor related conditions or diseases in mammals.

13 Claims, No Drawings

PHENYLPROPANOIC ACID DERIVATIVES

This application is a U.S. national stage of International Application No. PCT/JP2004/019749 filed Dec. 24, 2004.

TECHNICAL FIELD

The present invention relates to a novel compound having GPR40 receptor function modulating action and which is useful as an agent for the treatment of diabetes.

BACKGROUND ART

It has been reported in recent years that a ligand of GPR40, which is one of the G Protein-Coupled Receptors (GPCR), is fatty acid and GPR40 in pancreatic β cell is deeply involved in insulin secretion action (Nature, 2003, vol. 422, pages 173-176). Thus, a GPR40 agonist promotes insulin secretion, a GPR40 antagonist inhibits insulin secretion, and the agonist and the antagonist are useful as an agent for the treatment of type 2 diabetes, obesity, impaired glucose tolerance, insulin resistance, neurodegenerative diseases (Alzheimer's disease) and the like (WO03/068959 and WO02/057783).

On the other hand, many compounds useful as an agent for the treatment of diabetes have been reported.

For example, WO02/092590 discloses that a peroxisome proliferator activated receptor (PPAR) modulator represented by the formula:

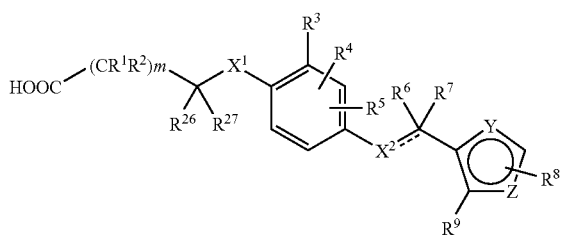

wherein $X^1$: a $C_{1-3}$ alkyl and the like; $R^1$, $R^2$: H and the like; $R^3$, $R^4$, $R^5$: H, $CH_3$ and the like; $R^{26}$, $R^{27}$: H and the like; m: 0-3; $X^2$: O and the like; $R^6$, $R^7$: H and the like; Y, Z: one is CH and the other is S or O; $R^8$: a phenyl and the like; and $R^9$: a $C_{1-6}$ alkyl and the like, is useful as an agent for the prophylaxis or treatment of PPAR mediated disease (e.g., diabetes).

WO02/053547 discloses that an alkanoic acid derivative represented by the formula:

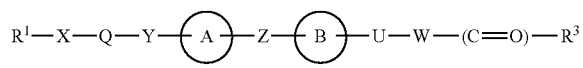

wherein $R^1$: an optionally substituted 5-membered aromatic heterocyclic group; X: a bond, O, S, —$NR^6$— ($R^6$: H, an optionally substituted hydrocarbon group and the like) and the like; Q: a divalent $C_{1-20}$ hydrocarbon group; Y: a bond, O, S, —$NR^7$— ($R^7$: H, an optionally substituted hydrocarbon group and the like) and the like; ring A: an aromatic ring optionally further having 1 to 3 substituents; Z: —$(CH_2)n-Z^1$- (n: 1-8, $Z^1$: O and the like) and the like; ring B: a benzene ring optionally further having 1 to 3 substituents, and the like; U: a bond and the like; W: a divalent $C_{1-20}$ hydrocarbon group; and $R^3$: —$OR^8$— ($R^8$: H, an optionally substituted hydrocarbon group) or —$NR^9R^{10}$— ($R^9$, $R^{10}$: H, an optionally substituted hydrocarbon group and the like) and the like; provided that when ring B is a benzene ring optionally further having 1 to 3 substituents, then U is a bond, is useful as an agent for the prophylaxis or treatment of diabetes, hyperlipidemia, impaired glucose tolerance and the like.

WO99/11255 discloses that a compound represented by the formula:

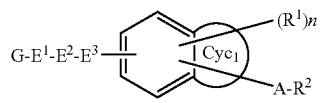

wherein $R^1$: a $C_{1-8}$ alkyl, a $C_{1-8}$ alkoxy, a halogen atom, a trifluoromethyl and the like; $R^2$: —$COOR^3$ ($R^3$: H, a $C_{1-4}$ alkyl) and the like; A: a $C_{1-8}$ alkylene and the like; G: a carbon ring optionally substituted by a $C_{1-8}$ alkyl, a $C_{1-8}$ alkoxy, a halogen atom, a trifluoromethyl or a nitro, and the like; $E^1$: a $C_{1-8}$ alkylene and the like; $E^2$: —O— and the like; $E^3$: a single bond and the like; n: 0, 1; and $Cyc_1$ ring: absent and the like, has a PPAR receptor regulating action, and is useful as an agent for the prophylaxis or treatment of metabolism abnormality diseases such as diabetes, obesity, syndrome X, hypercholesterolemia, hyperlipoproteinemia and the like, and the like.

WO00/64876 discloses that a compound represented by the formula:

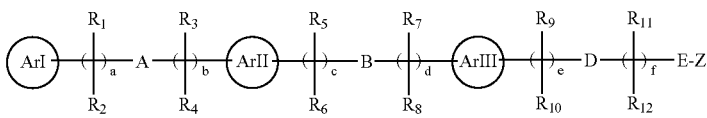

wherein ring ArI, ring ARII, ring ArIII: an optionally substituted condensed ring and the like; A: —O—, —S—, a bond, —$NR_{13}$— ($R_{13}$: H, an alkyl and the like) and the like; B: —O— and the like; D: a bond, an ethylene; E: a bond, an ethylene; Z: $R_{21}O_2C$—, $(R_{21})_2NCO$— ($R_{21}$: H, an alkyl and the like) and the like; a, b, c, e: 0-4; d: 0-5; f: 0-6; and $R_1$-$R_{12}$: H and the like, is useful as a PPAR ligand receptor binder, PPAR receptor agonist or PPAR receptor antagonist, and can be used as an agent for the treatment of diabetes.

WO01/00603 discloses that a compound represented by the formula:

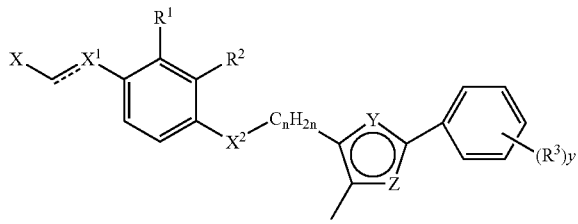

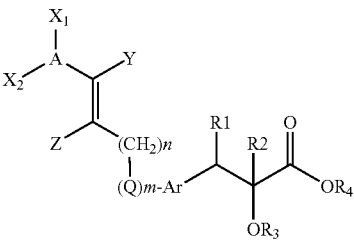

wherein X: COOH (containing ester) and the like; $X^1$: $CH_2$ and the like; dotted line shows double bond only when $X^1$ is CH; $X^2$: O and the like; $R^1$, $R^2$: H, Me and the like; n: 1, 2; Y, Z: one is N and the other is S or O; y: an integer of 0-5; and $R^3$: $CF_3$ and the like, can be used as a PPARδ agonist, and is useful as an agent for the prophylaxis or treatment of PPARδ mediated disease (e.g., hyperlipidemia, arteriosclerosis, type I or II diabetes and the like).

WO97/31907 discloses that a compound represented by the formula:

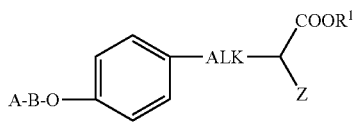

wherein A: a 5- to 6-membered heterocycle containing at least one heteroatom selected from O, N and S, and the like; B: a $C_{1-6}$ alkylene and the like; ALK: a $C_{1-3}$ alkylene; $R^1$: H, a $C_{1-3}$ alkyl; and Z: —($C_{1-3}$ alkylene)phenyl optionally substituted by a halogen and the like, is useful as a PPARγ agonist, and can be used as an agent for the prophylaxis or treatment of hyperglycemia, type I or II diabetes, hyperlipidemia and the like.

WO02/083616 discloses that a compound represented by the formula:

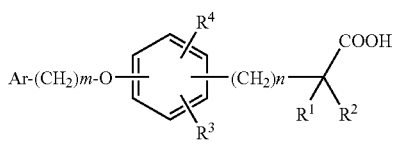

wherein Ar: a phenyl substituted by 1 to 5 the same or different halogen atoms and the like, and the like; $R^1$: a halogen atom and the like; $R^2$: H and the like; $R^3$, $R^4$: H, a halogen atom; m: 1, 2; and n: 2-7, has a superior insulin sensitizing action, hypoglycemic action, hypolipidemic action, antiinflammatory action, immunomodulating action, lipoperoxide production suppressive action and PPAR activating action, and is useful as an agent for the treatment of diabetes.

WO01/55085 discloses that a compound represented by the formula:

wherein A: an aryl optionally substituted by OH and the like; $X^1$, $X^2$: H and the like; Y, Z: H and the like; n: 0-3; m: 0, 1; Q: O and the like; Ar: an arylene and the like; and $R_1$-$R_4$: H and the like, is useful as an agent for the treatment of PPAR related diseases, and useful as an agent for the treatment of, for example, type 2 diabetes, impaired glucose tolerance, insulin resistance, hypertriglyceridemia and the like.

However, it has not been disclosed at all that these known therapeutic drugs for diabetes have a GPR40 receptor function modulating action, and there is no report on a compound having a GPR40 receptor function modulating action (compound useful as a GPR40 agonist or GPR40 antagonist). Under the circumstances, development of a compound having a GPR40 receptor function modulating action has been desired.

DISCLOSURE OF THE INVENTION

The present invention aims at providing a novel compound having a GPR40 receptor function modulating action, which is useful as an insulin secretagogue or an agent for the prophylaxis or treatment of diabetes and the like.

The present inventors have intensively conducted various studies and found that the compound represented by the following formula (I) unexpectedly has a superior GPR40 receptor agonist activity, shows superior properties as a pharmaceutical product such as stability and the like, and can be a safe and useful pharmaceutical agent for the prophylaxis or treatment of GPR40 receptor related disease state or diseases in mammal, and completed the present invention.

Accordingly, the present invention relates to the following.

(1) A compound represented by the formula (I)

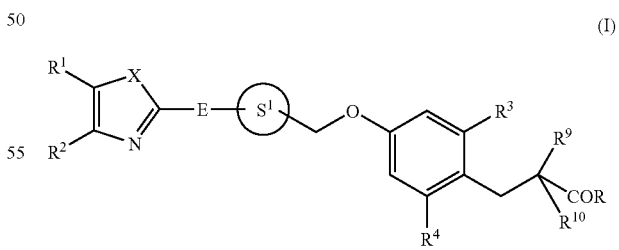

wherein X is S or O, $R^1$ and $R^2$ are the same or different and each is a hydrogen atom, an optionally substituted $C_{6-14}$ aryl group, an optionally substituted heterocyclic group or an optionally substituted $C_{1-6}$ alkyl group, or $R^1$ and $R^2$ are bonded to each other to form a ring together with the carbon atom they are bonded to, E is $-W^1-N(R^5)-W^2-$, $-W^1-CH(R^6)-O-W^2-$, $-W^1-O-CH(R^6)-W^2-$, $-W^1-S(O)n-W^2-$ or $-W^1-CH(R^6)-W^2-$ ($W^1$ and $W^2$ are the same or different and each is a bond or an optionally substituted $C_{1-3}$ alkylene group, $R^5$ and $R^6$ are each an optionally substituted heterocyclic group or an optionally substituted hydrocarbon group, and n is 1 or 2, provided that when X is S, then $R^5$ and $R^6$ are not $C_{1-6}$ alkyl groups), ring $S^1$ is a benzene ring or a pyridine ring each optionally further having substituent(s) selected from an optionally substituted $C_{1-6}$ alkyl group, an optionally substituted $C_{1-6}$ alkoxy group and a halogen atom, $R^3$ and $R^4$ are the same or different and each is a hydrogen atom, a halogen atom, an optionally substituted $C_{1-6}$ alkyl group or an optionally substituted $C_{1-6}$ alkoxy group, $R^9$ and $R^{10}$ are the same or different and each is a hydrogen atom, a halogen atom or a $C_{1-6}$ alkoxy group, and R is an optionally substituted hydroxy group or an optionally substituted amino group, or a salt thereof.

(2) The compound of the above-mentioned (1), wherein E is $-W^1-N(R^5)-W^2-$, $-W^1-CH(R^6)-O-W^2-$, $-W^1-O-CH(R^6)-W^2-$ or $-W^1-CH(R^6)-W^2-$ ($W^1$ and $W^2$ are the same or different and each is a bond or an optionally substituted $C_{1-3}$ alkylene group, and $R^5$ and $R^6$ are each an optionally substituted heterocyclic group or an optionally substituted hydrocarbon group, provided that when X is S, then $R^5$ and $R^6$ are not $C_{1-6}$ alkyl groups), ring $S^1$ is a benzene ring optionally further having substituent(s) selected from an optionally substituted $C_{1-6}$ alkyl group, an optionally substituted $C_{1-6}$ alkoxy group and a halogen atom, and $R^9$ and $R^{10}$ are hydrogen atoms, or a salt thereof.

(3) A prodrug of a compound of the above-mentioned (1) or a salt thereof.

(4) The compound of the above-mentioned (1), wherein $R^3$ and $R^4$ are the same or different and each is a hydrogen atom or a halogen atom, or a salt thereof.

(5) The compound of the above-mentioned (1), wherein E is $-W^1-N(R^5)-W^2-$ ($W^1$ and $W^2$ are the same or different and each is a bond or an optionally substituted $C_{1-3}$ alkylene group, and $R^5$ is an optionally substituted heterocyclic group or an optionally substituted hydrocarbon group, provided that when X is S, then $R^5$ is not a $C_{1-6}$ alkyl group), or a salt thereof.

(6) The compound of the above-mentioned (5), wherein $R^5$ is an optionally substituted $C_{7-16}$ aralkyl group, or a salt thereof.

(7) The compound of the above-mentioned (1), wherein R is a hydroxy group, or a salt thereof.

(8) The compound of the above-mentioned (1), wherein X is S, or a salt thereof.

(9) The compound of the above-mentioned (1), wherein ring $S^1$ is a benzene ring, or a salt thereof.

(10) The compound of the above-mentioned (1), wherein both $R^9$ and $R^{10}$ are hydrogen atoms, or a salt thereof.

(11) 3-[4-[[4-[[(2-Phenylethyl)(4-phenyl-1,3-thiazol-2-yl)amino]methyl]benzyl]oxy]phenyl]propanoic acid, 3-[2,6-difluoro-4-[[4-[[(2-phenylethyl)(4-phenyl-1,3-thiazol-2-yl)amino]methyl]benzyl]oxy]phenyl]propanoic acid, 2-fluoro-3-{4-[(4-{[(2-phenylethyl)(4-phenyl-1,3-thiazol-2-yl)amino]methyl}benzyl)oxy]phenyl}propanoic acid, 3-{2-fluoro-4-[(4-(1-[(4-phenyl-1,3-thiazol-2-yl)sulfonyl]butyl}benzyl)oxy]phenyl)propanoic acid, or a salt thereof.

(12) A GPR40 receptor function modulator comprising a compound of the above-mentioned (1) or a salt thereof or a prodrug thereof.

(13) A pharmaceutical agent comprising a compound of the above-mentioned (1) or a salt thereof or a prodrug thereof.

(14) The pharmaceutical agent of the above-mentioned (13), which is an agent for the prophylaxis or treatment of diabetes.

(15) Use of a compound of the above-mentioned (1) or a salt thereof or a prodrug thereof for the production of a GPR40 receptor function modulator.

(16) Use of a compound of the above-mentioned (1) or a salt thereof or a prodrug thereof for the production of an agent for the prophylaxis or treatment of diabetes.

(17) A method of modulating GPR40 receptor function in a mammal, which comprises administering an effective amount of a compound of the above-mentioned (1) or a salt thereof or a prodrug thereof to the mammal.

(18) A method for the prophylaxis or treatment of diabetes in a mammal, which comprises administering an effective amount of a compound of the above-mentioned (1) or a salt thereof or a prodrug thereof to the mammal, and the like.

The compound, a salt thereof and a prodrug thereof of the present invention have a superior GPR40 receptor function modulating action, and can be used as agents for the prophylaxis or treatment of diabetes and the like.

DETAILED DESCRIPTION OF THE INVENTION

Best Mode for Carrying Out the Invention

Unless otherwise specified, as the "halogen atom" in the present specification, a fluorine atom, a chlorine atom, a bromine atom and an iodine atom can be mentioned.

Unless otherwise specified, as the "optionally substituted hydrocarbon group" in the present specification, for example, "an optionally substituted $C_{1-6}$ alkyl group", "an optionally substituted $C_{2-6}$ alkenyl group", "an optionally substituted $C_{2-6}$ alkynyl group", "an optionally substituted $C_{3-8}$ cycloalkyl group", "an optionally substituted $C_{6-14}$ aryl group", "an optionally substituted $C_{7-16}$ aralkyl group" and the like can be mentioned.

Unless otherwise specified, as the "$C_{1-6}$ alkyl group" in the present specification, for example, methyl, ethyl, propyl, isopropyl, butyl, isobutyl, sec-butyl, tert-butyl, pentyl, isopentyl, neopentyl, hexyl and the like can be mentioned.

Unless otherwise specified, as the "$C_{2-6}$ alkenyl group" in the present specification, for example, vinyl, propenyl, isopropenyl, 2-buten-1-yl, 4-penten-1-yl, 5-hexen-1-yl and the like can be mentioned.

Unless otherwise specified, as the "$C_{2-6}$ alkynyl group" in the present specification, for example, 2-butyn-1-yl, 4-pentyn-1-yl, 5-hexyn-1-yl and the like can be mentioned.

Unless otherwise specified, as the "$C_{3-8}$ cycloalkyl group" in the present specification, for example, cyclopropyl, cyclobutyl, cyclopentyl, cyclohexyl and the like can be mentioned.

Unless otherwise specified, as the "$C_{6-14}$ aryl group" in the present specification, for example, phenyl, 1-naphthyl, 2-naphthyl, 2-biphenylyl, 3-biphenylyl, 4-biphenylyl, 2-anthryl and the like can be mentioned. The $C_{6-14}$ aryl is optionally saturated partially, and as the partially saturated $C_{6-14}$ aryl, for example, tetrahydronaphthyl and the like can be mentioned.

Unless otherwise specified, as the "$C_{7-16}$ aralkyl group" in the present specification, for example, benzyl, phenethyl, diphenylmethyl, 1-naphthylmethyl, 2-naphthylmethyl, 2,2- diphenylethyl, 3-phenylpropyl, 4-phenylbutyl, 5-phenylpentyl, 2-biphenylylmethyl, 3-biphenylylmethyl, 4-biphenylylmethyl and the like can be mentioned.

Unless otherwise specified, as the "optionally substituted hydroxy group" in the present specification, for example, "a hydroxy group", "an optionally substituted $C_{1-10}$ alkoxy group (including an optionally substituted $C_{1-6}$ alkoxy group)", "an optionally substituted heterocyclyloxy group", "an optionally substituted $C_{6-14}$ aryloxy group", "an optionally substituted $C_{7-16}$ aralkyloxy group" and the like can be mentioned.

Unless otherwise specified, as the "$C_{1-6}$ alkoxy group" in the present specification, for example, methoxy, ethoxy, propoxy, isopropoxy, butoxy, isobutoxy, tert-butoxy, pentyloxy, hexyloxy and the like can be mentioned. As the "$C_{1-10}$ alkoxy group" in the present specification, heptyloxy, octyloxy, nonyloxy, decyloxy and the like can be mentioned besides the above-mentioned $C_{1-6}$ alkoxy group.

As the "heterocyclyloxy group" in the present specification, a hydroxy group substituted by a "heterocyclic group" below can be mentioned. As preferable examples of the heterocyclyloxy group, tetrahydropyranyloxy, thiazolyloxy, pyridyloxy, pyrazolyloxy, oxazolyloxy, thienyloxy, furyloxy and the like can be mentioned.

Unless otherwise specified, as the "$C_{6-14}$ aryloxy group" in the present specification, for example, phenoxy, 1-naphthyloxy, 2-naphthyloxy and the like can be mentioned.

Unless otherwise specified, as the "$C_{7-16}$ aralkyloxy group" in the present specification, for example, benzyloxy, phenethyloxy and the like can be mentioned.

Unless otherwise specified, as the "$C_{1-6}$ alkylthio group" in the present specification, for example, methylthio, ethylthio, propylthio, isopropylthio, butylthio, sec-butylthio, tert-butylthio, hexylthio and the like can be mentioned.

Unless otherwise specified, as the "heterocyclic group" in the present specification, for example, a 5- to 14-membered (monocyclic, bicyclic or tricyclic) heterocyclic group containing, as a ring-constituting atom besides carbon atom(s), 1 or 2 kinds of and 1 to 4 atoms of heteroatoms selected from a nitrogen atom, a sulfur atom and an oxygen atom, preferably (i) a 5- to 14-membered (preferably 5- to 10-membered) aromatic heterocyclic group, (ii) a 5- to 10-membered non-aromatic heterocyclic group and the like can be mentioned. Of these, a 5- or 6-membered aromatic heterocyclic group is preferable.

Specifically, an aromatic heterocyclic group such as thienyl (e.g., 2-thienyl, 3-thienyl etc.), furyl (e.g., 2-furyl, 3-furyl etc.), pyridyl (e.g., 2-pyridyl, 3-pyridyl, 4-pyridyl etc.), thiazolyl (e.g., 2-thiazolyl, 4-thiazolyl, 5-thiazolyl etc.), oxazolyl (e.g., 2-oxazolyl, 4-oxazolyl, 5-oxazolyl etc.), quinolyl (e.g., 2-quinolyl, 3-quinolyl, 4-quinolyl, 5-quinolyl, 8-quinolyl etc.), isoquinolyl (e.g., 1-isoquinolyl, 3-isoquinolyl, 4-isoquinolyl, 5-isoquinolyl etc.), pyrazinyl, pyrimidinyl (e.g., 2-pyrimidinyl, 4-pyrimidinyl etc.), pyrrolyl (e.g., 1-pyrrolyl, 2-pyrrolyl, 3-pyrrolyl etc.), imidazolyl (e.g., 1-imidazolyl, 2-imidazolyl, 4-imidazolyl etc.), pyrazolyl (e.g., 1-pyrazolyl, 3-pyrazolyl, 4-pyrazolyl etc.), pyridazinyl (e.g., 3-pyridazinyl, 4-pyridazinyl etc.), isothiazolyl (e.g., 3-isothiazolyl, 4-isothiazolyl, 5-isothiazolyl etc.), isoxazolyl (e.g., 3-isoxazolyl, 4-isoxazolyl, 5-isoxazolyl etc.), indolyl (e.g., 1-indolyl, 2-indolyl, 3-indolyl etc.), 2-benzothiazolyl, 2-benzoxazolyl, benzimidazolyl (e.g., 1-benzimidazolyl, 2-benzimidazolyl etc.), benzo[b]thienyl (e.g., 2-benzo[b]thienyl, 3-benzo[b]thienyl etc.), benzo[b]furanyl (e.g., 2-benzo[b]furanyl, 3-benzo[b]furanyl etc.) and the like;

a non-aromatic heterocyclic group such as pyrrolidinyl (e.g., 1-pyrrolidinyl, 2-pyrrolidinyl, 3-pyrrolidinyl etc.), oxazolidinyl (e.g., 2-oxazolidinyl etc.), imidazolinyl (e.g., 1-imidazolinyl, 2-imidazolinyl, 4-imidazolinyl etc.), piperidinyl (e.g., 1-piperidinyl, 2-piperidinyl, 3-piperidinyl, 4-piperidinyl etc.), piperazinyl (e.g., 1-piperazinyl, 2-piperazinyl etc.), morpholinyl (e.g., 2-morpholinyl, 3-morpholinyl, 4-morpholinyl etc.), thiomorpholinyl (e.g., 2-thiomorpholinyl, 3-thiomorpholinyl, 4-thiomorpholinyl etc.), tetrahydropyranyl, oxodioxolyl (e.g., 2-oxo-1,3-dioxol-4-yl etc.) and the like, and the like can be mentioned.

Unless otherwise specified, as the "$C_{1-6}$ alkylsulfonyl group" in the present specification, for example, methylsulfonyl, ethylsulfonyl, propylsulfonyl, isopropylsulfonyl, hexylsulfonyl and the like can be mentioned.

Unless otherwise specified, as the "$C_{1-6}$ alkylsulfinyl group" in the present specification, for example, methylsulfinyl, ethylsulfinyl, propylsulfinyl, isopropylsulfinyl, hexylsulfinyl and the like can be mentioned.

Unless otherwise specified, as the "$C_{6-14}$ arylsulfonyl group" in the present specification, for example, phenylsulfonyl, 1-naphthylsulfonyl, 2-naphthylsulfonyl and the like can be mentioned.

Unless otherwise specified, as the "$C_{6-14}$ arylsulfinyl group" in the present specification, for example, phenylsulfinyl, 1-naphthylsulfinyl, 2-naphthylsulfinyl and the like can be mentioned.

Unless otherwise specified, as the "optionally esterified carboxyl group" in the present specification, for example, carboxyl, a $C_{1-6}$ alkoxy-carbonyl group (e.g., methoxycarbonyl, ethoxycarbonyl, propoxycarbonyl, tert-butoxycarbonyl etc.), a $C_{6-14}$ aryloxy-carbonyl group (e.g., phenoxycarbonyl etc.), a $C_{7-16}$ aralkyloxy-carbonyl group (e.g., benzyloxycarbonyl, phenethyloxycarbonyl etc.) and the like can be mentioned.

Unless otherwise specified, as the "optionally halogenated $C_{1-6}$ alkyl group" in the present specification, the above-mentioned "$C_{1-6}$ alkyl group" optionally substituted by 1 to 5 of the above-mentioned "halogen atoms" can be mentioned. For example, methyl, ethyl, propyl, isopropyl, butyl, tert-butyl, isobutyl, trifluoromethyl and the like can be mentioned.

Unless otherwise specified, as the "optionally halogenated $C_{1-6}$ alkoxy group" in the present specification, the above-mentioned "$C_{1-6}$ alkoxy group" optionally substituted by 1 to 5 of the above-mentioned "halogen atoms" can be mentioned. For example, methoxy, ethoxy, isopropoxy, tert-butoxy, trifluoromethoxy and the like can be mentioned.

Unless otherwise specified, as the "mono- or di-$C_{1-6}$ alkyl-amino group" in the present specification, an amino group mono- or di-substituted by the above-mentioned "$C_{1-6}$ alkyl group" can be mentioned. For example, methylamino, ethylamino, propylamino, dimethylamino, ethylmethylamino, diethylamino and the like can be mentioned.

Unless otherwise specified, as the "mono- or di-$C_{6-14}$ aryl-amino group" in the present specification, an amino group mono- or di-substituted by the above-mentioned "$C_{6-14}$ aryl group" can be mentioned. For example, phenylamino, diphenylamino, 1-naphthylamino, 2-naphthylamino, naphthylphenylamino and the like can be mentioned.

Unless otherwise specified, as the "mono- or di-$C_{7-16}$ aralkyl-amino group" in the present specification, an amino group mono- or di-substituted by the above-mentioned "$C_{7-16}$ aralkyl group" can be mentioned. For example, benzylamino, phenethylamino and the like can be mentioned.

Unless otherwise specified, as the "N—$C_{1-6}$ alkyl-N—$C_{6-14}$ aryl-amino group" in the present specification, an amino group substituted by the above-mentioned "$C_{1-6}$ alkyl group" and the above-mentioned "$C_{6-14}$ aryl group" can be mentioned. For example, N-methyl-N-phenylamino, N-ethyl-N-phenylamino and the like can be mentioned.

Unless otherwise specified, as the "N—$C_{1-6}$ alkyl-N—$C_{7-16}$ aralkyl-amino group" in the present specification, an amino group substituted by the above-mentioned "$C_{1-6}$ alkyl group" and the above-mentioned "$C_{7-16}$ aralkyl group" can be mentioned. For example, N-methyl-N-benzylamino, N-ethyl-N-benzylamino and the like can be mentioned.

Unless otherwise specified, as the "mono- or di-$C_{1-6}$ alkyl-carbamoyl group" in the present specification, a carbamoyl group mono- or di-substituted by the above-mentioned "$C_{1-6}$ alkyl group" can be mentioned. For example, methylcarbamoyl, ethylcarbamoyl, isopropylcarbamoyl, hexylcarbamoyl, dimethylcarbamoyl, diethylcarbamoyl, ethylmethylcarbamoyl and the like can be mentioned.

Unless otherwise specified, as the "mono- or di-$C_{6-14}$ aryl-carbamoyl group" in the present specification, a carbamoyl group mono- or di-substituted by the above-mentioned "$C_{6-14}$ aryl group" can be mentioned. For example, phenylcarbamoyl, 1-naphthylcarbamoyl, 2-naphthylcarbamoyl and the like can be mentioned.

Unless otherwise specified, as the "mono- or di-5- to 7-membered heterocyclyl-carbamoyl group" in the present specification, a carbamoyl group mono- or di-substituted by a 5- to 7-membered heterocyclic group can be mentioned. As the 5- to 7-membered heterocyclic group, a heterocyclic group containing, as a ring-constituting atom besides carbon atom(s), 1 or 2 kinds of and 1 to 4 atoms of heteroatoms selected from a nitrogen atom, a sulfur atom and an oxygen atom can be mentioned. As the heterocyclic group, for example, thienyl, furyl, pyridyl, thiazolyl, oxazolyl, pyrazinyl, pyrimidinyl, pyrrolyl, imidazolyl, pyrazolyl, pyridazinyl, isothiazolyl, isoxazolyl and the like can be mentioned.

As preferable examples of the "mono- or di-5 to 7-membered heterocyclyl-carbamoyl group", 2-pyridylcarbamoyl, 3-pyridylcarbamoyl, 4-pyridylcarbamoyl, 2-thienylcarbamoyl, 3-thienylcarbamoyl and the like can be mentioned.

Unless otherwise specified, as the "mono- or di-$C_{6-14}$ arylsulfamoyl group" in the present specification, a sulfamoyl group mono- or di-substituted by the above-mentioned "$C_{1-6}$ alkyl group" can be used and, for example, methylsulfamoyl, ethylsulfamoyl, propylsulfamoyl, isopropylsulfamoyl, hexylsulfamoyl, dimethylsulfamoyl, diethylsulfamoyl, ethylmethylsulfamoyl and the like can be mentioned.

Unless otherwise specified, as the "mono- or di-$C_{6-14}$ arylsulfamoyl group" in the present specification, a sulfamoyl group mono- or di-substituted by the above-mentioned "$C_{6-14}$ aryl group" can be used and, for example, phenylsulfamoyl, diphenylsulfamoyl, 1-naphthylsulfamoyl, 2-naphthylsulfamoyl and the like can be mentioned.

As the "optionally substituted $C_{1-6}$ alkyl group", "optionally substituted $C_{2-6}$ alkenyl group", "optionally substituted $C_{2-6}$ alkynyl group" and "optionally substituted $C_{1-10}$ alkoxy group (containing an optionally substituted $C_{1-6}$ alkoxy group)" in the present specification, for example, "a $C_{1-6}$ alkyl group", "a $C_{2-6}$ alkenyl group", "a $C_{2-6}$ alkynyl group" and "a $C_{1-10}$ alkoxy group (containing a $C_{1-6}$ alkoxy group)", each of which optionally has, at substitutable position(s), 1 to 5 substituents selected from (1) a halogen atom;
(2) a hydroxy group;
(3) an amino group;
(4) a nitro group;
(5) a cyano group;
(6) a heterocyclic group (preferably furyl, pyridyl, thienyl, pyrazolyl, thiazolyl, oxazolyl, 2-oxo-1,3-dioxol-4-yl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(7) a mono- or di-$C_{1-6}$ alkyl-amino group;
(8) a mono- or di-$C_{6-14}$ aryl-amino group;
(9) a mono- or di-$C_{7-16}$ aralkyl-amino group;
(10) a N—$C_{1-6}$ alkyl-N—$C_{6-14}$ aryl-amino group;
(11) a N—$C_{1-6}$ alkyl-N—$C_{7-16}$ aralkyl-amino group;
(12) a $C_{3-8}$ cycloalkyl group;
(13) an optionally halogenated $C_{1-6}$ alkoxy group;
(14) a $C_{1-6}$ alkylthio group;
(15) a $C_{1-6}$ alkylsulfinyl group;
(16) a $C_{1-6}$ alkylsulfonyl group;
(17) an optionally esterified carboxyl group;
(18) a carbamoyl group;
(19) a thiocarbamoyl group;
(20) a mono- or di-$C_{1-6}$ alkyl-carbamoyl group;
(21) a mono- or di-$C_{6-14}$ aryl-carbamoyl group;
(22) a mono- or di-5- to 7-membered heterocyclyl-carbamoyl group;
(23) a $C_{1-6}$ alkyl-carbonylamino group (e.g., acetylamino, propionylamino etc.) optionally substituted by a carboxyl group;
(24) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, mono- or di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(25) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or a di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(26) a heterocyclyloxy group;
(27) a sulfamoyl group;
(28) a mono- or di-$C_{1-6}$ alkyl-sulfamoyl group;
(29) a mono- or di-$C_{6-14}$ aryl-sulfamoyl group;
(30) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group; and the like, can be mentioned.

As the "optionally substituted $C_{3-8}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group" and "optionally substituted $C_{7-16}$ aralkyloxy group" in the present specification, for example, "a $C_{3-8}$ cycloalkyl group", "a $C_{6-14}$ aryl group", "a $C_{7-16}$ aralkyl group", "a heterocyclic group", "a heterocyclyloxy group", "a $C_{6-14}$ aryloxy group" and "a $C_{7-16}$ aralkyloxy group", each of which optionally has, at substitutable position(s), 1 to 5 substituents selected from (1) a halogen atom;
(2) a hydroxy group;
(3) an amino group;
(4) a nitro group;
(5) a cyano group;
(6) an optionally substituted $C_{1-6}$ alkyl group;
(7) an optionally substituted $C_{2-6}$ alkenyl group;
(8) an optionally substituted $C_{2-6}$ alkynyl group;
(9) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(10) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(11) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(12) a heterocyclic group (preferably furyl, pyridyl, thienyl, pyrazolyl, thiazolyl, oxazolyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkylthio group, a $C_{1-6}$ alkylsulfinyl group, a $C_{1-6}$ alkylsulfonyl group, optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(13) a mono- or di-$C_{1-6}$ alkyl-amino group;
(14) a mono- or di-$C_{6-14}$ aryl-amino group;
(15) a mono- or di-$C_{7-16}$ aralkyl-amino group;
(16) a N—$C_{1-6}$ alkyl-N—$C_{6-14}$ aryl-amino group;
(17) a N—$C_{1-6}$ alkyl-N—$C_{7-16}$ aralkyl-amino group;
(18) a $C_{3-8}$ cycloalkyl group;
(19) an optionally substituted $C_{1-6}$ alkoxy group;
(20) a $C_{1-6}$ alkylthio group;
(21) a $C_{1-6}$ alkylsulfinyl group;
(22) a $C_{1-6}$ alkylsulfonyl group;
(23) an optionally esterified carboxyl group;
(24) a carbamoyl group;
(25) a thiocarbamoyl group;
(26) a mono- or di-$C_{1-6}$ alkyl-carbamoyl group;
(27) a mono- or di-$C_{6-14}$ aryl-carbamoyl group;
(28) a mono- or di-5- to 7-membered heterocyclyl-carbamoyl group;
(29) a sulfamoyl group;
(30) a mono- or di-$C_{1-6}$ alkyl-sulfamoyl group;
(31) a mono- or di-$C_{6-14}$ aryl-sulfamoyl group; and the like, can be mentioned.

Unless otherwise specified, as the "optionally substituted amino group" in the present specification, an amino group optionally substituted by 1 or 2 substituents selected from (1) an optionally substituted $C_{1-6}$ alkyl group;
(2) an optionally substituted $C_{2-6}$ alkenyl group;
(3) an optionally substituted $C_{2-6}$ alkynyl group;
(4) an optionally substituted $C_{3-8}$ cycloalkyl group;
(5) an optionally substituted $C_{6-14}$ aryl group;
(6) an optionally substituted $C_{1-6}$ alkoxy group;
(7) an optionally substituted acyl group;
(8) an optionally substituted heterocyclic group (preferably furyl, pyridyl, thienyl, pyrazolyl, thiazolyl, oxazolyl);
(9) a sulfamoyl group;
(10) a mono- or di-$C_{1-6}$ alkyl-sulfamoyl group;
(11) a mono- or di-$C_{6-14}$ aryl-sulfamoyl group; and the like, can be mentioned. When the "optionally substituted amino group" is an amino group substituted by two substituents, these substituents may form a nitrogen-containing heterocycle together with the adjacent nitrogen atom. As the "nitrogen-containing heterocycle", for example, a 5- to 7-membered nitrogen-containing heterocycle containing at least one nitrogen atom and optionally further containing, as a ring-constituting atom besides carbon atom(s), 1 or 2 heteroatoms selected from an oxygen atom, a sulfur atom and a nitrogen atom can be mentioned. As preferable examples of the nitrogen-containing heterocycle, pyrrolidine, imidazolidine, pyrazolidine, piperidine, piperazine, morpholine, thiomorpholine, thiazolidine, oxazolidine and the like can be mentioned.

Unless otherwise specified, as the "optionally substituted acyl group" in the present specification, groups represented by the formulas: —$COR^7$, —$CO$—$OR^7$, —$SO_2R^7$, —$SOR^7$, —$PO(OR^7)(OR^8)$, —$CO$—$NR^{7a}R^{8a}$ and —$CS$—$NR^{7a}R^{8a}$, wherein $R^7$ and $R^8$ are the same or different and each is a hydrogen atom, an optionally substituted hydrocarbon group or an optionally substituted heterocyclic group, and $R^{7a}$ and $R^{8a}$ are the same or different and each is a hydrogen atom, an optionally substituted hydrocarbon group or an optionally substituted heterocyclic group, or $R^{7a}$ and $R^{8a}$ may form an optionally substituted nitrogen-containing heterocycle together with the adjacent nitrogen atom, and the like can be mentioned.

As the "nitrogen-containing heterocycle" of the "optionally substituted nitrogen-containing heterocycle" formed by $R^{7a}$ and $R^{8a}$ together with the adjacent nitrogen atom, for example, a 5- to 7-membered nitrogen-containing heterocycle containing at least one nitrogen atom and optionally further containing, as a ring-constituting atom besides carbon atom(s), 1 or 2 heteroatoms selected from an oxygen atom, a sulfur atom and a nitrogen atom can be mentioned. As preferable examples of the "nitrogen-containing heterocycle", pyrrolidine, imidazolidine, pyrazolidine, piperidine, piperazine, morpholine, thiomorpholine, thiazolidine, oxazolidine and the like can be mentioned.

The nitrogen-containing heterocycle optionally has 1 or 2 substituents at substitutable position(s). As these substituents, a hydroxy group, an optionally halogenated $C_{1-6}$ alkyl group, a $C_{6-14}$ aryl group, a $C_{7-16}$ aralkyl group and the like can be mentioned.

As preferable examples of the "optionally substituted acyl group", a formyl group, a carboxyl group, a carbamoyl group, a $C_{1-6}$ alkyl-carbonyl group (e.g., acetyl, isobutanoyl, isopentanoyl etc.), a $C_{1-6}$ alkoxy-carbonyl group (e.g., methoxycarbonyl, ethoxycarbonyl, propoxycarbonyl, tert-butoxycarbonyl etc.), a $C_{3-8}$ cycloalkyl-carbonyl group (e.g., cyclopentylcarbonyl, cyclohexylcarbonyl etc.), a $C_{6-14}$ arylcarbonyl group (e.g., benzoyl, 1-naphthoyl, 2-naphthoyl etc.), a $C_{7-16}$ aralkyl-carbonyl group (e.g., phenylacetyl, 2-phenylpropanoyl etc.), a $C_{6-14}$ aryloxy-carbonyl group (e.g., phenyloxycarbonyl, naphthyloxycarbonyl etc.), a $C_{7-16}$ aralkyloxy-carbonyl group (e.g., benzyloxycarbonyl, phenethyloxycarbonyl etc.), a mono- or di-$C_{1-6}$ alkylcarbamoyl group, a mono- or di-$C_{6-14}$ aryl-carbamoyl group, a $C_{3-8}$ cycloalkyl-carbamoyl group (e.g., cyclopropylcarbamoyl etc.), a $C_{7-16}$ aralkyl-carbamoyl group (e.g., benzylcarbamoyl etc.), a $C_{1-6}$ alkylsulfonyl group, a $C_{6-14}$ arylsulfonyl group, a nitrogen-containing heterocyclyl-carbonyl group (e.g., pyrrolidinylcarbonyl, piperidinylcarbonyl etc.), a $C_{1-6}$ alkylsulfinyl group, a $C_{6-14}$ arylsulfinyl group, a thiocarbamoyl group, a sulfamoyl group, a mono- or di-$C_{1-6}$ alkylsulfamoyl group, a mono- or di-$C_{6-14}$ aryl-sulfamoyl group, a mono- or di-$C_{7-16}$ aralkyl-sulfamoyl group (e.g., benzylsulfamoyl etc.) and the like can be mentioned.

The "$C_{1-3}$ alkylene group" of the "optionally substituted $C_{1-3}$ alkylene group" in the present specification is a straight-chain or a branched-chain, and, for example, methylene, ethylene, 1-methylethylene, propylene and the like can be mentioned. The $C_{1-3}$ alkylene group optionally has 1 to 3 substituents at substitutable position(s). As these substituents, for example, a halogen atom, a hydroxy group, an amino group, a mono- or di-$C_{1-6}$ alkyl-amino group, a mono- or di-$C_{6-14}$ aryl-amino group, a mono- or di-$C_{7-16}$ aralkyl-amino group, a nitro group, a cyano group, a $C_{1-6}$ alkoxy group, a $C_{1-6}$ alkylthio group, a $C_{1-6}$ alkyl group and the like can be mentioned.

As the "ring" to be formed by $R^1$ and $R^2$, bonded to each other, together with the carbon atom they are bonded to, for example, a 5- to 8-membered ring optionally containing, as a ring-constituting atom besides carbon atom(s), 1 or 2 heteroatoms selected from a nitrogen atom, a sulfur atom and an oxygen atom can be mentioned. Preferable examples of such ring include a 5- to 8-membered hydrocarbon ring such as benzene, dihydrobenzene, tetrahydrobenzene and the like; a 5- to 8-membered heterocycle such as pyrroline, pyrazoline, pyridine, dihydropyridine, tetrahydropyridine, pyrimidine, dihydropyrimidine, tetrahydropyrimidine, thiophene, dihydrothiophene, furan, dihydrofuran, pyran, dihydropyran, azepine, oxazepine and the like; and the like.

A compound represented by the formula (I) (hereinafter sometimes to be abbreviated as compound (I)) and a salt thereof of the present invention are explained below.

In the formula (I), X is S or O. X is preferably S.

In the formula (I), $R^1$ and $R^2$ are the same or different and each is a hydrogen atom, an optionally substituted $C_{6-14}$ aryl group, an optionally substituted heterocyclic group or an optionally substituted $C_{1-6}$ alkyl group, or $R^1$ and $R^2$ are bonded to each other to form a ring together with the carbon atom they are bonded to. $R^1$ and $R^2$ are each preferably a hydrogen atom, an optionally substituted $C_{6-14}$ aryl group, a heterocyclic group or an optionally halogenated $C_{1-6}$ alkyl group.

$R^1$ is preferably a hydrogen atom, and $R^2$ is preferably an optionally substituted $C_{6-14}$ aryl group or an optionally halogenated $C_{1-6}$ alkyl group, more preferably an optionally substituted $C_{6-14}$ aryl group.

As used herein, the optionally substituted $C_{6-14}$ aryl group is preferably a $C_{6-14}$ aryl group (preferably phenyl) optionally substituted by 1 to 3 substituents selected from a halogen atom and an optionally halogenated $C_{1-6}$ alkyl group.

In the formula (I), E is —$W^1$—$N(R^5)$—$W^2$—, —$W^1$—$CH(R^6)$—$O$—$W^2$—, —$W^1$—$O$—$CH(R^6)$—$W^2$—, —$W^1$—$S(O)n$-$W^2$— or —$W^1$—$CH(R^6)$—$W^2$— ($W^1$ and $W^2$ are the same or different and each is a bond or an optionally substituted $C_{1-3}$ alkylene group, $R^5$ and $R^6$ are each an optionally substituted heterocyclic group or an optionally substituted hydrocarbon group, and n is 1 or 2, provided that when X is S, then $R^5$ and $R^6$ are not $C_{1-6}$ alkyl groups) preferably —$W^1$—$N(R^5)$—$W^2$— or —$W^1$—$S(O)n$-$W^2$— ($W^1$, $W^2$, $R^5$ and n are as defined above). E is more preferably —$W^1$—$N(R^5)$—$W^2$— ($W^1$, $W^2$ and $R^5$ are as defined above, and $R^5$ is preferably an optionally substituted hydrocarbon group, more preferably an optionally substituted $C_{7-16}$ aralkyl group, provided that when X is S, then $R^5$ is not a $C_{1-6}$ alkyl group).

Preferable examples of $R^5$ include (1) a $C_{7-16}$ aralkyl group (preferably benzyl, phenethyl, 3-phenylpropyl) optionally substituted by 1 to 3 substituents selected from a halogen atom and a $C_{1-6}$ alkyl group, and (2) a $C_{1-6}$ alkyl group optionally substituted by 1 to 3 substituents selected from a $C_{1-6}$ alkoxy group, a $C_{1-6}$ alkylthio group, a mono- or di-$C_{1-6}$ alkyl-amino group, a heterocyclic group (preferably pyridyl), a $C_{1-6}$ alkylsulfinyl group and a $C_{1-6}$ alkylsulfonyl group (provided that when X is S, then $R^5$ is not a $C_{1-6}$ alkyl group).

In the formula (I), when X is S, $R^5$ is preferably a $C_{7-16}$ aralkyl group optionally substituted by 1 to 3 substituents selected from a halogen atom and a $C_{1-6}$ alkyl group.

Preferable examples of E include 1) —$W^1$—$N(R^5)$—$W^2$— ($W^1$ is a bond, $W^2$ is a $C_{1-3}$ alkylene group (preferably methylene), and $R^5$ is (1) a $C_{7-16}$ aralkyl group (preferably benzyl, phenethyl, 3-phenylpropyl) optionally substituted by 1 to 3 substituents selected from a halogen atom and a $C_{1-6}$ alkyl group, or
(2) a $C_{1-6}$ alkyl group optionally substituted by 1 to 3 substituents selected from a $C_{1-6}$ alkoxy group, a $C_{1-6}$ alkylthio group, a mono- or di-$C_{1-6}$ alkyl-amino group, a heterocyclic group (preferably pyridyl), a $C_{1-6}$ alkylsulfinyl group and a $C_{1-6}$ alkylsulfonyl group (provided that when X is S, then $R^5$ is not a $C_{1-6}$ alkyl group); and
2) —$W^1$—S(O)n-$W^2$— ($W^1$ is a bond, $W^2$ is a $C_{1-3}$ alkylene group (preferably methylene) optionally substituted by a $C_{1-6}$ alkyl group, and n is 1 or 2).

In the formula (I), ring $S^1$ is a benzene ring or a pyridine ring optionally further having substituent(s) selected from an optionally substituted $C_{1-6}$ alkyl group, an optionally substituted $C_{1-6}$ alkoxy group and a halogen atom. The number of the substituents is, for example, 1 or 2, and the position of substitution is not particularly limited. Ring $S^1$ is preferably a benzene ring or a pyridine ring, more preferably a benzene ring.

In the formula (I), $R^3$ and $R^4$ are the same or different and each is a hydrogen atom, a halogen atom, an optionally substituted $C_{1-6}$ alkyl group or an optionally substituted $C_{1-6}$ alkoxy group, preferably a hydrogen atom or a halogen atom (preferably a fluorine atom).

In the formula (I), $R^9$ and $R^{10}$ are the same or different and each is a hydrogen atom, a halogen atom or a $C_{1-6}$ alkoxy group, preferably a hydrogen atom or a halogen atom (preferably a fluorine atom), more preferably a hydrogen atom.

In the formula (I), R is an optionally substituted hydroxy group or an optionally substituted amino group, preferably an optionally substituted hydroxy group, more preferably a hydroxy group or a $C_{1-6}$ alkoxy group. Of these, a hydroxy group is preferable.

As the "preferable examples of compound (I)", the following compounds can be mentioned.

[Compound A]

A compound wherein
$R^1$ and $R^2$ are the same or different and each is
(1) a hydrogen atom,
(2) a $C_{6-14}$ aryl group (preferably phenyl) optionally substituted by a halogen atom,
(3) a heterocyclic group (preferably pyridyl), or
(4) a $C_{1-6}$ alkyl group;
E is —$W^1$—N($R^5$)—$W^2$—, wherein $W^1$ and $W^2$ are the same or different and each is a bond or a $C_{1-3}$ alkylene group (preferably, $W^1$ is a bond and $W^2$ is a $C_{1-3}$ alkylene group (preferably methylene)), and
$R^5$ is (1) a $C_{7-16}$ aralkyl group (preferably benzyl, phenethyl, 3-phenylpropyl) optionally substituted by 1 to 3 substituents selected from a halogen atom and a $C_{1-6}$ alkyl group, or
(2) a $C_{1-6}$ alkyl group optionally substituted by 1 to 3 substituents selected from a $C_{1-6}$ alkoxy group, a $C_{1-6}$ alkylthio group, a mono- or di-$C_{1-6}$ alkyl-amino group, a heterocyclic group (preferably pyridyl), a $C_{1-6}$ alkylsulfinyl group and a $C_{1-6}$ alkylsulfonyl group (provided that when X is S, then $R^5$ is not a $C_{1-6}$ alkyl group);
$R^3$ and $R^4$ are the same or different and each is a hydrogen atom or a halogen atom;
ring $S^1$ is a benzene ring;
$R^9$ and $R^{10}$ are hydrogen atoms; and
R is a hydroxy group or a $C_{1-6}$ alkoxy group (preferably a hydroxy group).

[Compound B]

A compound wherein
$R^1$ and $R^2$ are the same or different and each is
(1) a hydrogen atom,
(2) a $C_{6-14}$ aryl group (preferably phenyl) optionally substituted by 1 to 3 substituents selected from a halogen atom and an optionally halogenated $C_{1-6}$ alkyl group,
(3) a heterocyclic group (preferably pyridyl), or
(4) an optionally halogenated $C_{1-6}$ alkyl group;
E is 1) —$W^1$—N($R^5$)—$W^2$—, wherein $W^1$ and $W^2$ are the same or different and each is a bond or a $C_{1-3}$ alkylene group (preferably, $W^1$ is a bond and $W^2$ is a $C_{1-3}$ alkylene group (preferably methylene)), and
$R^5$ is (1) a $C_{7-16}$ aralkyl group (preferably benzyl, phenethyl, 3-phenylpropyl) optionally substituted by 1 to 3 substituents selected from a halogen atom and a $C_{1-6}$ alkyl group, or
(2) a $C_{1-6}$ alkyl group optionally substituted by 1 to 3 substituents selected from a $C_{1-6}$ alkoxy group, a $C_{1-6}$ alkylthio group, a mono- or di-$C_{1-6}$ alkyl-amino group, a heterocyclic group (preferably pyridyl), a $C_{1-6}$ alkylsulfinyl group and a $C_{1-6}$ alkylsulfonyl group (provided that when X is S, then $R^5$ is not a $C_{1-6}$ alkyl group); or
2) —$W^1$—S(O)n-$W^2$—, wherein $W^1$ and $W^2$ are the same or different and each is a bond or a $C_{1-3}$ alkylene group optionally substituted by a $C_{1-6}$ alkyl group (preferably, $W^1$ is a bond and $W^2$ is a $C_{1-3}$ alkylene group (preferably methylene) optionally substituted by a $C_{1-6}$ alkyl group), and
n is 1 or 2;
$R^3$ and $R^4$ are the same or different and each is a hydrogen atom or a halogen atom (preferably a fluorine atom);
ring $S^1$ is a benzene ring or a pyridine ring (preferably a benzene ring);
$R^9$ and $R^{10}$ are the same or different and each is a hydrogen atom or a halogen atom (preferably a fluorine atom); and
R is a hydroxy group or a $C_{1-6}$ alkoxy group (preferably a hydroxy group).

[Compound C]
3-[4-[[4-[[(2-phenylethyl)(4-phenyl-1,3-thiazol-2-yl)amino]methyl]benzyl]oxy]phenyl]propanoic acid (Example 32);
3-[2,6-difluoro-4-[[4-[[(2-phenylethyl)(4-phenyl-1,3-thiazol-2-yl)amino]methyl]benzyl]oxy]phenyl]propanoic acid (Example 42);
2-fluoro-3-{4-[(4-{[(2-phenylethyl)(4-phenyl-1,3-thiazol-2-yl)amino]methyl}benzyl)oxy]phenyl}propanoic acid (Example 51);
3-{2-fluoro-4-[(4-{1-[(4-phenyl-1,3-thiazol-2-yl)sulfonyl]butyl}benzyl)oxy]phenyl}propanoic acid (Example 57);

or a salt thereof.

As a salt of compound (I), for example, metal salts, ammonium salts, salts with organic bases, salts with inorganic acids, salts with organic acids, salts with basic or acidic amino acids and the like can be mentioned. Preferable examples of the metal salt include alkali metal salts such as a sodium salt, a potassium salt and the like; alkaline earth metal salts such as a calcium salt, a magnesium salt, a barium salt and the like; an aluminum salt, and the like. Preferable examples of the salt with an organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with an inorganic acid include a salt with hydrochloric acid, hydrobromic acid, nitric acid, sulfuric acid, phosphoric acid and the like. Preferable examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with a basic amino acid include a salt with arginine, lysin, ornithine and the like. Preferable examples of the salt with an acidic amino acid include a salt with aspartic acid, glutamic acid and the like.

Of these, a pharmacologically acceptable salt is preferable. For example, when the compound has an acidic functional group, metal salts such as alkali metal salts (e.g., a sodium salt, a potassium salt etc.), alkaline earth metal salts (e.g., a calcium salt, a magnesium salt, a barium salt etc.) and the like, an ammonium salt and the like are preferable, and when the compound has a basic functional group, salts with an inorganic acid such as hydrochloric acid, hydrobromic acid, nitric acid, sulfuric acid, phosphoric acid and the like; or salts with an organic acid such as acetic acid, phthalic acid, fumaric acid, oxalic acid, tartaric acid, maleic acid, citric acid, succinic acid, methanesulfonic acid, p-toluenesulfonic acid and the like are preferable.

A prodrug of compound (I) or a salt thereof is a compound that converts to compound (I) due to the reaction by an enzyme, gastric acid and the like under physiological conditions in the body; that is, a compound that converts to compound (I) by enzymatic oxidation, reduction, hydrolysis and the like, and a compound that converts to compound (I) by hydrolysis and the like by gastric acid and the like.

Examples of a prodrug of compound (I) include a compound wherein an amino group of compound (I) is acylated, alkylated or phosphorylated (e.g., a compound where an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidyl-methylated, pivaloyloxymethylated, tert-butylated, and the like); a compound wherein a hydroxy group of compound (I) is acylated, alkylated, phosphorylated or borated (e.g., a compound where a hydroxy group of compound (I) is acetylated, palmitoylated, propanoylated, pivaloylated, succinylated, fumarylated, alanylated, dimethylaminomethylcarbonylated, and the like); a compound wherein a carboxyl group of compound (I) is esterified or amidated (e.g., a compound where a carboxyl group of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated, and the like) and the like. Of these, a compound wherein a carboxyl group of compound (I) is esterified by a $C_{1-6}$ alkyl group such as methyl, ethyl, tert-butyl and the like is preferable. These compounds can be produced from compound (I) by a method known per se.

A prodrug of compound (I) may be a compound that converts to compound (I) under physiological conditions as described in *Development of Pharmaceutical Products*, vol. 7, Molecule Design, pp. 163-198, Hirokawa Shoten (1990).

Hereinafter the production methods of the compound (I) or a salt thereof are explained.

Each symbol in the following reaction schemes is as defined above unless particularly described. Each compound described in the reaction schemes may form a salt, and as such salt, those similar to the salts of compound (I) can be mentioned.

In each step of the reaction schemes, the product can be used in the next reaction in the form of a reaction mixture or a crude product. It can also be isolated from a reaction mixture according to a conventional method, and also easily purified by a general separation means (e.g., recrystallization, distillation, chromatography and the like). The amount of a solvent to be used for the production of each compound is not particularly limited as long as the reaction mixture can be stirred.

Compound (I) can be produced, for example, according to the method shown by the following reaction scheme 1 or a method analogous thereto.

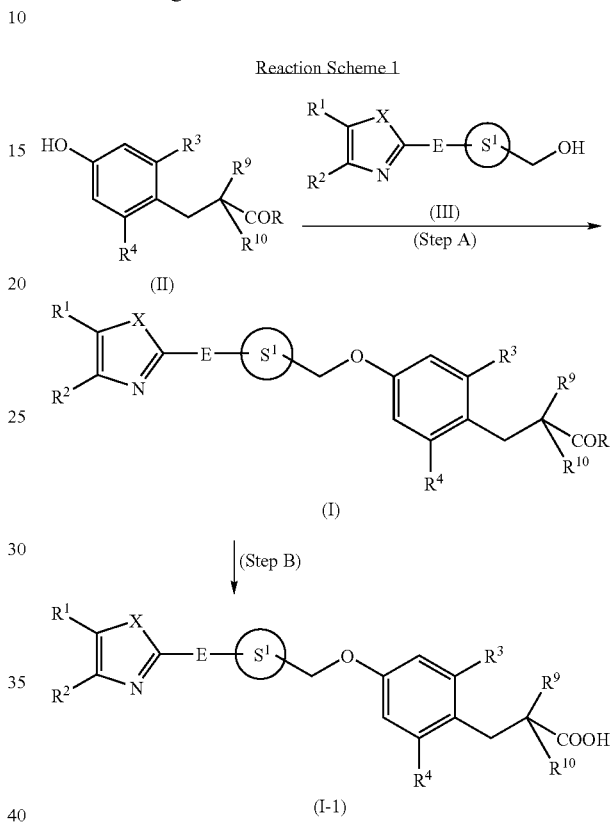

In the above-mentioned reaction scheme, the compounds represented by the formulas (I), (II), (III) and (I-1) are hereinafter to be abbreviated as compound (I), compound (II), compound (III) and compound (I-1), respectively.

Compound (I) and compound (I-1) can be produced by reacting compound (II) with compound (III) and hydrolyzing the obtained compound on demand.

The reaction between compound (II) and compound (III) is carried out using, for example, Mitsunobu reaction, (*Synthesis* (1981) pp. 1-27) (Step A). R of compound (II) to be used in Step A is desirably a substituted hydroxy group or an optionally substituted amino group.

In Step A, compound (II) and compound (III) are reacted in the presence of azodicarboxylates such as diethyl azodicarboxylate, diisopropyl azodicarboxylate, 1,1'-(azodicarbonyl)dipiperidine and the like and phosphines such as triphenylphosphine, tributylphosphine and the like.

The amount of compound (III) to be used is about 1 to about 5 mol, preferably about 1 to about 2 mol, per 1 mol of compound (II).

The amount of each of the "azodicarboxylates" and "phosphines" to be used is about 0.5 to about 5 mol, preferably about 1 to about 2 mol, per 1 mol of compound (II).

The reaction of Step A is advantageously carried out using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); cyclic ureas and amides (e.g., 1,3-dimethyl-2-imidazolidinone, N-methylpyrrolidone and the like); halogenated hydrocarbons (e.g., dichloromethane, chloroform and the like); nitriles (e.g., acetonitrile, propionitrile and the like); ketones (e.g., acetone, ethyl methyl ketone and the like); sulfoxides (e.g., dimethyl sulfoxide and the like), and the like, mixed solvents thereof and the like are preferable.

The reaction time of Step A is generally about 5 min to about 48 hr, preferably about 10 min to about 24 hr. The reaction temperature of Step A is generally about −20° C. to about 200° C., preferably about 0° C. to about 100° C.

In compound (I) obtained in Step A, when R is a substituted hydroxy group or an optionally substituted amino group (preferably a $C_{1-6}$ alkoxy group such as a methoxy group, an ethoxy group, a tert-butoxy group, an isopropoxy group and the like), compound (I) is hydrolyzed to give a compound (I) wherein R is a hydroxy group, i.e., compound (I-1) (Step B).

The hydrolysis is carried out using an acid or a base according to a conventional method. As the acid, for example, mineral acids (e.g., hydrochloric acid, sulfuric acid and the like); Lewis acids (e.g., boron trichloride, boron tribromide and the like); organic acids (e.g., trifluoroacetic acid, p-toluenesulfonic acid and the like), and the like are used. As used herein, Lewis acid can also be used concurrently with thiol or sulfide.

As the base, for example, alkali metal hydroxides (e.g., lithium hydroxide, sodium hydroxide, potassium hydroxide and the like); alkaline earth metal hydroxides (e.g., barium hydroxide and the like); alkali metal carbonates (e.g., sodium carbonate, potassium carbonate and the like); alkali metal alkoxides (e.g., sodium methoxide, sodium ethoxide, potassium tertiary butoxide and the like); organic bases (e.g., triethylamine, imidazole, formamidine and the like), and the like are used. The amount of these acids and bases to be used is about 0.5 to 10 mol, preferably about 0.5 to 6 mol, per 1 mol of compound (I).

Hydrolysis is carried out without solvent or in a solvent inert to the reaction. The solvent is not particularly limited as long as the reaction proceeds and, for example, solvents such as alcohols (e.g., methanol, ethanol, propanol and the like); aromatic hydrocarbons (e.g., benzene, toluene and the like); saturated hydrocarbons (e.g., cyclohexane, hexane and the like); organic acids (e.g., formic acid, acetic acid and the like); ethers (e.g., tetrahydrofuran, dioxane, 1,2-dimethoxyethane and the like); amides (e.g., N,N-dimethylformamide, N,N-dimethylacetamide and the like); cyclic ureas and amides (e.g., 1,3-dimethyl-2-imidazolidinone, N-methylpyrrolidone and the like); halogenated hydrocarbons (e.g., dichloromethane, chloroform, carbon tetrachloride, 1,2-dichloroethane and the like); ketones (e.g., acetone, methyl ethyl ketone and the like); sulfoxides (e.g., dimethyl sulfoxide and the like); water and the like, mixed solvents thereof and the like are preferable.

The reaction time of Step B is generally 10 min to 60 hr, preferably 10 min to 12 hr. The reaction temperature of Step B is generally −10° C. to 200° C., preferably 0° C. to 120° C.

Compounds (II) and (III) to be used for reaction scheme 1 are commercially easily available, and can also be produced according to a method known per se or a method analogous thereto. For example, of compounds (III), a compound of the formula (III-1) wherein E=—$W^1$—$N(R^5)$—$W^2$— and $W^1$ is a bond (compound (III-1)) can be produced by a method shown by the following reaction scheme 2.

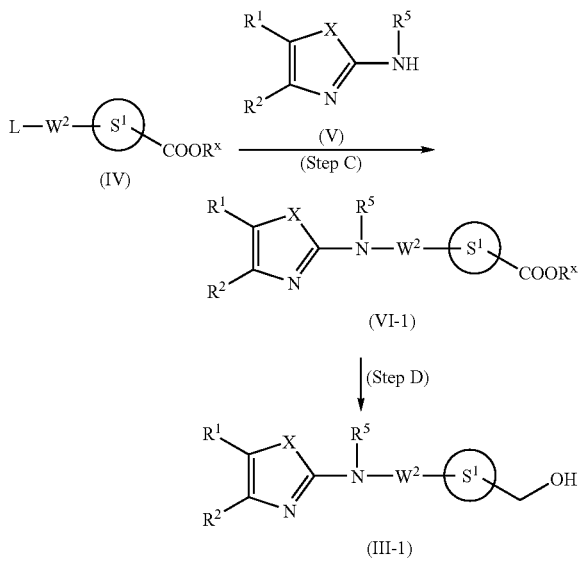

wherein L is a leaving group and $R^x$ is an optionally substituted hydrocarbon group.

In the above-mentioned reaction scheme, the compounds represented by the formulas (IV), (V) and (VI-1) are hereinafter to be abbreviated as compound (IV), compound (V) and compound (VI-1), respectively.

As the "leaving group" for L, for example, a halogen atom (e.g., a fluorine atom, a chlorine atom, a bromine atom, an iodine atom); an optionally halogenated $C_{1-6}$ alkylsulfonyloxy group (e.g., methanesulfonyloxy, ethanesulfonyloxy, trichloromethanesulfonyloxy and the like); a $C_{6-10}$ arylsulfonyloxy group optionally having substituent(s) and the like can be mentioned. As the "$C_{6-10}$ arylsulfonyloxy group optionally having substituent(s)", for example, a $C_{6-10}$ arylsulfonyloxy group (e.g., phenylsulfonyloxy, naphthylsulfonyloxy etc.) optionally having 1 to 3 substituents selected from a $C_{1-6}$ alkyl group (e.g., methyl, ethyl and the like), a $C_{1-6}$ alkoxy group (e.g., methoxy, ethoxy and the like), and a nitro group; and the like can be mentioned. Specific examples include phenylsulfonyloxy, m-nitrophenylsulfonyloxy, p-toluenesulfonyloxy and the like.

The "optionally substituted hydrocarbon group" for $R^x$ is the same as the aforementioned "optionally substituted hydrocarbon group", and a $C_{1-6}$ alkyl group (e.g., methyl, ethyl, tert-butyl, isopropyl and the like) is preferable.

In reaction scheme 2, compound (V) is reacted with compound (IV) to give compound (VI-1) (Step C).

The reaction of Step C is carried out without solvent or in a solvent inert to the reaction. The solvent is not particularly limited as long as the reaction proceeds and, for example, solvents such as amides (e.g., N,N-dimethylformamide, N,N-dimethylacetamide and the like); cyclic ureas and amides (e.g., 1,3-dimethyl-2-imidazolidinone, N-methylpyrrolidone and the like); sulfoxides (e.g., dimethyl sulfoxide and the like); aromatic hydrocarbons (e.g., benzene, toluene and the like); saturated hydrocarbons (e.g., cyclohexane, hexane and the like); ethers (e.g., diethyl ether, diisopropyl ether, diphenyl ether, tetrahydrofuran, 1,4-dioxane, 1,2-dimethoxyethane and the like); halogenated hydrocarbons (e.g., dichloromethane, chloroform and the like); esters (e.g., methyl acetate, ethyl acetate, butyl acetate and the like), and the like, mixed solvents thereof and the like are preferable.

When desired, the reaction of Step C is carried out in the presence of a base. As the "base", alkali metals (e.g., metal sodium, metal potassium and the like); metal hydrides (e.g., sodium hydride and the like); organic lithium reagents (e.g., butyl lithium and the like); tertiary amines (e.g., triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like); alkali metal hydroxides (e.g., lithium hydroxide, sodium hydroxide, potassium hydroxide, lithium hydroxide and the like); alkaline earth metal hydroxides (e.g., barium hydroxide and the like); alkali metal carbonates (e.g., sodium carbonate, potassium carbonate, cesium carbonate and the like); alkali metal hydrogen carbonates (e.g., sodium hydrogen carbonate and the like); acetates (e.g., sodium acetate, ammonium acetate and the like), and the like can be mentioned. The amount of the base to be used is about 1 to about 20 mol, preferably about 1 to about 10 mol, per 1 mol of compound (IV).

When $W^2$ of compound (IV) is a bond, the reaction can be generally promoted by the use of a metal catalyst. As the metal catalyst, metal complexes having various ligands can be used and, for example, palladium compounds [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium-2,2'-bis(diphenylphosphino)-1,1'-binaphthyl, a complex of palladium(II) acetate and 1,1'-bis(diphenylphosphino)ferrocene, and the like], nickel compounds [e.g., tetrakis(triphenylphosphine)nickel(0), bis(triethylphosphine)nickel(II) chloride, bis(triphenylphosphine)nickel(II) chloride and the like], rhodium compounds [e.g., tris(triphenylphosphine)rhodium(III) chloride and the like], cobalt compounds, copper compounds [e.g., copper oxide, copper(II) chloride and the like], platinum compounds and the like are used. Of these, palladium compounds, nickel compounds and copper compounds are preferable. The amount of the metal catalyst to be used is about 0.000001 to 5 mol, preferably about 0.0001 to 1 mol, per 1 mol of compound (IV). When a metal catalyst unstable to oxygen is used in this reaction, the reaction is preferably carried out in an inactive gas (e.g., argon gas or nitrogen gas) stream.

The amount of compound (V) to be used is about 1 to about 50 mol, preferably about 1 to about 2 mol, per 1 mol of compound (IV).

The reaction time of Step C is generally about 10 min to about 12 hr, preferably about 10 min to about 5 hr. The reaction temperature of Step C is generally about –30° C. to about 150° C., preferably about –20° C. to about 100° C.

Then, by subjecting compound (VI-1) to a reduction, compound (III-1) can be produced (Step D). The reduction is performed using a reducing agent according to a conventional method. As the reducing agent, for example, metal hydrides (e.g., aluminum hydride, diisobutylaluminum hydride, tributyltin hydride and the like); metal hydride complex compounds (e.g., lithium aluminum hydride, sodium borohydride and the like); borane complexes (e.g., a borane tetrahydrofuran complex, a borane dimethyl sulfide complex and the like); alkylboranes (e.g., thexylborane, disiamylborane and the like); diborane; metals (e.g., zinc, aluminum, tin, iron and the like); alkali metals (e.g., sodium, lithium and the like)/liquid ammonia (Birch reduction) and the like can be mentioned. The amount of the reducing agent to be used is appropriately determined according to the kind of the reducing agent. For example, the amount of each of the metal hydride, the metal hydride complex compound, the borane complex, alkylboranes and diborane to be used is about 1 to about 10 mol, preferably about 1 to about 5 mol, per 1 mol of compound (VI-I), and the amount of the metals (containing an alkali metal used for Birch reduction) to be used is about 1 to about 20 equivalents, preferably about 1 to about 5 equivalents, relative to compound (VI-I).

When desired, Lewis acids may be used for the reaction of Step D. As the "Lewis acids", for example, aluminum chloride, aluminum bromide, titanium tetrachloride, tin dichloride, zinc chloride, boron trichloride, boron tribromide, boron trifluoride and the like are used. The amount of the Lewis acid to be used is about 1 to about 10 mol, preferably about 1 to about 5 mol, per 1 mol of compound (VI-1).

The reaction of Step D is advantageously carried out using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like); ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); organic acids (e.g., formic acid, acetic acid, propanoic acid, trifluoroacetic acid, methanesulfonic acid and the like), and the like, mixed solvents thereof and the like are preferable.

While the reaction time of Step D varies depending on the kind and amount of the reducing agent, it is generally about 1 hr to about 100 hr, preferably about 1 hr to about 50 hr. The reaction temperature of Step D is generally about –20° C. to about 120° C., preferably about 0° C. to about 80° C.

The compounds (IV) and (V) to be used in reaction scheme 2 are commercially easily available, and can also be produced according to a method known per se or a method analogous thereto.

For example, compound (V) can be produced by the method shown by the following reaction scheme 3.

Reaction Scheme 3

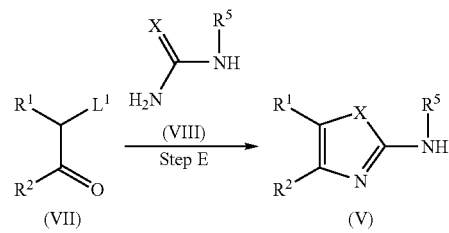

wherein $L^1$ is a leaving group.

In the above-mentioned reaction scheme, the compounds represented by the formulas (VII) and (VIII) are hereinafter to be abbreviated as compound (VII) and compound (VIII), respectively.

As the leaving group for $L^1$, those exemplified for the aforementioned L can be mentioned, and halogen atoms such as a chlorine atom, a bromine atom and the like are preferable.

In reaction scheme 3, compound (VII) is reacted with compound (VIII) to give compound (V) (Step E).

The reaction of Step E is carried out without solvent or in a solvent inert to the reaction. The solvent is not particularly limited as long as the reaction proceeds and, for example, solvents such as alcohols (e.g., methanol, ethanol, 1-propanol, 2-propanol, tert-butyl alcohol and the like); amides (e.g., N,N-dimethylformamide, N,N-dimethylacetamide and the like); cyclic ureas and amides (e.g., 1,3-dimethyl-2-imidazolidinone, N-methylpyrrolidone and the like); aromatic hydrocarbons (e.g., benzene, toluene and the like); saturated hydrocarbons (e.g., cyclohexane, hexane and the like); ethers (e.g., diethyl ether, diisopropyl ether, diphenyl ether, tetrahydrofuran, 1,4-dioxane, 1,2-dimethoxyethane and the like); halogenated hydrocarbons (e.g., dichloromethane, chloroform, 1,2-dichloroethane and the like); esters (e.g., methyl acetate, ethyl acetate, butyl acetate and the like), and the like, mixed solvents thereof and the like are preferable.

When desired, the reaction of Step E is carried out in the presence of a base. As the "base", tertiary amines (e.g., triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like); alkali metal hydroxides (e.g., sodium hydroxide, potassium hydroxide, lithium hydroxide and the like); alkaline earth metal hydroxides (e.g., barium hydroxide and the like); alkali metal carbonates (e.g., sodium carbonate, potassium carbonate, cesium carbonate and the like); alkali metal hydrogen carbonates (e.g., sodium hydrogen carbonate and the like); acetates (e.g., sodium acetate, ammonium acetate and the like), and the like can be mentioned. The base is used in an amount of about 1 to about 20 mol, preferably about 1 to about 10 mol, per 1 mol of compound (VII).

The amount of compound (VIII) to be used is about 0.3 to about 10 mol, preferably about 0.5 to about 2 mol, per 1 mol of compound (VII).

The reaction time of Step E is generally about 10 min to about 12 hr, preferably about 10 min to about 5 hr. The reaction temperature of Step E is generally about −30° C. to about 200° C., preferably about −20° C. to about 150° C.

While compound (V) obtained by the reaction of Step E is generally isolated and purified by a suitable separation means (e.g., recrystallization, distillation, chromatography and the like) and then used for the next reaction (the aforementioned Step C); in some cases, this isolation and purification step may be omitted and the reaction mixture containing compound (V) obtained by the present Step E may be directly used for the next Step C. In this case, Step E is performed without solvent or in a solvent inert to Step C. As such solvent, solvents such as amides (e.g., N,N-dimethylformamide, N,N-dimethylacetamide and the like); cyclic ureas and amides (e.g., 1,3-dimethyl-2-imidazolidinone, N-methylpyrrolidone and the like); aromatic hydrocarbons (e.g., benzene, toluene and the like); saturated hydrocarbons (e.g., cyclohexane, hexane and the like); ethers (e.g., diethyl ether, diisopropyl ether, diphenyl ether, tetrahydrofuran, 1,4-dioxane, 1,2-dimethoxyethane and the like); halogenated hydrocarbons (e.g., dichloromethane, chloroform and the like); esters (e.g., methyl acetate, ethyl acetate, butyl acetate and the like), and the like, mixed solvents thereof and the like are preferable.

The compounds (VII) and (VIII) to be used in reaction scheme 3 are commercially easily available, and can also be produced according to a method known per se or a method analogous thereto.

Of compounds (I), compounds of the formulas (I-2) and (I-3) wherein E=—W$^1$—N(R$^5$)—W$^2$— and W$^1$ is a bond (compound (I-2) and compound (I-3)) can also be produced by the method shown in the following reaction scheme 4.

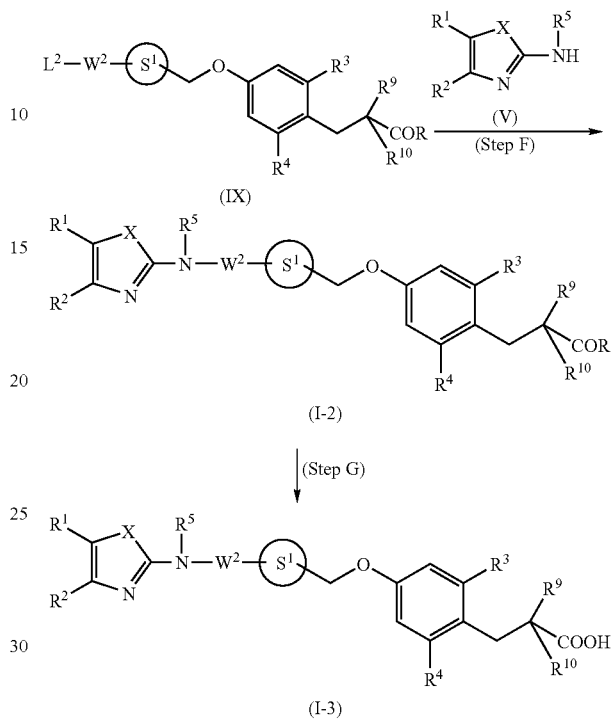

wherein L$^2$ is a leaving group.

In the above-mentioned reaction scheme, the compound represented by the formula (IX) is hereinafter to be abbreviated as compound (IX).

As the leaving group for L$^2$, those exemplified for the aforementioned L can be mentioned.

In reaction scheme 4, compound (V) is reacted with compound (IX) to give compound (I-2) (Step F).

The reaction of Step F is carried out without solvent or in a solvent inert to the reaction. The solvent is not particularly limited as long as the reaction proceeds and, for example, solvents such as amides (e.g., N,N-dimethylformamide, N,N-dimethylacetamide and the like); cyclic ureas and amides (e.g., 1,3-dimethyl-2-imidazolidinone, N-methylpyrrolidone and the like); sulfoxides (e.g., dimethyl sulfoxide and the like); aromatic hydrocarbons (e.g., benzene, toluene and the like); saturated hydrocarbons (e.g., cyclohexane, hexane and the like); ethers (e.g., diethyl ether, diisopropyl ether, diphenyl ether, tetrahydrofuran, 1,4-dioxane, 1,2-dimethoxyethane and the like); halogenated hydrocarbons (e.g., dichloromethane, chloroform, carbon tetrachloride and the like); esters (e.g., methyl acetate, ethyl acetate, butyl acetate and the like), and the like, mixed solvents thereof and the like are preferable.

When desired, the reaction of Step F is carried out in the presence of a base. As the "base", those exemplified for the aforementioned Step C can be used. The amount of the base to be used is about 1 to about 20 mol, preferably about 1 to about 10 mol, per 1 mol of compound (IX).

When W$^2$ of compound (IX) is a bond, the reaction can be promoted using a metal catalyst as in Step C. The amount of the metal catalyst to be used is about 0.000001 to 5 mol, preferably about 0.0001 to 1 mol, per 1 mol of compound (IX).

The amount of compound (V) to be used is about 1 to about 5 mol, preferably about 1 to about 2 mol, per 1 mol of compound (IX). As compound (V) in Step F, for example, a reaction mixture containing compound (V) obtained by the reaction of the aforementioned Step E can be directly used. In this case, Step E is performed using a solvent inert to Step F.

The reaction time of Step F is generally about 10 min to about 12 hr, preferably about 10 min to about 5 hr. The reaction temperature of Step F is generally about −30° C. to about 150° C., preferably about −20° C. to about 100° C.

In compound (I-2) obtained by Step F, when R is a substituted hydroxy group or an optionally substituted amino group (preferably a $C_{1-6}$ alkoxy group such as a methoxy group, an ethoxy group, a tert-butoxy group, an isopropoxy group and the like), compound (I-2) is hydrolyzed to give a compound (I-2) wherein R is a hydroxy group, i.e., compound (I-3) (Step G).

The hydrolysis is carried out in the same manner as in the aforementioned reaction scheme 1, Step B.

While compound (I-2) to be used in reaction scheme 4, Step G is, after production by Step F, generally isolated and purified by a suitable separation means (e.g., recrystallization, distillation, chromatography and the like) and then used; in some cases, this isolation and purification step may be omitted and the reaction mixture containing compound (I-2) obtained by Step F may be directly used for the next Step G. In this case, hydrolysis of Step G is preferably carried out using a base. Hydrolysis using a base can also be carried out after completion of Step F, by adding a suitable base and a solvent as necessary to the reaction mixture containing the obtained compound (I-2). When an excess base is used in Step F, the hydrolysis of Step G proceeds by the action of the base, and compound (I-3) may be obtained even without particular addition.

The compounds (IX) to be used in reaction scheme 4 can be produced according to a method known per se or a method analogous thereto. For example, compound (IX) can be produced by a method shown in the following reaction scheme 5.

Reaction Scheme 5

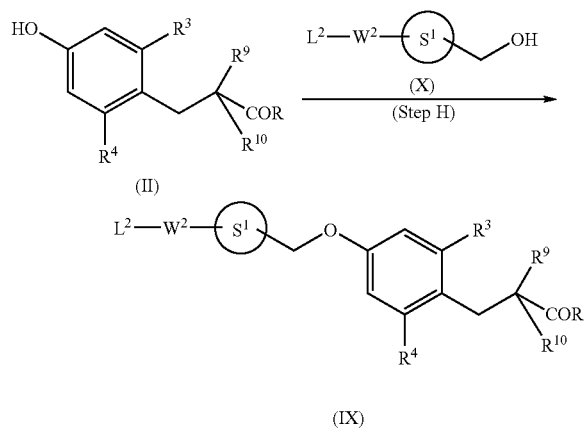

In the above-mentioned reaction scheme, a compound represented by the formula (X) is hereinafter to be abbreviated as compound (X).

In reaction scheme 5, compound (II) is reacted with compound (X) to give compound (IX) (Step H). This reaction is carried out in the same manner as in the aforementioned reaction scheme 1, Step A.

R of compound (II) to be used in Step H is desirably a substituted hydroxy group or an optionally substituted amino group. The compound (X) to be used in reaction scheme 5 is commercially easily available, and can also be produced according to a method known per se or a method analogous thereto.

Of the aforementioned compounds (III), a compound of the formula (III-2) wherein $E=\!-\!W^1\!-\!N(R^5)\!-\!W^2\!-\!$ and $W^1$ is $-\!W^3\!-\!CH(R^y)\!-\!$ ($W^3$ is a bond or an optionally substituted $C_{1-2}$ alkylene group, and $R^y$ is a hydrogen atom or an optionally substituted $C_{1-2}$ alkyl group) (compound (III-2)) is produced by, for example, the method shown in the following reaction scheme 6.

Reaction Scheme 6

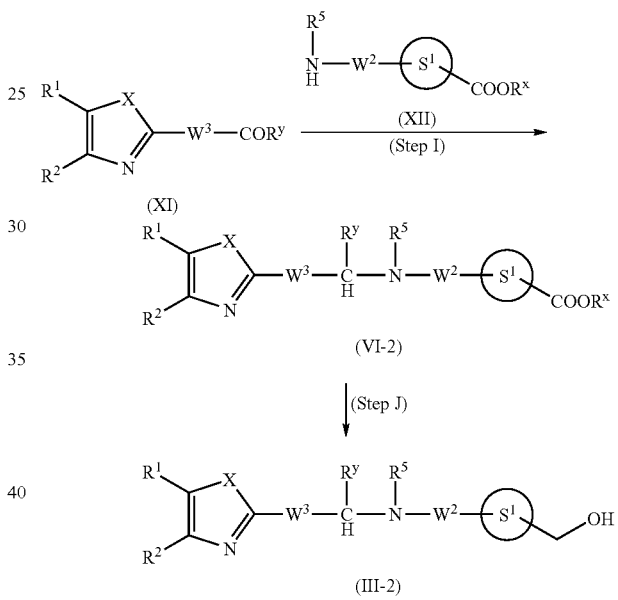

In the above-mentioned reaction scheme, the compounds represented by the formulas (XI), (XII) and (VI-2) are hereinafter to be abbreviated as compound (XI), compound (XII) and compound (VI-2), respectively.

As the substituent of the "optionally substituted $C_{1-2}$ alkyl group" for $R^y$, substituents exemplified for the aforementioned "optionally substituted $C_{1-3}$ alkylene group" can be mentioned.

As the "optionally substituted $C_{1-2}$ alkylene group" for $W^3$, an "optionally substituted $C_{1-3}$ alkylene group" exemplified for the aforementioned $W^1$, wherein the "$C_{1-3}$ alkylene group" is a "$C_{1-2}$ alkylene group" can be mentioned.

However, when $W^3$ is a bond, $R^y$ is an optionally substituted $C_{1-2}$ alkyl group, when $W^3$ is an "optionally substituted methylene group", $R^y$ is an optionally substituted methyl group, and when $W^3$ is an "optionally substituted ethylene group", $R^y$ is a hydrogen atom.

In reaction scheme 6, compound (XI) and compound (XII) are subjected to reductive amination (e.g., *J. Am. Chem. Soc.* (1971) pp. 2897-2904) to give compound (VI-2) (Step I). In the reductive amination, an imine compound produced by reacting compound (XI) with compound (XII) is subjected to reduction to give compound (VI-2).

The reduction is generally carried out using a reducing agent and according to a conventional method. As the reducing agent, for example, metal hydrides (e.g., aluminum hydride, diisobutylaluminum hydride, tributyltin hydride and the like); metal hydride complex compounds (e.g., sodium cyanoborohydride, sodium triacetoxyborohydride, sodium borohydride and the like); borane complexes (e.g., a borane tetrahydrofuran complex, a borane dimethyl sulfide complex and the like); alkylboranes (e.g., thexylborane, disiamylborane and the like); diborane; metals (e.g., zinc, aluminum, tin, iron and the like); alkali metals (e.g., sodium, lithium and the like)/liquid ammonia (Birch reduction), and the like can be mentioned. The amount of the reducing agent to be used is appropriately determined according to the kind of the reducing agent. For example, the amount of each of the metal hydride and the metal hydride complex compound to be used is about 1 to about 10 mol, preferably about 1 to about 5 mol, per 1 mol of compound (XI), the amount of each of the borane complex, alkylboranes and diborane to be used is about 1 to about 10 mol, preferably about 1 to about 5 mol, per 1 mol of compound (XI), and the amount of the metals (including alkali metal used for Birch reduction) to be used is about 1 to about 20 equivalents, preferably about 1 to about 5 equivalents, per 1 mol of compound (XI).

In addition, the reduction can also be performed by a hydrogenation reaction. In this case, for example, catalysts such as palladium carbon, platinum dioxide, Raney-nickel, Raney-cobalt and the like are used. The amount of the catalyst to be used is about 5 to about 1000 wt %, preferably about 10 to about 300 wt %, per 1 mol of compound (XI). The hydrogenation reaction can also be carried out using various hydrogen sources instead of hydrogen gas. As the hydrogen source, for example, formic acid, ammonium formate, triethylammonium formate, sodium phosphinate, hydrazine and the like are used. The amount of the hydrogen source to be used is about 1 to about 10 mol, preferably about 1 to about 5 mol, per 1 mol of compound (XI).

The reaction of Step I is advantageously carried out in a solvent inert to the reaction. The solvent is not particularly limited as long as the reaction proceeds and, for example, solvents such as alcohols (e.g., methanol, ethanol, 1-propanol, 2-propanol, tert-butyl alcohol and the like); ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); organic acids (e.g., formic acid, acetic acid, propanoic acid, trifluoroacetic acid, methanesulfonic acid and the like), and the like, mixed solvents thereof and the like are preferable.

Then, compound (VI-2) is subjected to reduction to give compound (III-2) (Step J). The reduction is performed in the same manner as in the aforementioned reaction scheme 2, Step D.

The compounds (XI) and (XII) to be used in reaction scheme 6 are commercially easily available, and can also be produced according to a method known per se or a method analogous thereto.

Of the aforementioned compounds (III), a compound of the formula (III-3) wherein E=—W$^1$—CH(R$^6$)—O—W$^2$— (compound (III-3)) is produced by, for example, the method shown in the following reaction scheme 7.

Reaction Scheme 7

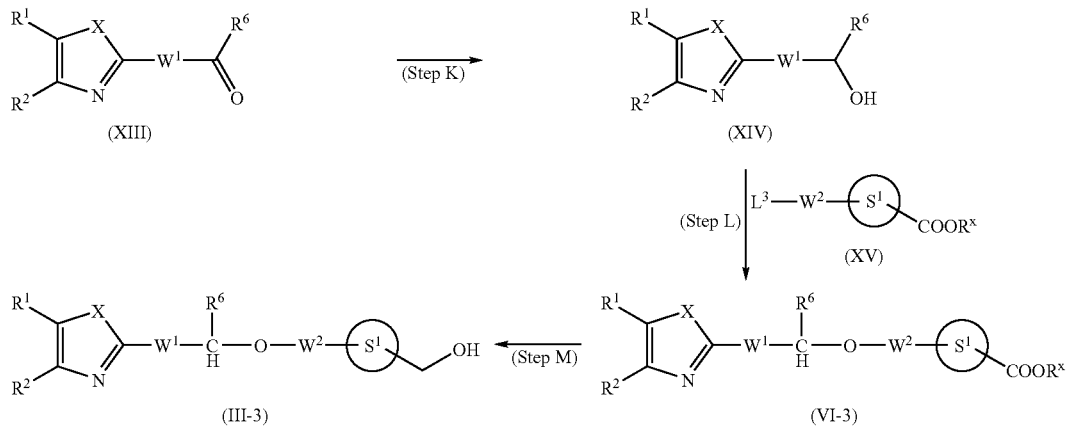

wherein L$^3$ is a hydroxyl group or a leaving group.

In the above-mentioned reaction scheme, the compounds represented by the formulas (XIII), (XIV), (XV) and (VI-3) are hereinafter to be abbreviated as compound (XIII), compound (XIV), compound (XV) and compound (VI-3), respectively.

As the leaving group for L$^3$, those exemplified for the aforementioned L can be mentioned.

In reaction scheme 7, compound (XIII) is subjected to reduction to give compound (XIV) (Step K). The reduction is performed in the same manner as in reaction scheme 2, Step D.

Then, the obtained compound (XIV) is reacted with compound (XV) to give compound (VI-3) (Step L). This reaction is appropriately selected according to the kind of W$^2$ in compound (XV). For example, compound (VI-3) wherein W$^2$ is a bond can be produced in the same manner as in reaction scheme 1, Step A and using compound (XV) wherein L$^3$ is a hydroxyl group. In addition, compound (VI-3) wherein W$^2$ is an optionally substituted C$_{1-3}$ alkylene group can be produced, for example, by reacting compound (XV) wherein L$^3$ is a leaving group exemplified for the aforementioned L with compound (XIV) in the presence of, when desired, a base. The reaction is carried out, for example, in the same manner as in reaction scheme 2, Step C.

In reaction scheme 7, moreover, compound (VI-3) is subjected to reduction to give compound (III-3) (Step M). The reduction is performed in the same manner as in the aforementioned reaction scheme 2, Step D.

The compounds (XIII) and (XV) to be used in reaction scheme 7 are commercially easily available, and can also be produced according to a method known per se or a method analogous thereto.

Of the aforementioned compounds (III), a compound of the formula (III-4) wherein E=—W$^1$—CH(R$^6$)—W$^2$— and W$^2$ is —CH$_2$—W$^4$— (W$^4$ is a bond or an optionally substituted C$_{1-2}$ alkylene group) (compound (III-4)) is produced by, for example, the method shown in the following reaction scheme 8.

ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); cyclic ureas and amides (e.g., 1,3-dimethyl-2-imidazolidinone, N-methylpyrrolidone and the like), mixed solvents thereof and the like are preferable. The amount of the triarylphosphines to be used is about 1 to about 5 mol, preferably about 1 to about 2 mol, per 1 mol of compound (XVI).

In Step N, the phosphonium salt of compound (XVI) can also be isolated, or a reaction may be continuously carried out without isolation, by adding compound (XIII) to the reaction mixture containing the phosphonium salt of compound (XVI).

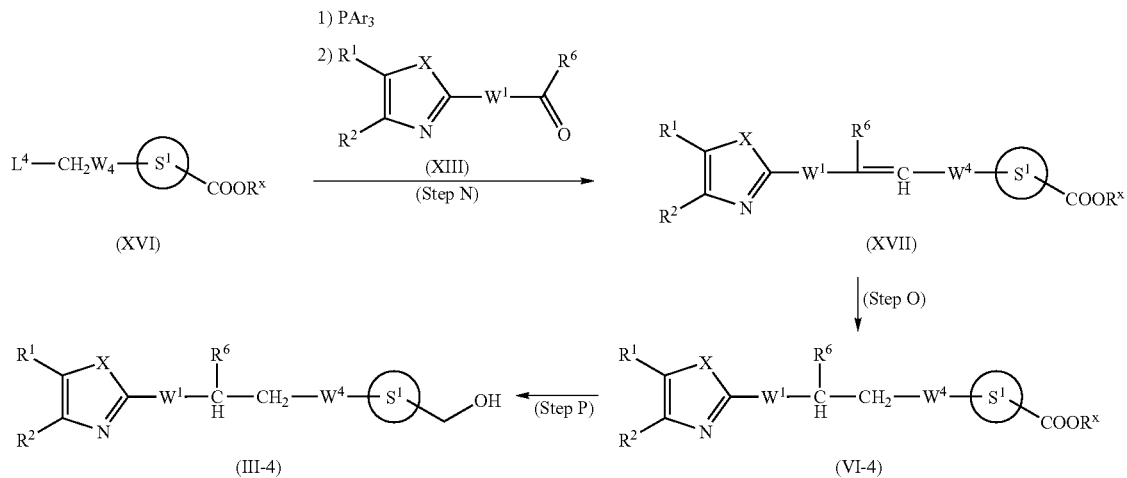

wherein Ar is an optionally substituted phenyl group and L$^4$ is a leaving group.

In the above-mentioned reaction scheme, the compounds represented by the formulas (XVI), (XVII) and (VI-4) are hereinafter to be abbreviated as compound (XVI), compound (XVII) and compound (VI-4), respectively.

As the "optionally substituted C$_{1-2}$ alkylene group" for W$^4$, those exemplified for the aforementioned W$^3$ can be mentioned. As the leaving group for L$^4$, those exemplified for the aforementioned L can be mentioned. Of these, halogen atoms such as a chlorine atom, a bromine atom, an iodine atom and the like are preferable. As the "optionally substituted phenyl group" for Ar, an "optionally substituted C$_{6-14}$ aryl group" wherein the C$_{6-14}$ aryl group is a phenyl group can be mentioned.

As the triarylphosphines represented by the formula: PAr$_3$, for example, triphenylphosphine and the like are used.

In reaction scheme 8, compound (XVI) is reacted with triarylphosphines to give a phosphonium salt of compound (XVI) and the phosphonium salt is reacted with compound (XIII) to give compound (XVII) (Step N).

The reaction between compound (XVI) and triarylphosphines is advantageously carried out using a solvent inert to the reaction. The solvent is not particularly limited as long as the reaction proceeds and, for example, ethers (e.g., diethyl The reaction of the phosphonium salt of compound (XVI) with compound (XIII) is carried out using, for example, the Wittig reaction. The reaction is generally carried out in the presence of a base. As the base, metal hydrides (e.g., sodium hydride and the like); tertiary amines (e.g., triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like); alkali metal hydroxides (e.g., sodium hydroxide, potassium hydroxide, lithium hydroxide and the like); alkaline earth metal hydroxides (e.g., barium hydroxide and the like); alkali metal carbonates (e.g., sodium carbonate, potassium carbonate, cesium carbonate and the like); alkali metal hydrogen carbonates (e.g., sodium hydrogen carbonate and the like); acetates (e.g., sodium acetate, ammonium acetate and the like); organic lithiums (e.g., methyllithium, n-butyllithium, sec-butyllithium, tert-butyllithium and the like); metal amides (e.g., sodium amide, lithium diisopropylamide, lithium hexamethyldisilazide and the like), and the like can be mentioned. These bases are used in an amount of about 1 to about 20 mol, preferably about 1 to about 10 mol, per 1 mol of compound (XVI) or the phosphonium salt thereof.

The amount of compound (XIII) to be used is about 1 to about 5 mol, preferably about 1 to about 2 mol, per 1 mol of compound (XVI) or the phosphonium salt thereof.

The reaction of the phosphonium salt of compound (XVI) with compound (XIII) is advantageously carried out in a solvent inert to the reaction. The solvent is not particularly limited as long as the reaction proceeds and, for example, ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); cyclic ureas and amides (e.g., 1,3-dimethyl-2-imidazolidinone, N-methylpyrrolidone and the like), mixed solvents thereof and the like are preferable.

Then, compound (XVII) is subjected to a hydrogenation reaction to give compound (VI-4) (Step O). The hydrogenation reaction is carried out in the same manner as in the hydrogenation reaction exemplified in the aforementioned reaction scheme 6, Step I.

Then, compound (VI-4) is subjected to a reduction to give compound (III-4) (Step P). The reduction is performed in the same manner as in the aforementioned reaction scheme 2, Step D.

The compound (XVI) to be used in reaction scheme 8 can be produced according to a method known per se or a method analogous thereto.

Of compounds (I), compounds of the formulas (I-4) and (I-5) wherein E=W$^1$—S(O)n-W$^2$— and W$^1$ is a bond (compound (I-4) and compound (I-5)) can also be produced according to the method shown in the following reaction scheme 9.

In the above-mentioned reaction scheme, the compounds represented by the formulas (XVIII), (XIX) and (XX) are hereinafter to be abbreviated as compound (XVIII), compound (XIX) and compound (XX), respectively.

As the leaving group for L$^5$, those exemplified for the aforementioned L can be mentioned.

In reaction scheme 9, compound (XVIII) is reacted with compound (XIX) to give compound (XX) (Step Q). This reaction is appropriately selected according to the kind of L$^5$ in compound (XVIII).

When L$^5$ is a hydroxy group, this reaction is carried out in the same manner as in the aforementioned reaction scheme 1, Step A. When L$^5$ is a leaving group, this reaction is carried out in the same manner as in the aforementioned reaction scheme 2, Step C.

The compounds (XVIII) and (XIX) to be used in reaction scheme 9 are commercially easily available, and can also be produced according to a method known per se or a method analogous thereto.

Then, compound (XX) is subjected to an oxidization to give compound (I-4) (Step R). This reaction is carried out using an oxidant and according to a conventional method. As the oxidant, for example, hydrogen peroxide, peracids (e.g., peracetic acid, perbenzoic acid, m-chloroperbenzoic acid and the like); sodium metaperiodide, hydroperoxide, ozone, selenium dioxide, chromic acid, dinitrogen tetraoxide, acyl nitrate, iodine, bromine, N-bromosuccinimide, iodosylbenzene, sulfuryl chloride and wet silica gel, tertiary butyl hypochloride and the like can be mentioned. The amount of the oxidant to be used is about 0.5 to 10.0 mol, preferably about 1.0 to 5.0 mol, per 1 mol of compound (XX).

Reaction Scheme 9

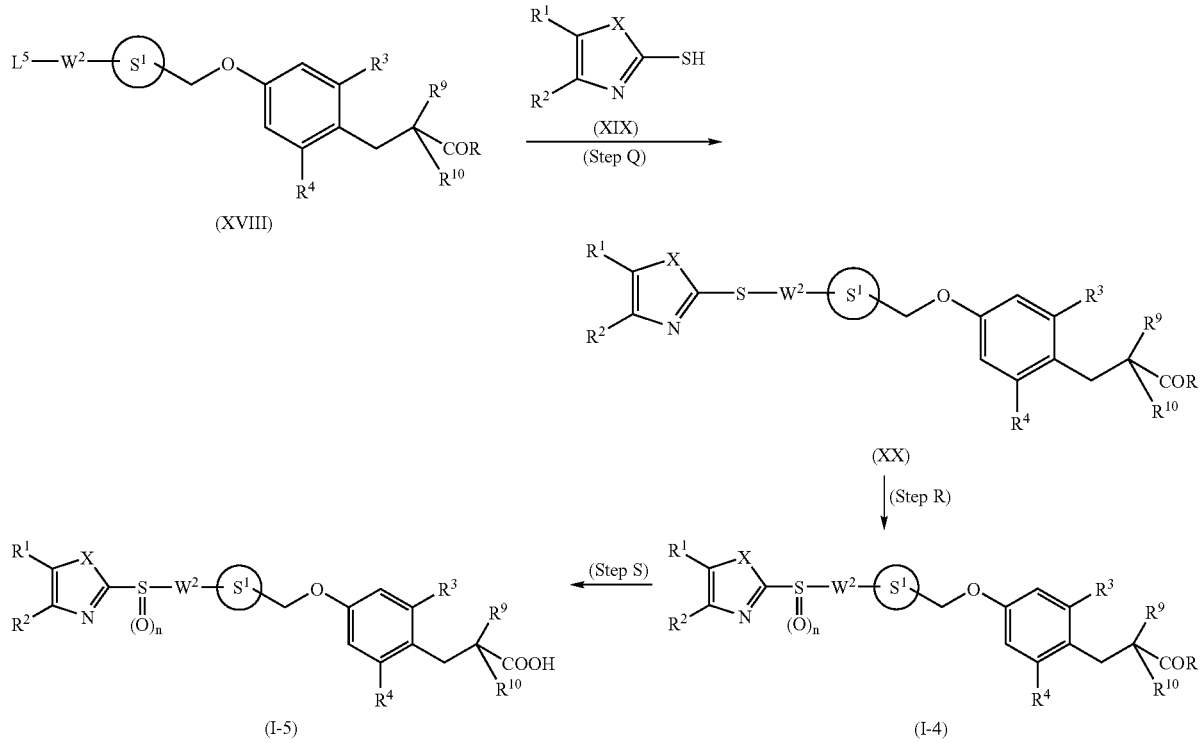

wherein L$^5$ is a hydroxyl group or a leaving group.

This reaction is advantageously carried out in a solvent inert to the reaction. The solvent is not particularly limited as long as the reaction proceeds and, for example, solvents such as alcohols (e.g., methanol, ethanol, propanol and the like); ethers (e.g., diethyl ether, tetrahydrofuran, dioxane, 1,2-dimethoxyethane and the like); ketones (e.g., acetone, methyl ethyl ketone and the like); hydrocarbons (e.g., benzene, toluene, cyclohexane, hexane and the like); amides (e.g., N,N-dimethylformamide, N,N-dimethylacetamide and the like); halogenated hydrocarbons (e.g., dichloromethane, chloroform, carbon tetrachloride, 1,2-dichloroethane and the like); organic acids (e.g., formic acid, acetic acid and the like); water; and the like, mixed solvents thereof and the like are preferable.

While the reaction time varies depending on the kind and amount of the oxidant to be used, it is generally 5 min to 48 hr, preferably 10 min to 12 hr.

The reaction temperature is generally −40° C. to 200° C., preferably −10° C. to 120° C.

In compound (I-4) obtained by Step R, when R is a substituted hydroxy group or an optionally substituted amino group (preferably a $C_{1-6}$ alkoxy group such as a methoxy group, an ethoxy group, a tert-butoxy group, an isopropoxy group and the like), compound (I-4) is hydrolyzed to give a compound (I-4) wherein R is a hydroxy group, i.e., compound (I-5) (Step S).

The hydrolysis is carried out in the same manner as in the aforementioned reaction scheme 1, Step B.

Each compound produced by the above-mentioned reaction schemes 1-9 can be easily purified by a conventional separation means (e.g., recrystallization, distillation, chromatography and the like), and certain compounds can be converted to salts thereof, prodrugs and the like by a method known per se.

In each of the aforementioned reactions, when the starting compound has an amino group, a carboxyl group, a hydroxy group or a mercapto group as a substituent, a protecting group generally used in peptide chemistry and the like may be introduced into these groups. By eliminating the protecting group as necessary after the reaction, the objective compound can be obtained.

As the amino-protecting group, for example, a formyl group; a $C_{1-6}$ alkyl-carbonyl group (e.g., acetyl, ethylcarbonyl and the like), a phenylcarbonyl group, a $C_{1-6}$ alkyl-oxycarbonyl group (e.g., methoxycarbonyl, ethoxycarbonyl, tert-butoxycarbonyl (Boc) and the like), an allyloxycarbonyl (Aloc) group, a phenyloxycarbonyl group, a fluorenylmethyoxycarbonyl (Fmoc) group, a $C_{7-10}$ aralkyl-carbonyl group (e.g., benzylcarbonyl and the like), a $C_{7-10}$ aralkyloxy-carbonyl group (e.g., benzyloxycarbonyl (Z) and the like), a $C_{7-10}$ aralkyl group (e.g., benzyl and the like), a trityl group, a phthaloyl group, a dithiasuccinoyl group or a N,N-dimethylaminomethylene group and the like, each of which optionally has substituent(s), can be mentioned. As the substituent, a phenyl group, a halogen atom, a $C_{1-6}$ alkyl-carbonyl group (e.g., acetyl, ethylcarbonyl, butylcarbonyl and the like), a $C_{1-6}$ alkoxy group optionally substituted by halogen atom (e.g., methoxy, ethoxy, trifluoromethoxy and the like), a nitro group and the like can be used. The number of the substituents is about 1 to 3.

As the carboxy-protecting group, for example, a $C_{1-6}$ alkyl group, an allyl group, a benzyl group, a phenyl group, a trityl group, a trialkylsilyl group and the like, each of which optionally has substituent(s), can be mentioned. As the substituent, a halogen atom, a formyl group, a $C_{1-6}$ alkyl-carbonyl group (e.g., acetyl, ethylcarbonyl, butylcarbonyl and the like), a $C_{1-6}$ alkoxy group optionally substituted by a halogen atom (e.g., methoxy, ethoxy, trifluoromethoxy and the like), a nitro group and the like can be used. The number of the substituents is about 1 to 3.

As the hydroxy-protecting group, for example, a $C_{1-6}$ alkyl group, a $C_{7-20}$ aralkyl group (e.g., benzyl, trityl and the like), a formyl group, a $C_{1-6}$ alkyl-carbonyl group (e.g., acetyl, ethylcarbonyl and the like), a benzoyl group, a $C_{7-10}$ aralkyl-carbonyl group (e.g., benzylcarbonyl and the like), a tetrahydropyranyl group, a furanyl group, a trialkylsilyl group (e.g., trimethylsilyl, tert-butyldimethylsilyl, diisopropylethylsilyl and the like) and the like, each of which optionally has substituent(s), can be mentioned. As the substituent, a halogen atom, a $C_{1-6}$ alkyl group, a phenyl group, a $C_{7-10}$ aralkyl group (e.g., benzyl and the like), a $C_{1-6}$ alkoxy group, a nitro group and the like can be used. The number of the substituents is about 1 to 4.

As the mercapto-protecting group, for example, a $C_{1-6}$ alkyl group, a $C_{1-6}$ alkyl-carbonyl group (e.g., acetyl, ethylcarbonyl and the like), a $C_{7-20}$ aralkyl group (e.g., benzyl, trityl and the like) and the like, each of which optionally has substituent(s), can be mentioned. As the substituent, a halogen atom, a $C_{1-6}$ alkyl group, a phenyl group, a $C_{7-10}$ aralkyl group (e.g., benzyl and the like), a $C_{1-6}$ alkoxy group, a nitro group and the like can be used. The number of the substituents is about 1 to 4.

For elimination of the protecting group, a method known per se or a method analogous thereto is used. For example, a treatment with an acid, a base, reduction, ultraviolet rays, hydrazine, phenylhydrazine, sodium N-methyldithiocarbamate, tetrabutylammonium fluoride, palladium acetate and the like are used.

Compound (I) obtained in this manner, other reaction intermediates and starting compounds thereof can be isolated and purified from the reaction mixture by a method known per se, such as extraction, concentration, neutralization, filtration, distillation, recrystallization, column chromatography, thin layer chromatography, preparative high performance liquid chromatography (preparative HPLC), medium pressure preparative liquid chromatography (medium pressure preparative LC) and the like.

The salt of compound (I) can be produced according to a method known per se. For example, when compound (I) is a basic compound, the salt can be produced by adding an inorganic acid or an organic acid, or when compound (I) is an acidic compound, the salt can be produced by adding an organic base or an inorganic base.

When compound (I) has optical isomers, such respective optical isomers and mixtures thereof are naturally encompassed in the scope of the present invention, and where desired, such isomers can also be subjected to optical resolution or individually produced according to a method known per se.

When compound (I) is present as a configurational isomer (position isomer), diastereomer, conformer or the like, each can be isolated by the above-mentioned separation and purification methods on demand. In addition, when compound (I) is in the form of racemates, they can be separated into S- and R-forms by any conventional optical resolution.

When compound (I) includes stereoisomers, both the isomers alone and mixtures of each isomer are included in the present invention.

In addition, compound (I) may be the hydrate or the non-hydrate.

Compound (I) may be labeled with an isotope (e.g., $^{3}H$, $^{14}C$, $^{35}S$ and the like) or the like.

Compound (I), a salt thereof and a prodrug thereof (hereinafter sometimes to be abbreviated as the compound of the present invention) show a GPR40 receptor function modulating action (GPR40 receptor agonist activity and GPR40 receptor antagonist activity), particularly a GPR40 receptor agonist activity, and show low toxicity and a fewer side effects (e.g., acute toxicity, chronic toxicity, genotoxicity, developmental toxicity, cardiac toxicity, drug interaction, carcinogenicity). Therefore, they are useful as safe GPR40 receptor function modulators, preferably GPR40 agonists.

A pharmaceutical agent containing the compound of the present invention has a superior GPR40 receptor function modulating action in mammals (e.g., mouse, rat, hamster, rabbit, cat, dog, bovine, sheep, monkey, human etc.), and is useful as a modulator of physiological function involving a GPR40 receptor, or as an agent for the prophylaxis or treatment of a condition or disease involving a GPR40 receptor.

To be specific, the pharmaceutical agent containing the compound of the present invention is useful as an insulin secretion modulator (preferably insulin secretagogue), a hypoglycemic drug and a pancreatic β cell protector.

Moreover, the pharmaceutical agent containing the compound of the present invention is useful as an agent for the prophylaxis or treatment of diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder, depression, depression and mania, schizophrenia, attention deficit hyperactivity disorder, visual disorder, appestat disorder (e.g., hyperorexia etc.), obesity, hypoglycemia, hypertension, edema, insulin resistance, unstable diabetes, fatty atrophy, insulin allergy, insulinoma, lipotoxicity, pancreatic fatigue, hyperinsulinemia, cancers (e.g., breast cancer etc.), metabolic syndrome, immune diseases (e.g., immunodeficiency etc.), inflammatory disease (e.g., enteritis, arthritis, allergy etc.), multiple sclerosis, acute kidney failure and the like; particularly, diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder and the like. Here, diabetes includes type 1 diabetes, type 2 diabetes and gestational diabetes can be mentioned. In addition, hyperlipidemia includes hypertriglyceridemia, hypercholesterolemia, hypoHDL-emia, postprandial hyperlipidemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic β cell in the same manner as a sulfonylurea compound, though it does not have a sulfonylurea skeleton, such as glinide compounds (e.g., repaglinide, senaglinide, nateglinide, mitiglinide or calcium salt hydrates thereof etc.), and the like, can be mentioned.

The pharmaceutical agent comprising the compound of the present invention shows low toxicity and can be safely administered orally or parenterally (e.g., topical, rectal, intravenous administration etc.) in the form of the compound of the present invention as it is or after admixing with a pharmacologically acceptable carrier to give a pharmaceutical preparation according to a method known per se used for the general production method for pharmaceutical preparations.

The preparations form of the aforementioned pharmaceutical preparation is, for example, an oral agent such as tablets (inclusive of sublingual tablets and orally disintegrable tablets), capsules (inclusive of soft capsules and microcapsules), granules, powders, troches, syrups, emulsions, suspensions and the like; or a parenteral agent such as injections (e.g., subcutaneous injections, intravenous injections, intramuscular injections, intraperitoneal injections, drip infusions etc.), external agents (e.g., transdermal preparations, ointments etc.), suppositories (e.g., rectal suppositories, vaginal suppositories etc.), pellets, nasal preparations, pulmonary preparations (inhalations), ophthalmic preparations and the like.

These agents may be controlled-release preparations such as rapid-release preparations and sustained-release preparations (e.g., sustained-release microcapsules).

The content of the compound of the present invention in a pharmaceutical preparation of the present invention is about 0.01 to about 100% by weight relative to the whole preparation. The dose of the compound of the present invention varies depending on administration subjects, administration route, diseases, condition and the like. When the compound is orally administered to an adult patient with diabetes (body weight about 60 kg), the dose is about 0.01 to about 30 mg/kg body weight per day, preferably about 0.1 to about 20 mg/kg body weight per day, more preferably about 1 to about 20 mg/kg body weight per day, which may be given at once or several portions a day.

Various organic or inorganic carriers conventionally used as materials for pharmaceutical preparations are used as the aforementioned pharmacologically acceptable carrier, which includes excipient, lubricant, binder and disintegrant for solid preparations; and solvent, dissolution aids, suspending agent, isotonicity agent, buffer and soothing agent and the like for liquid preparations. Where necessary, additives such as preservative, antioxidant, coloring agent, sweetening agent, adsorbing agent, wetting agent and the like can be used.

As the excipient, for example, lactose, sucrose, D-mannitol, starch, corn starch, crystalline cellulose, light silicic anhydride and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like can be mentioned.

As the disintegrant, for example, starch, carboxymethylcellulose, carboxymethylcellulose calcium, sodium carboxymethylstarch, L-hydroxypropylcellulose and the like can be mentioned.

As the solvent, for example, water for injection, alcohol, propylene glycol, macrogol, sesame oil, corn oil, olive oil and the like can be mentioned.

As the dissolution aids, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As an isotonicity agent, for example, glucose, D-sorbitol, sodium chloride, glycerin, D-mannitol and the like can be mentioned.

As the buffer, for example, buffers such as phosphate, acetate, carbonate, citrate and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

As the coloring agent, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment, and the like), natural pigments (e.g., β-carotene, chlorophil, red iron oxide etc.) and the like can be mentioned.

As the sweetening agent, for example, saccharin sodium, dipotassium glycyrrhizinate, aspartame, stevia and the like can be mentioned.

The compound of the present invention can be used in combination with drugs such as a therapeutic agent of diabetes, a therapeutic agent of diabetic complications, a therapeutic agent of hyperlipidemia, an antihypertensive agent, an antiobestic agent, a diuretic, a chemotherapeutic agent, an immunotherapeutic agent, an antiinflammatory drug, an antithrombotic agent, a therapeutic agent of osteoporosis, a vitamin, an antidementia agent, a therapeutic agent for incontinentia or pollakiuria, a therapeutic agent for dysurea and the like (hereinafter to be referred to as drug X).

As the therapeutic agent for diabetes, insulin preparations (e.g., animal insulin preparations extracted from the pancreas of bovine and pig; human insulin preparations genetically synthesized using *Escherichia coli* or yeast; zinc insulin; protamine zinc insulin; fragment or derivative of insulin (e.g., INS-1 etc.), oral insulin preparation and the like), insulin sensitizers (e.g., Pioglitazone or a salt thereof (preferably hydrochloride), Rosiglitazone or a salt thereof (preferably maleate), Reglixane (JTT-501), Netoglitazone (MCC-555), GI-262570, FK-614, Rivoglitazone (CS-011), Muraglitazar (BMS-298585), compounds described in WO99/58510 (e.g., (E)-4-[4-(5-methyl-2-phenyl-4-oxazolylmethoxy)benzyloxyimino]-4-phenylbutyric acid etc.), compounds described in WO01/38325, Tesaglitazar (AZ-242), BM-13-1258, LM-4156, MBX-102, LY-519818, MX-6054, LY-510929, Balaglitazone (NN-2344), T-131 or a salt thereof, THR-0921 etc.), α-glucosidase inhibitors (e.g., voglibose, acarbose, miglitol, emiglitate etc.), biguanides (e.g., phenformin, metformin, buformin or salts thereof (e.g., hydrochloride, fumarate, succinate) etc.), insulin secretagogues [sulfonylureas (e.g., tolbutamide, glibenclamide, gliclazide, chlorpropamide, tolazamide, acetohexamide, glycopyramide, glimepiride etc.), repaglinide, senaglinide, mitiglinide or calcium salt hydrate thereof, nateglinide, etc.], GLP-1 receptor agonists [e.g., GLP-1, GLP-1MR agent, NN-2211, AC-2993 (exendin-4), BIM-51077, Aib(8,35)hGLP-1(7,37)NH$_2$, CJC-1131 etc.], dipeptidyl peptidase IV inhibitors (e.g., NVP-DPP-278, PT-100, P32/98, P93/01, NVP-DPP-728, LAF237, TS-021 etc.), β3 agonists (e.g., CL-316243, SR-58611-A, UL-TG-307, AJ-9677, AZ40140 etc.), amylin agonists (e.g., pramlintide etc.), phosphotyrosine phosphatase inhibitors (e.g., sodium vanadate etc.), gluconeogenesis inhibitors (e.g., glycogen phosphorylase inhibitor, glucose-6-phosphatase inhibitor, glucagon antagonist etc.), SGLT (sodium-glucose cotransporter) inhibitors (e.g., T-1095 etc.), 11β-hydroxysteroid dehydrogenase inhibitors (e.g., BVT-3498 etc.), adiponectin or agonist thereof, IKK inhibitors (e.g., AS-2868 etc.), leptin resistance improving drugs, somatostatin receptor agonists (compounds described in WO01/25228, WO03/42204, WO98/44921, WO98/45285, WO99/22735, etc.), glucokinase activators (e.g., Ro-28-1675 etc.) and the like can be mentioned.

Examples of the therapeutic agent for diabetic complications include aldose reductase inhibitors (e.g., Tolrestat, Epalrestat, Zenarestat, Zopolrestat, Fidarestat (SNK-860), AS-3201, Minalrestat (ARI-509), CT-112 etc.), neurotrophic factors and increasing drugs thereof (e.g., NGF, NT-3, BDNF, neurotrophin production-secretion promoters described in WO01/14372 (e.g., 4-(4-chlorophenyl)-2-(2-methyl- 1-imidazolyl)-5-[3 -(2-methylphenoxy) propyl]oxazole etc.) and the like), protein kinase C (PKC) inhibitors (e.g., ruboxistaurin mesylate; LY-333531 etc.), AGE inhibitors (e.g., ALT-945, pimagedine, pyratoxanthine, N-phenacylthiazolium bromide (ALT-766), EXO-226, ALT-711, Pyridorin, Pyridoxamine etc.), active oxygen scavengers (e.g., thioctic acid etc.), cerebral vasodilators (e.g., tiapride etc.), somatostatin receptor agonists (BIM23190), apoptosis signal regulating kinase-1 (ASK-1) inhibitors and the like.

Examples of the therapeutic agent of hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt, calcium salt) etc.), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid etc.), fibrate compounds (e.g., bezafibrate, clofibrate, simfibrate, clinofibrate etc.), antioxidants (e.g., lipoic acid, probucol etc.) and the like.

Examples of the antihypertensive agent include angiotensin converting enzyme inhibitors (e.g., captopril, enalapril, delapril etc.), angiotensin II receptor antagonists (e.g., losartan, candesartan cilexetil, eprosartan, valsartan, telmisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium channel blockers (e.g., manidipine, nifedipine, amlodipine, efonidipine, nicardipine etc.), Clonidine and the like.

Examples of the antiobestic agent include antiobestic agents acting on the central nervous system (e.g., Dexfenfluramine, fenfluramine, phentermine, Sibutramine, amfepramone, dexamphetamine, Mazindol, phenylpropanolamine, clobenzorex; MCH receptor antagonists (e.g., SB-568849; SNAP-7941; compounds encompassed in WO01/82925 and WO01/87834 etc.); neuropeptide Y antagonists (e.g., CP-422935 etc.); cannabinoid receptor antagonists (e.g., SR-141716, SR-147778 etc.); ghrelin antagonists; 11β-hydroxysteroid dehydrogenase inhibitors (e.g., BVT-3498 etc.) and the like), pancreatic lipase inhibitors (e.g., orlistat, ATL-962 etc.), β3 agonists (e.g., CL-316243, SR-58611-A, UL-TG-307, AJ-9677, AZ40140 etc.), peptidic anorexiants (e.g., leptin, CNTF (Ciliary Neurotropic Factor) etc.), cholecystokinin agonists (e.g., lintitript, FPL-15849 etc.), feeding deterrents (e.g., P-57 etc.) and the like.

Examples of the diuretic include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agent include alkylation agents (e.g., cyclophosphamide, ifosfamide etc.), metabolic antagonists (e.g., methotrexate, 5-fluorouracil or its derivative, etc.), anti-cancer antibiotics (e.g., mitomycin, adriamycin etc.), plant-derived anti-cancer agents (e.g., vincristin, vindesine, taxol etc.), cisplatin, carboplatin, etoposide and the like. Of these, furtulon and neofurtulon, which are 5-fluorouracil derivatives, and the like are preferable.

Examples of the immunotherapeutic agent include microorganism or bacterial components (e.g., muramyl dipeptide derivative, picibanil etc.), polysaccharides having immunity potentiating activity (e.g., lentinan, sizofuran, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like.

As the antiinflammatory drug, for example, non-steroidal antiinflammatory agents such as aspirin, acetoaminofen, indomethacin and the like can be mentioned.

Examples of the antithrombotic agent include heparins (e.g., heparin sodium, heparin calcium, dalteparin sodium etc.), warfarins (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the therapeutic agent of osteoporosis include alfacalcidol, calcitriol, elcatonin, calcitonin salmon, estriol, ipriflavone, pamidronate disodium, alendronate sodium hydrate, incadronate disodium, risedronate disodium, and the like.

As the vitamin, for example, vitamin $B_1$, vitamin $B_{12}$ and the like can be mentioned.

Examples of the antidementia agent include tacrine, donepezil, rivastigmine, galanthamine and the like.

Examples of the therapeutic agent for incontinentia or pollakiuria include flavoxate hydrochloride, oxybutynin hydrochloride, propiverine hydrochloride and the like.

Examples of the therapeutic agent for dysurea include acetylcholine esterase inhibitors (e.g., distigmine) and the like.

Furthermore, drugs having a cachexia-improving action established in animal models and clinical situations, such as cyclooxygenase inhibitors (e.g., Indometacin etc.), Progesterone derivatives (e.g., Megesterol acetate etc.), glucosteroid (e.g., dexamethasone etc.), metoclopramide agents, tetrahydrocannabinol agents, fat metabolism improving agents (e.g., eicosapentaenoic acid etc.), growth hormones, IGF-1, or antibodies to a cachexia-inducing factor such as TNF-α, LIF, IL-6, Oncostatin M and the like, can be used in combination with the compound of the present invention.

Further, glycosylation inhibitors (e.g., ALT-711, etc.), nerve regeneration promoting drugs (e.g., Y-128, VX853, prosaptide, etc.), antidepressants (e.g., desipramine, amitriptyline, imipramine, etc.), anticonvulsants (e.g., lamotrigine, Trileptal, Keppra, Zonegran, Pregabalin, Harkoseride, carbamazepine etc.), antiarrhythmic drugs (e.g., mexiletine etc.), acetylcholine receptor ligands (e.g., ABT-594 etc.), endothelin receptor antagonists (e.g., ABT-627 etc.), monoamine uptake inhibitors (e.g., tramadol etc.), narcotic analgesics (e.g., morphine etc.), GABA receptor agonists (e.g., gabapentin, gabapentin MR agent etc.), $\alpha_2$ receptor agonists (e.g., clonidine etc.), local analgesics (e.g., capsaicin etc.), antianxiety drugs (e.g., benzothiazepines etc.), phosphodiesterase inhibitors (e.g., sildenafil etc.), dopamine receptor agonists (e.g., apomorphine etc.) and the like can also be used in combination with the compound of the present invention.

Two or more kinds of the above-mentioned drug X may be used in an appropriate combination.

By combining the compound of the present invention with a drug X, a superior effect such as (1) the dose of the compound of the present invention or a drug X can be reduced as compared to single administration of the compound of the present invention or a drug X, (2) the period of treatment can be set longer by selecting a drug X having different action and mechanism from those of the compound of the present invention, (3) a sustained treatment effect can be designed by selecting a drug X having different action and mechanism from those of the compound of the present invention, (4) a synergistic effect can be afforded by a combined use of the compound of the present invention and a drug X, and the like, can be achieved.

When the compound of the present invention and a drug X are used in combination, the administration time of the compound of the present invention and the drug X is not restricted, and the compound of the present invention and the drug X can be administered to an administration subject simultaneously, or may be administered at staggered times. The dosage of the drug X may be determined according to the dose clinically used, and can be appropriately selected depending on an administration subject, administration route, disease, combination and the like.

The administration mode of the compound of the present invention and a drug X is not particularly restricted, as long as the compound of the present invention and the drug X are combined in administration. Examples of such administration mode include the following methods: (1) The compound of the present invention and the drug X are simultaneously formulated to give a single preparation which is administered. (2) The compound of the present invention and the drug X are separately formulated to give two kinds of preparations which are administered simultaneously by the same administration route. (3) The compound of the present invention and the drug X are separately formulated to give two kinds of preparations which are administered by the same administration route at staggered times. (4) The compound of the present invention and the drug X are separately formulated to give two kinds of preparations which are administered simultaneously by the different administration routes. (5) The compound of the present invention and the drug X are separately formulated to give two kinds of preparations which are administered by the different administration routes at staggered times (for example, the compound of the present invention and the drug X are administered in this order, or in the reverse order), and the like.

A compound of the formula (I) wherein E is —$CH_2$—N($C_{1-6}$ alkyl group)-, —N($C_{1-6}$ alkyl group)-$CH_2$—, —S—CH($C_{1-6}$ alkyl group)- or —$CH_2$—CH($C_{1-6}$ alkyl group)- or a salt thereof, and a compound of the formula (I) wherein X is S, ring $S^1$ is a pyridine ring optionally further having substituent(s) selected from an optionally substituted $C_{1-6}$ alkyl group, an optionally substituted $C_{1-6}$ alkoxy group and a halogen atom, E is —$W^1$—N($R^5$)—$W^2$—, —$W^1$—CH($R^6$)—O—$W^2$—, —$W^1$—O—CH($R^6$)—$W^2$—, —$W^1$—S(O)n-$W^2$— or —$W^1$—CH($R^6$)—$W^2$— ($W^1$ and $W^2$ are the same or different and each is a bond or an optionally substituted $C_{1-3}$ alkylene group, $R^5$ and $R^6$ are $C_{1-6}$ alkyl groups and n is 1 or 2 or a salt thereof can be produced or processed into a preparation in the same manner as above, and can be used for mammals as a GPR40 receptor function modulator, an agent for the prophylaxis or treatment of diabetes, and the like.

EXAMPLES

The present invention is further explained in detail by referring to the following Reference Examples, Examples, Formulation Examples and Experimental Example, which are mere working examples not to be construed as limitative of the present invention and may be changed without departing from the scope of the present invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. that could not be confirmed due to broad peak by proton NMR spectrum are not included in the data.

The other symbols used herein mean the following:

s: singlet d: doublet t: triplet q: quartet m: multiplet br: broad

J: coupling constant

Hz: Hertz $CDCl_3$: deuterated chloroform $^1$H NMR: proton nuclear magnetic resonance In the following Reference Examples and Examples, mass spectrum (MS) was measured under the following conditions.

measurement tools: Waters Corporation ZMD, Waters Corporation ZQ2000 or Micromass Ltd., platform II.

ionization method: Electron Spray Ionization (ESI) or Atmospheric Pressure Chemical Ionization (APCI). Unless specifically indicated, ESI was used.

In Examples, purification by preparative HPLC was performed under the following conditions.

preparative HPLC tools: Gilson, Inc., high through-put purification system column: YMC Combiprep ODS-A S-5 μm, 20×50 mm solvent:
    Solution A; 0.1% trifluoroacetic acid-containing water,
    Solution B; 0.1% trifluoroacetic acid-containing acetonitrile gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10).

gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).

flow rate: 25 ml/min, detection method: UV 220 nm

In the present specification, the melting point is that measured using, for example, micromelting point measuring apparatus (Yanako, MP-500D or Buchi, B-545) or DSC (differential scanning calorimeter) apparatus (SEIKO, EXSTAR6000) and the like.

In general, melting points sometimes vary depending on measurement apparatuses, measurement conditions and the like. The crystal in the present specification may show a different melting point from that described in the present specification, as long as it is within general error range.

Reference Example 1

4-isopropyl-N-(2-phenylethyl)-1,3-thiazole-2-amine

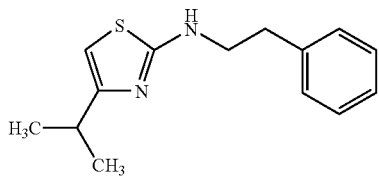

To a solution of 3-methyl-2-butanone (0.86 g) in methanol (10 mL) was added bromine (1.60 g) at −30° C. The mixture was allowed to warm to room temperature and stirred until the red color of bromine disappeared. To the obtained colorless solution were added sodium acetate (1.60 g) and N-(2-phenylethyl)thiourea (1.80 g) and the mixture was stirred with heating under reflux for 4 hr. A saturated aqueous sodium hydrogencarbonate solution (10 mL) was added to the reaction mixture and the mixture was concentrated. The residue was purified by silica gel chromatography (ethyl acetate: hexane=1:9-2:1 in volume ratio) to give the title compound (1.26 g, yield 51%) as colorless crystals.

MS: m/z 247 (M+H).

Reference Example 2

N-[2-(4-fluorophenyl)ethyl]-4-isopropyl-1,3-thiazole-2-amine

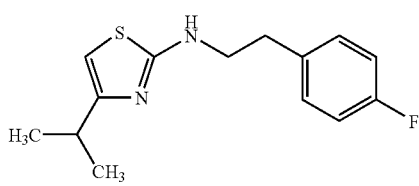

The title compound was synthesized in the same manner as in Reference Example 1 from N-[2-(4-fluorophenyl)ethyl]-thiourea (yield 52%). Colorless crystals.

MS: m/z 265 (M+H).

Reference Example 3

4-isopropyl-N-(2-pyridin-2-ylethyl)-1,3-thiazole-2-amine

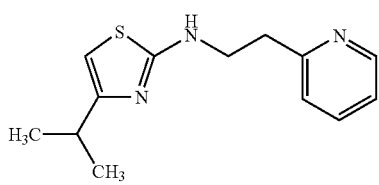

The title compound was synthesized in the same manner as in Reference Example 1 from N-(2-pyridin-2-ylethyl)thiourea (yield 51%). A yellow oil.

$^1$H NMR (300 MHz, CDCl$_3$) δppm 1.22(6H, d, J=6.8 Hz), 2.76-2.89(1H, m), 3.12(2H, t, J=6.4 Hz), 3.65(2H, q, J=6.1 Hz), 5.71(1H, s), 5.99-6.09(1H, m), 7.11-7.20(2H, m), 7.57-7.65(1H, m), 8.52-8.57(1H, m).

Reference Example 4

N-[2-(2-fluorophenyl)ethyl]-4-isopropyl-1,3-thiazole-2-amine

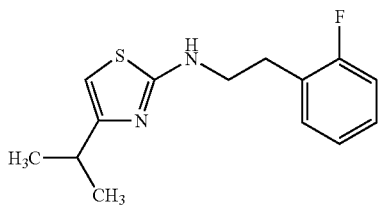

The title compound was synthesized in the same manner as in Reference Example 1 from N-[2-(2-fluorophenyl)ethyl]-thiourea (yield 4%). Yellow solid.

$^1$H NMR (300 MHz, CDCl$_3$) δppm 1.23(6H, d, J=7.0 Hz), 2.75-2.90(1H, m), 3.00(2H, t, J=7.0 Hz), 3.50(2H, q, J=6.8 Hz), 5.11(1H, s), 6.07(1H, d, J=0.8 Hz), 6.96-7.13(2H, m), 7.17-7.25(2H, m).

Reference Example 5

4-isobutyl-N-(2-phenylethyl)-1,3-thiazole-2-amine

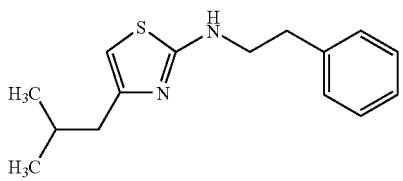

To a solution of 4-methyl-2-pentanone (2.00 g) in methanol (10 mL) was added bromine (3.20 g) at −30° C. The mixture was allowed to warm to room temperature and stirred until the red color of bromine disappeared. To the obtained colorless solution were added sodium acetate (3.20 g) and N-(2-phenylethyl)thiourea (1.80 g) and the mixture was stirred with heating under reflux for 4 hr. A saturated aqueous sodium hydrogencarbonate solution (10 mL) was added to the reaction mixture and the mixture was concentrated. The residue was purified by silica gel column chromatography (ethyl acetate:hexane=1:9-2:1 in volume ratio) to give the title compound (1.15 g, yield 41%) as pale-yellow crystals.

MS: m/z 261 (M+H).

Reference Example 6

N-[2-(4-fluorophenyl)ethyl]-4-isobutyl-1,3-thiazole-2-amine

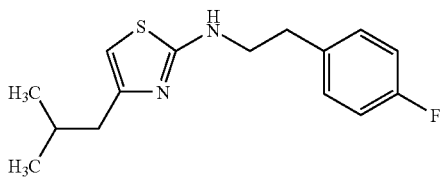

The title compound was synthesized in the same manner as in Reference Example 5 from N-[2-(4-fluorophenyl)ethyl]-thiourea (yield 42%). Colorless crystals.

MS: m/z 279 (M+H).

Reference Example 7

N-(2-phenylethyl)-4-propyl-1,3-thiazole-2-amine

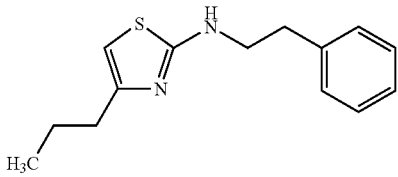

To a solution of 2-pentanone (1.72 g) in methanol (10 mL) was added bromine (3.20 g) at −30° C. The mixture was allowed to warm to room temperature and stirred until the red color of bromine disappeared. To the obtained colorless solution were added sodium acetate (3.20 g) and N-(2-phenylethyl)thiourea (2.70 g) and the mixture was stirred with heating under reflux for 4 hr. A saturated aqueous sodium hydrogencarbonate solution (10 mL) was added to the reaction mixture and the mixture was concentrated. The residue was purified by silica gel column chromatography (ethyl acetate:hexane=1:9-2:1 in volume ratio) to give the title compound (850 mg, yield 23%) as pale-yellow crystals.

MS: m/z 247 (M+H).

Reference Example 8

N-(2-phenylethyl)-4-[4-(trifluoromethyl)phenyl]-1,3-thiazole-2-amine

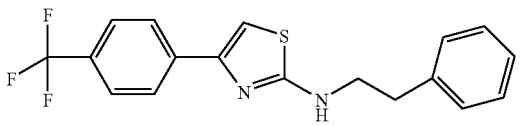

A mixture of 2-bromo-1-[4-(trifluoromethyl)phenyl]-ethanone (5.34 g), N-(2-phenylethyl)thiourea (3.60 g) and N,N-dimethylformamide (20 mL) was stirred at room temperature for 1 hr. The reaction mixture was poured into water and extracted with ethyl acetate. The ethyl acetate layer was dried over anhydrous magnesium sulfate and concentrated to give the title compound (5.20 g, yield 74%) as colorless crystals.

MS: m/z 349 (M+H).

Reference Example 9 methyl 3-(4-{[4-(chloromethyl)benzyl]oxy}-phenyl)propanoate

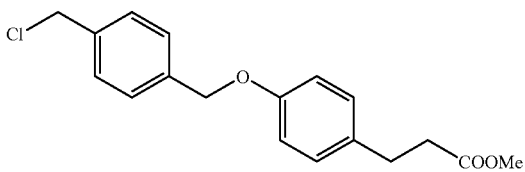

4-(Chloromethyl)benzyl alcohol (4.68 g), methyl 3-(4-hydroxyphenyl)propanoate (5.40 g) and triphenylphosphine (9.20 g) were dissolved in a mixed solvent of toluene (60 mL)-tetrahydrofuran (30 mL), cooled to 0° C. and diethyl azodicarboxylate (40% toluene solution, 15.2 g) was added dropwise with stirring. After completion of the dropwise addition, the reaction mixture was allowed to warm to room temperature and further stirred for 1 hr. The reaction mixture was concentrated and the residue was purified by silica gel column chromatography (ethyl acetate:hexane=1:19-1:1 in volume ratio) to give the title compound (5.19 g, yield 54%) as colorless crystals.

$^1$H NMR (300 MHz, CDCl$_3$) δ: 2.59(2H, t, J=7.7 Hz), 2.89(2H, t, J=7.7 Hz), 3.66(3H, s), 4.59(2H, s), 5.04(2H, s), 6.89(2H, d, J=8.7 Hz), 7.11(2H, d, J=8.7 Hz), 7.35-7.45(4H, m).

Reference Example 10 ethyl 3-(4-{[4-(chloromethyl)benzyl]oxy}-2-fluorophenyl)propanoate

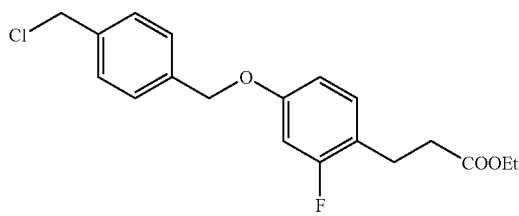

The title compound was synthesized in the same manner as in Reference Example 9 from ethyl 3-(2-fluoro-4-hydroxyphenyl)propanoate (yield 73%). Colorless crystals.

$^1$H NMR (300 MHz, CDCl$_3$) δppm 1.23(3H, t, J=7.1 Hz), 2.58(2H, t, J=7.6 Hz), 2.90(2H, t, J=7.6 Hz), 4.12(2H, q, J=7.1 Hz), 4.60(2H, s), 5.02(2H, s), 6.62-6.70(2H, m), 7.10 (1H, t, J=8.8 Hz), 7.41(4H, s).

Reference Example 11

N-[3-(methylthio)propyl]-4-phenyl-1,3-thiazole-2-amine

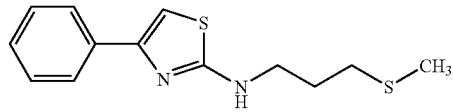

A mixture of 2-bromo-1-phenylethanone (1.99 g), N-[3-(methylthio)propyl]thiourea (1.64 g) and N,N-dimethylformamide (5 mL) was stirred at room temperature for 1 hr. The reaction mixture was poured into water and extracted with ethyl acetate. The ethyl acetate layer was dried over anhydrous magnesium sulfate and concentrated to give the title compound (1.85 g, yield 70%) as a yellow oil.

$^1$H NMR (300 MHz, CDCl$_3$) δppm 1.95-2.06(2H, m), 2.13 (3H, s), 2.63(2H, t, J=7.1 Hz), 3.4-3.5(2H, m), 5.78(1H, s), 6.69(1H, s), 7.29-7.49(3H, m), 7.69-7.86(2H, m).

Reference Example 12

N-(2-phenylethyl)-4-pyridin-2-yl-1,3-thiazole-2-amine

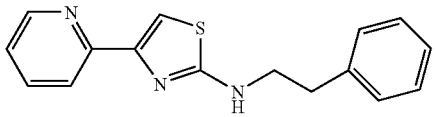

A mixture of 2-bromo-1-pyridin-2-ylethanone hydrobromide (4.00 g), N-(2-phenylethyl)thiourea (3.60 g), sodium acetate (1.60 g) and ethanol (30 mL) was stirred with heating under reflux for 1 hr. After cooling, the reaction mixture was poured into water, and the mixture was extracted with ethyl acetate. The ethyl acetate layer was dried over anhydrous magnesium sulfate, and concentrated. The residue was purified by silica gel column chromatography (ethyl acetate:hexane=1:9-2:1 in volume ratio) to give the title compound (2.71 g, yield 48%) as a yellow oil.

MS: m/z 282 (M+H).

Reference Example 13

(4-{[(4-phenyl-1,3-thiazol-2-yl)(2-pyridin-2-ylethyl)amino]methyl}phenyl)methanol

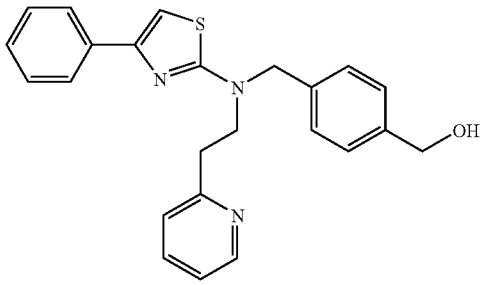

A mixture of 2-bromo-1-phenylethanone (1.0 g), N-(2-pyridin-2-ylethyl)thiourea (0.90 g) and N,N-dimethylformamide (5 mL) was stirred at room temperature for 1 hr. Sodium hydride (60% in oil, 400 mg) was added to the reaction mixture and the mixture was further stirred at room temperature for 1 hr. Methyl 4-(bromomethyl)benzoate (1.15 g) was added to the reaction mixture under ice-cooling, and the mixture was allowed to warm to room temperature and further stirred for 1 hr. The reaction mixture was poured into aqueous sodium dihydrogenphosphate solution and extracted with ethyl acetate. The ethyl acetate layer was dried over anhydrous magnesium sulfate, and concentrated. The residue was purified by silica gel column chromatography (ethyl acetate:hexane=1:9-2:1 in volume ratio) to give a yellow oil. The yellow oil was dissolved in tetrahydrofuran (30 mL) and lithium aluminum hydride (120 mg) was added by small portions under ice-cooling. The reaction mixture was stirred under ice-cooling for 30 min and sodium sulfate 10 hydrate (1.0 g) was added. The mixture was allowed to warm to room temperature and stirred for 30 min. The resulting precipitate was filtered off and the filtrate was concentrated to give the title compound (890 mg, yield 44%) as a yellow oil.

$^1$H NMR (300 MHz, CDCl$_3$) δppm 1.66(1H, t, J=5.9 Hz), 3.20(2H, t, J=7.5 Hz), 3.90(2H, t, J=7.5 Hz), 4.59-4.75(4H, m), 6.72(1H, s), 7.03-7.23(2H, m), 7.22-7.33(5H, m), 7.33-7.42(2H, m), 7.53-7.68(1H, m), 7.79-7.94(2H, m), 8.54(1H, dd, J=4.1,0.8 Hz).

Reference Example 14

(4-{[[2-(4-fluorophenyl)ethyl](4-isopropyl-1,3-thiazol-2-yl)amino]methyl}phenyl)methanol

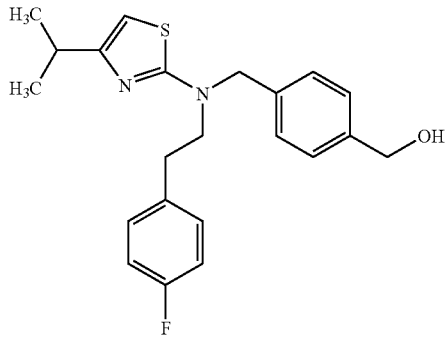

A mixture of N-[2-(4-fluorophenyl)ethyl]-4-isopropyl-1,3-thiazole-2-amine (550 mg), sodium hydride (80 mg) and N,N-dimethylformamide (5 mL) was stirred at room temperature for 1 hr. Methyl 4-(bromomethyl)benzoate (500 mg) was added to the reaction mixture under ice-cooling, and the mixture was allowed to warm to room temperature and further stirred for 1 hr. The reaction mixture was poured into 1N hydrochloric acid and extracted with ethyl acetate. The ethyl acetate layer was dried over anhydrous magnesium sulfate, and concentrated. The residue was purified by silica gel column chromatography (ethyl acetate:hexane=1:9-1:1 in volume ratio) to give a yellow oil. The yellow oil was dissolved in tetrahydrofuran (30 mL) and lithium aluminum hydride (80 mg) was added by small portions under ice-cooling. The reaction mixture was stirred under ice-cooling for 30 min and sodium sulfate 10 hydrate (1.0 g) was added. The mixture was allowed to warm to room temperature and stirred for 30 min. The resulting precipitate was filtered off and the filtrate was concentrated to give the title compound (720 mg, yield 90%) as a yellow oil.

$^1$H NMR (300 MHz, CDCl$_3$) δppm 1.26(6H, d, J=6.8 Hz), 1.61(1H, t, J=5.8 Hz), 2.83-2.94(3H, m), 3.53-3.60(2H, m), 4.56(2H, s), 4.68(2H, d, J=5.8 Hz), 6.06(1H, d, J=0.9 Hz), 6.92-6.99(2H, m), 7.08-7.15(2H, m), 7.23-7.34(4H, m).

Reference Example 15 methyl 4-[[(2-phenylethyl)(4-phenyl-1,3-thiazol-2-yl)amino]methyl]benzoate

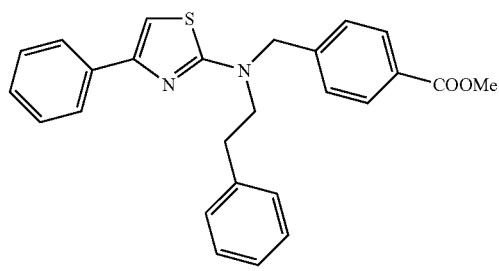

To a solution of 4-phenyl-N-(2-phenylethyl)-1,3-thiazole-2-amine (4.63 g, 16.5 mmol) in N,N-dimethylformamide (50 mL) was added 60% sodium hydride (990 mg, 24.8 mmol) and the mixture was stirred for 30 min. Methyl 4-(bromomethyl)benzoate (4.54 g, 19.8 mmol) was added and the mixture was stirred at room temperature for 2 hr. Water was added to the reaction mixture, and the mixture was extracted with ethyl acetate. The extract was washed with water and concentrated under reduced pressure. The residue was purified by silica gel column chromatography to give the title compound (3.39 g, yield 48%) as a yellow oil.

$^1$H NMR (CDCl$_3$) δ3.00(t, J=7.8 Hz, 2H), 3.69(t, J=7.8 Hz, 2H), 3.90(s, 3H), 4.71(s, 2H), 6.76(s, 1H), 7.18-7.41(m, 10H), 7.86-7.88(m, 2H), 7.98-8.00(m, 2H).

Reference Example 16

[4-[[(2-phenylethyl)(4-phenyl-1,3-thiazol-2-yl)amino]methyl]phenyl]methanol

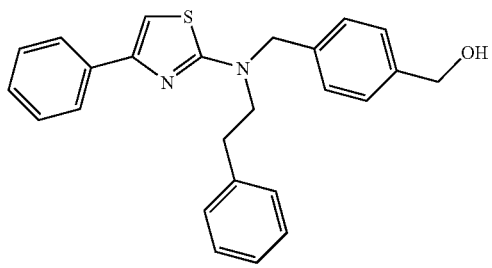

Under ice-cooling, to a solution of methyl 4-[[(2-phenylethyl)(4-phenyl-1,3-thiazol-2-yl)amino]methyl]benzoate (535 mg, 1.25 mmol) in tetrahydrofuran (20 mL) was added 1.5M diisobutyl aluminum hydride toluene solution (2.4 mL, 3.64 mmol). The mixture was stirred at room temperature for 2 hr and sodium sulfate 10 hydrate (1.29 g, 4 mmol) was added. The mixture was stirred at room temperature for 1 hr. The resulting insoluble materials were filtered off and the filtrate was concentrated. The residue was purified by silica gel column chromatography (hexane/ethyl acetate=2:3) to give the title compound (409 mg, yield 81%) as a colorless oil.

$^1$H NMR (CDCl$_3$) δ2.99(t, J=8.1 Hz, 2H), 3.68(t, J=8.1 Hz, 2H), 4.65-4.69(m, 4H), 6.74(s, 1H), 7.19-7.41(m, 12H), 7.87-7.90(m, 2H).

Reference Example 17 methyl 3-[[(2-phenylethyl)(4-phenyl-1,3-thiazol-2-yl)amino]methyl]benzoate

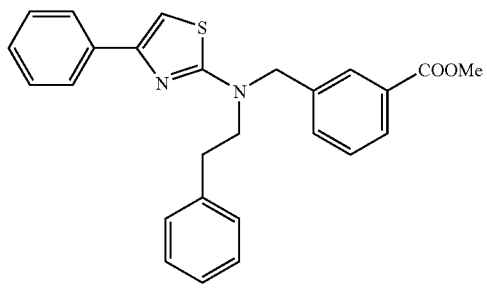

The title compound was obtained as a yellow oil from 4-phenyl-N-(2-phenylethyl)-1,3-thiazole-2-amine and methyl 3-(bromomethyl)benzoate by a method similar to the method of Reference Example 15 (yield 14%).

$^1$H NMR (CDCl$_3$) δ2.96-3.05(2H, m), 3.65-3.73(2H, m), 3.91(3H, s), 4.70(2H, s), 6.75(1H, s), 7.19-7.33(6H, m), 7.35-7.43(3H, m), 7.52(1H, d, J=7.7 Hz), 7.86-7.91(2H, m), 7.92-8.00(2H, m).

Reference Example 18

[3-[[(2-phenylethyl)(4-phenyl-1,3-thiazol-2-yl)amino]methyl]phenyl]methanol

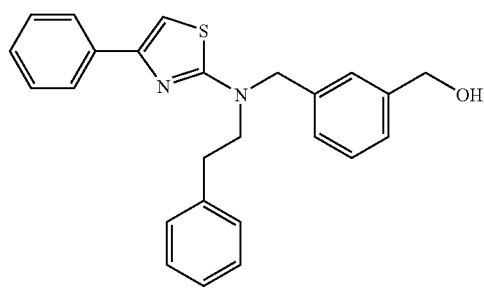

The title compound was obtained as a yellow oil from methyl 3-[[(2-phenylethyl)(4-phenyl-1,3-thiazol-2-yl)amino]methyl]benzoate by a method similar to the method of Reference Example 16 (yield 85%).

$^1$H NMR (CDCl$_3$) δ3.00(2H, t, J=8.1 Hz), 3.70(2H, t, J=8.1 Hz), 4.61-4.72(4H, m), 6.74(1H, s), 7.15-7.34(10H, m), 7.39 (2H, t, J=7.4 Hz), 7.82-7.94(2H, m).

Reference Example 19

2-hydroxy-1-phenylpropan-1-one

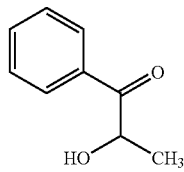

To a solution of 2-bromo-1-phenylpropan-1-one (6.0 g, 28.2 mmol) in methanol (50 mL) was added sodium formate (7.66 g, 113 mmol) and the mixture was heated under reflux for 8 hr. Water was added to the reaction mixture, and the mixture was extracted with ethyl acetate. The extract was washed with water and concentrated under reduced pressure. The residue was purified by silica gel column chromatography (hexane/ethyl acetate=4:1) to give the title compound (2.66 g, yield 63%) as a colorless oil.

$^1$H NMR (CDCl$_3$) δ7.96-7.92(m, 2H), 7.66-7.60(m, 1H), 7.54-7.49(m, 2H), 5.21-5.12(m, 1H), 3.78(d, 1H, J=6.2 Hz), 1.45(d, 3H, J=7.0 Hz).

Reference Example 20

5-methyl-4-phenyl-1,3-oxazol-2(3H)-one

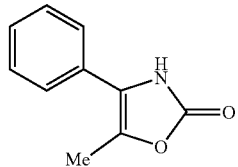

To a solution of 2-hydroxy-1-phenylpropan-1-one (1.00 g, 6.66 mmol) and potassium cyanate (1.08 g, 13.3 mmol) in 2-propanol (15 mL) was added dropwise acetic acid (960 mg, 16.0 mmol) at 50° C. over 1 hr. The mixture was stirred at 50° C. for 5 hr, and the reaction mixture was poured into water. The resulting precipitate was collected by filtration and recrystallized from isopropyl ether-hexane to give the title compound (430 mg, yield 37%) as white crystals.

MS: m/z 176 (M+H).

Reference Example 21

2-chloro-5-methyl-4-phenyl-1,3-oxazole

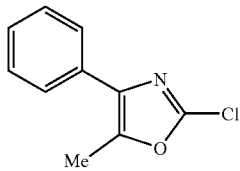

To a suspension of 5-methyl-4-phenyl-1,3-oxazol-2(3H)-one (430 mg, 2.45 mmol) in phosphorus oxychloride (2.36 g, 14.7 mmol) was added pyridine (194 mg, 2.45 mmol) and the mixture was stirred at 120° C. for 2 hr. The reaction mixture was diluted with acetonitrile and added dropwise to water (about 30° C.). The organic materials were extracted with ethyl acetate, washed with saturated brine, dried over anhydrous magnesium sulfate, and concentrated under reduced pressure. The residue was purified by silica gel column chromatography (hexane/ethyl acetate=7:3) to give the title compound (233 mg, yield 49%) as a yellow oil.

MS: m/z 194 (M+H).

Reference Example 22

5-methyl-4-phenyl-N-propyl-1,3-oxazole-2-amine

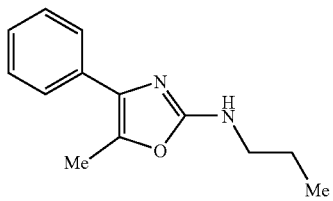

To a solution of 2-chloro-5-methyl-4-phenyl-1,3-oxazole (1.46 g, 7.56 mmol) in ethanol (15 mL) was added propylamine (5 mL), and the mixture was stirred in a sealed tube at 110° C. for 8 hr. The reaction mixture was concentrated and water was added. The mixture was extracted with ethyl acetate, washed with saturated brine, dried over anhydrous magnesium sulfate, and concentrated under reduced pressure. The residue was purified by silica gel column chromatography (hexane/ethyl acetate=2:1) to give the title compound (850 mg, yield 52%) as a yellow powder.

MS: m/z 217 (M+H).

Reference Example 23 ethyl(2E)-3-(2-fluoro-4-methoxyphenyl)acrylate

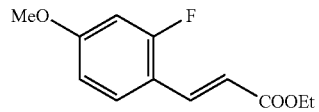

To an ice-cooled solution of ethyl diethylphosphonoacetate (9.45 g, 42.1 mmol) in tetrahydrofuran (50 mL) was added 60% sodium hydride (1.54 g, 38.5 mmol) and the mixture was stirred for 15 min. A solution of 2-fluoro-4-methoxybenzaldehyde (5.00 g, 32.4 mmol) in tetrahydrofuran (30 mL) was added dropwise. The mixture was stirred at room temperature for 2 hr and water was added. The mixture was extracted with ethyl acetate. The extract was washed with saturated brine, dried over anhydrous magnesium sulfate and concentrated under reduced pressure. The residue was purified by silica gel column chromatography (hexane/ethyl acetate=4:1) to give the title compound (7.07 g, yield 97%) as a colorless oil.

$^1$H NMR (CDCl$_3$) δ1.33(3H, t, J=7.1 Hz), 3.83(3H, s), 4.26(2H, q, J=7.1 Hz), 6.41(1H, d, J=16.2 Hz), 6.61-6.73(2H, m), 7.45(1H, t, J=8.6 Hz), 7.75(1H, d, J=16.2 Hz).

Reference Example 24 ethyl 3-(2-fluoro-4-methoxyphenyl)propanoate

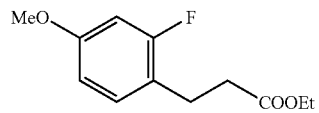

A mixture of ethyl (2E)-3-(2-fluoro-4-methoxyphenyl)acrylate (7.07 g, 31.5 mmol), tetrahydrofuran (50 mL), ethanol (5 mL) and platinum dioxide (300 mg) was stirred overnight under a hydrogen atmosphere at room temperature. The catalyst was filtered off and the filtrate was concentrated. The residue was purified by silica gel column chromatography (hexane/ethyl acetate=4:1) to give the title compound (5.97 g, yield 84%) as a colorless oil.

$^1$H NMR (CDCl$_3$) δ1.23(3H, t, J=7.2 Hz), 2.58(2H, t, J=7.6 Hz), 2.90(2H, t, J=7.6 Hz), 3.77(3H, s), 4.12(2H, q, J=7.2 Hz), 6.57-6.63(2H, m), 7.07-7.13(1H, m).

Reference Example 25 ethyl 3-(2-fluoro-4-hydroxyphenyl)propanoate

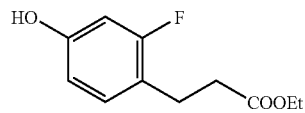

To a solution of ethyl 3-(2-fluoro-4-methoxyphenyl)propanoate (57.4 g, 254 mmol) and aluminum chloride (101 g, 761 mmol) in dichloromethane (250 mL) was added dropwise 1-octanethiol (74.3 g, 508 mmol) and the mixture was stirred at room temperature for 2 hr. The reaction mixture was poured into ice water and the mixture was stirred for 30 min. The organic layer was separated, washed with saturated brine, dried over anhydrous magnesium sulfate and concentrated under reduced pressure. The residue was purified by silica gel column chromatography (hexane/ethyl acetate=4:1) to give the title compound (44.6 g, yield 83%) as a colorless oil.

$^1$H NMR (CDCl$_3$) δ1.23(3H, t, J=7.2 Hz), 2.58(2H, t, J=8.1 Hz), 2.89(2H, t, J=8.1 Hz), 4.12(2H, q, J=7.2 Hz), 6.51-6.56 (2H, m), 7.01-7.06(1H, m).

Reference Example 26 ethyl (2E)-3-(2,6-difluoro-4-methoxyphenyl)acrylate

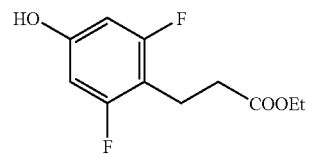

A solution of ethyl diethylphosphonoacetate (2.34 g, 10.4 mmol) and 60% sodium hydride (0.38 g, 9.50 mmol) in tetrahydrofuran (40 mL) was stirred under ice-cooling for 10 min. Thereto was added 2,6-difluoro-4-methoxybenzaldehyde (1.5 g, 8.71 mmol) and the mixture was stirred for 4 hr while allowing to warm to room temperature. The reaction solution was diluted with ethyl acetate, washed successively with aqueous citric acid solution, water and aqueous sodium chloride solution, dried over magnesium sulfate, and concentrated under reduced pressure. The obtained residue was purified by silica gel chromatography (ethyl acetate:hexane=1:10-1:5) to give the title compound (1.1 g, yield 52%) as colorless needles.

MS: m/z 243 (M+H).

Reference Example 27 ethyl 3-(2,6-difluoro-4-methoxyphenyl)propanoate

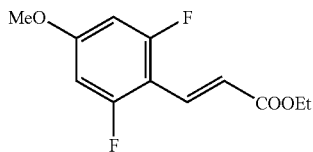

Ethyl(2E)-3-(2,6-difluoro-4-methoxyphenyl)acrylate (1.1 g, 4.54 mmol) was dissolved in a mixed solvent of tetrahydrofuran (30 mL) and ethanol (30 mL), 10% palladium-carbon (0.30 g) was added and the mixture was stirred under a hydrogen atmosphere at room temperature for 5 hr. The catalyst was filtered off, and the obtained filtrate was concentrated to give the title compound (1.17 g, yield 100%) as a colorless oil.

MS: m/z 245 (M+H).

Reference Example 28 ethyl 3-(2,6-difluoro-4-hydroxyphenyl)propanoate

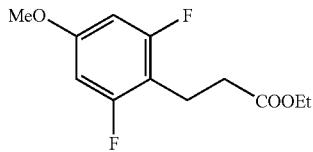

A solution of ethyl 3-(2,6-difluoro-4-methoxyphenyl)propanoate (1.17 g, 4.79 mmol), aluminum chloride (1.9 g, 14.2 mmol) and 1-octanethiol (1.7 mL, 9.80 mmol) in dichloromethane (20 mL) was stirred from under ice-cooling to room temperature for 4 hr. The reaction mixture was poured into ice water, and the mixture was stirred for 1 hr. The mixed solution was extracted with dichloromethane, washed with saturated brine, dried over anhydrous magnesium sulfate, and concentrated under reduced pressure. The obtained residue was purified by silica gel chromatography (ethyl acetate: hexane=1:10-1:5) to give the title compound (1.0 g, yield 91%) as a colorless oil.

MS: m/z 231 (M+H).

Reference Example 29

N-(2-phenylethyl)-4-[4-(trifluoromethyl)phenyl]-1,3-thiazole-2-amine

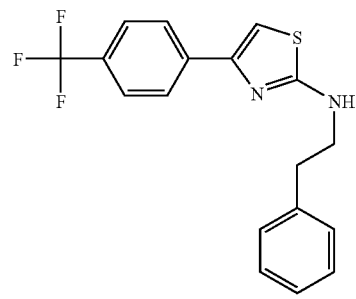

A mixture of N-(2-phenylethyl)thiourea (3.60 g, 20 mmol), 2-bromo-1-[4-(trifluoromethyl)phenyl]ethanone (5.34 g, 20 mmol) and N,N-dimethylformamide (5 mL) was stirred at room temperature for 16 hr. The reaction mixture was poured into water and the mixture was extracted with ethyl acetate. The extract was dried over anhydrous sodium sulfate, and concentrated under reduced pressure. The obtained solid was washed with hexane to give the title compound (5.2 g, yield 74%) as pale-yellow crystals.

MS: m/z 349 (M+H).

Reference Example 30

N-[2-(4-fluorophenyl)ethyl]-4-[4-(trifluoromethyl)phenyl]-1,3-thiazole-2-amine

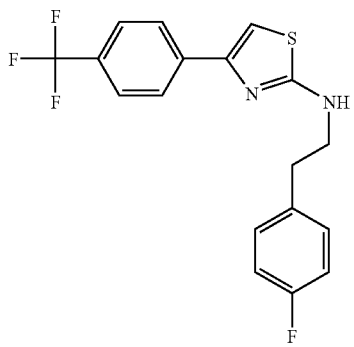

The title compound was obtained as pale-yellow crystals from N-[2-(4-fluorophenyl)ethyl]thiourea and 2-bromo-1-[4-(trifluoromethyl)phenyl]ethanone in the same manner as in Reference Example 29. Yield 48%.

$^1$H NMR (CDCl$_3$) δ 3.01(2H, t, J=7.0 Hz), 3.53-3.62(2H, m), 6.71-6.79(1H, m), 6.77(1H, s), 6.98-7.07(2H, m), 7.18-7.25(2H, m), 7.66(2H, d, J=8.3 Hz), 7.89(2H, d, J=8.1 Hz).

Reference Example 31 methyl 3-{4-[(3-aminobenzyl)oxy]phenyl}-propanoate

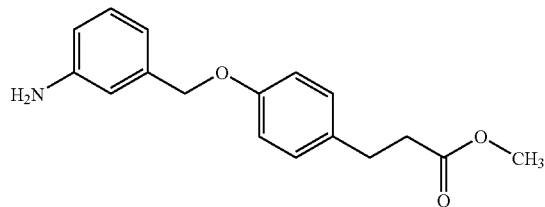

To a solution of methyl 3-(4-hydroxyphenyl)propanoate (5.10 g, 28.3 mmol) in N,N-dimethylformamide (40 mL) was added sodium hydride (in oil, 1.20 g, 30 mmol) at 0° C. and the mixture was stirred at the same temperature for 1 hr. 3-Nitrobenzylbromide (6.72 g, 31.1 mmol) was added and the mixture was stirred at room temperature for 1 hr. The reaction mixture was poured into water and extracted with ethyl acetate. The ethyl acetate layer was washed with water, dried over anhydrous magnesium sulfate, and concentrated to give a yellow oil. To a mixture of the obtained oil, tetrahydrofuran (50 mL) and ethanol (50 mL) was added platinum dioxide (350 mg) and the mixture was stirred under a hydrogen atmosphere for 16 hr. Insoluble materials were filtered off, and the filtrate was concentrated to give the title compound (7.73 g, yield 96%, 2 steps) as pale-yellow crystals.

$^1$H NMR (CDCl$_3$) δ 2.60(2H, t, J=7.7 Hz), 2.89(2H, t, J=7.7 Hz), 3.66(3H, s), 4.95(2H, s), 6.63(1H, dd, J=7.8,2.3 Hz), 6.74-6.82(2H, m), 6.89(2H, d, J=8.5 Hz), 7.07-7.18(3H, m).

Reference Example 32 methyl 3-(4-[(4-aminobenzyl)oxy]phenyl)propanoate

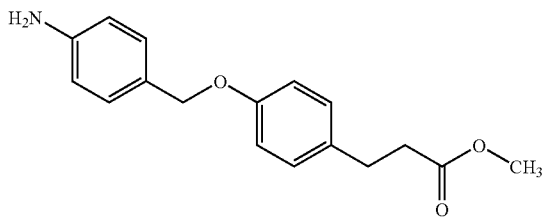

In the same manner as in Reference Example 31, the title compound was obtained as pale-yellow crystals from methyl 3-(4-hydroxyphenyl)propanoate and 4-nitrobenzyl bromide (yield 96%, 2 steps).

$^1$H NMR (CDCl$_3$) δ 2.59(2H, t, J=7.7 Hz), 2.88(2H, t, J=7.7 Hz), 3.59-3.80(5H, m), 4.90(2H, s), 6.69(2H, d, J=8.5 Hz), 6.89(2H, d, J=8.5 Hz), 7.10(2H, d, J=8.3 Hz), 7.21(2H, d, J=8.3 Hz).

Reference Example 33 ethyl 3-[2-fluoro-4-({4-[(propyl{4-[4-(trifluoromethyl)phenyl]-1,3-thiazol-2-yl}amino)methyl]benzyl}oxy)phenyl]propanoate

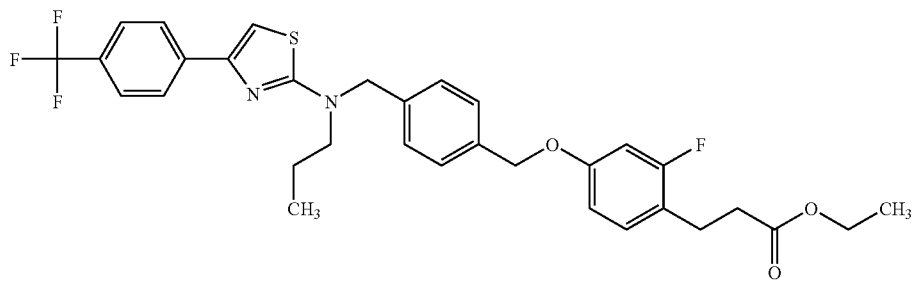

To a solution of N-propyl-4-[4-(trifluoromethyl)phenyl]-1,3-thiazole-2-amine (700 mg, 2.44 mmol) in N,N-dimethylformamide (5 mL) was added sodium hydride (100 mg, in oil, 2.5 mmol) at room temperature and the mixture was stirred at room temperature for 1 hr. Ethyl 3-(4-{[4-(chloromethyl)benzyl]oxy}-2-fluorophenyl)propanoate (700 mg, 2.0 mmol) was added and the mixture was further stirred at room temperature for 2 hr. The reaction mixture was poured into 1N hydrochloric acid and the mixture was extracted with ethyl acetate. The organic layer was concentrated and the residue was purified by preparative HPLC. The obtained fraction was concentrated, neutralized with 10% aqueous sodium hydrogencarbonate solution, and extracted with ethyl acetate. The ethyl acetate layer was filtered with a Presep Dehydration tube (Wako Pure Chemical Industries, Ltd.) and concentrated to give the title compound as a yellow oil.

MS: m/z 601 (M+H).

Reference Example 34

3-[2-fluoro-4-({4-[(propyl{4-[4-(trifluoromethyl)phenyl]-1,3-thiazol-2-yl}amino)methyl]benzyl}oxy)phenyl]propanoic acid

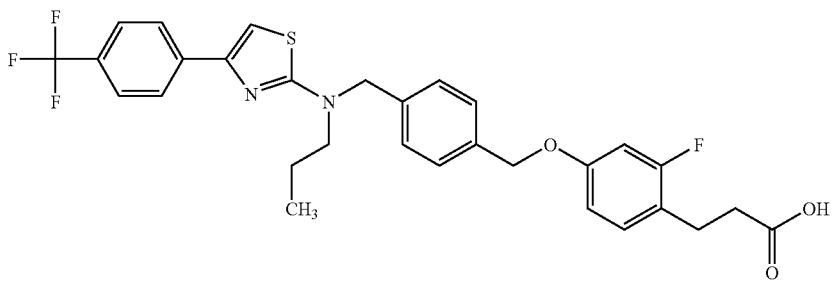

The yellow oil obtained in Reference Example 33 was dissolved in a mixed solvent of ethanol (5 mL) and tetrahydrofuran (5 mL), 2N aqueous sodium hydroxide solution (2 mL) was added, and the mixture was stirred at room temperature for 2 hr. The reaction mixture was diluted with water and neutralized with 1N hydrochloric acid. The precipitated solid was collected by filtration, washed with water and dried to give the title compound (345 mg, yield 30%, 2 step) as colorless crystals.

MS m/z 573 (M+H).

Reference Example 35 methyl 3-[4-({4-[[(4-phenyl-1,3-thiazol-2-yl)methyl](propyl)amino]benzyl}oxy)phenyl]propanoate

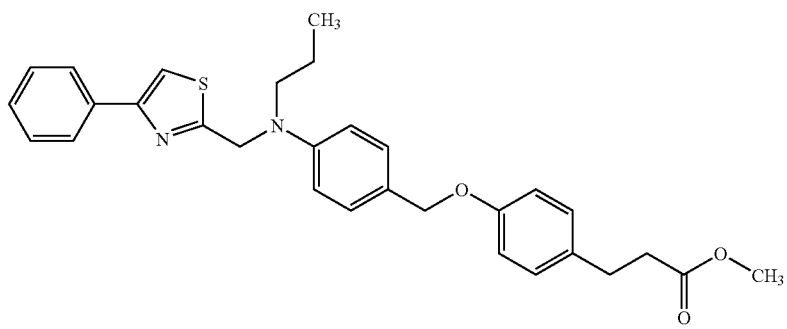

To a mixture of 4-phenyl-1,3-thiazole-2-carbaldehyde (380 mg, 2.0 mmol), methyl 3-{4-[(4-aminobenzyl)oxy]phenyl}-propanoate (570 mg, 2.0 mmol), acetic acid (0.1 mL), and 1,2-dichloroethane (5 mL) was added sodium triacetoxyborohydride (0.6 g, 2.8 mmol) under ice-cooling, and the mixture was warmed to room temperature and stirred for 1 hr. Propanal (120 mg, 2.1 mmol) and sodium triacetoxyborohydride (0.4 g, 1.9 mmol) were added to the reaction mixture, and the mixture was further stirred at room temperature for 1 hr. The reaction mixture was poured into water and extracted with ethyl acetate. The organic layer was washed with saturated brine, dried over anhydrous magnesium sulfate and concentrated. The residue was purified by silica gel column chromatography (ethyl acetate:hexane=1:19-1:2 in volume ratio) to give the title compound (340 mg, yield 68%) as a yellow oil.

$^1$H NMR (CDCl$_3$) δ 0.98(3H, t, J=7.3 Hz), 1.70-1.80(2H, m), 2.59(2H, t, J=7.8 Hz), 2.89(2H, t, J=7.8 Hz), 3.42-3.50 (2H, m), 3.66(3H, s), 4.84(2H, s), 4.89(2H, s), 6.78(2H, d, J=8.8 Hz), 6.89(2H, d, J=8.5 Hz), 7.10(2H, d, J=8.5 Hz), 7.24-7.35(3H, m), 7.36(1H, s), 7.40-7.47(2H, m), 7.86-7.91 (2H, m).

Reference Example 36

3-[4-({4-[[(4-phenyl-1,3-thiazol-2-yl)methyl](propyl)amino]benzyl}oxy)phenyl]propanoic acid

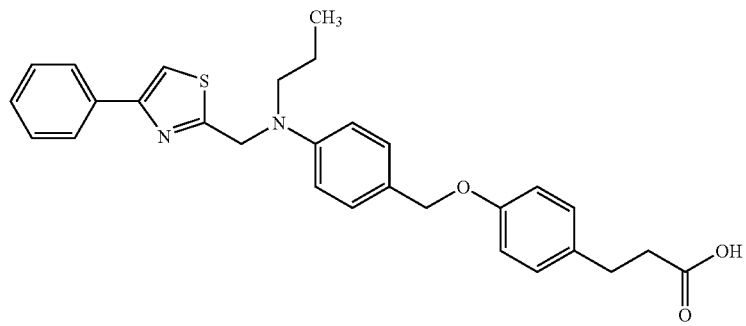

To a mixture of methyl 3-[4-({4-[[(4-phenyl-1,3-thiazol-2-yl)methyl](propyl)amino]benzyl}oxy)phenyl]propanoate (240 mg, 0.48 mmol), ethanol (5 mL) and tetrahydrofuran (5 mL) was added 2N aqueous sodium hydroxide solution (2 mL), and the mixture was stirred at room temperature for 2 hr. The reaction mixture was diluted with water, neutralized with 1N hydrochloric acid, and extracted with ethyl acetate. The organic layer was concentrated and the residue was purified by silica gel column chromatography (ethyl acetate:hexane=1:4-4:1 in volume ratio) to give the title compound (75 mg, yield 32%) as colorless prism crystals (recrystallized from acetone-heptane).

MS: m/z 487 (M+H).

Reference Example 37 methyl 3-[4-({3-[[(4-phenyl-1,3-thiazol-2-yl)methyl](propyl)amino]benzyl}oxy)phenyl]propanoate

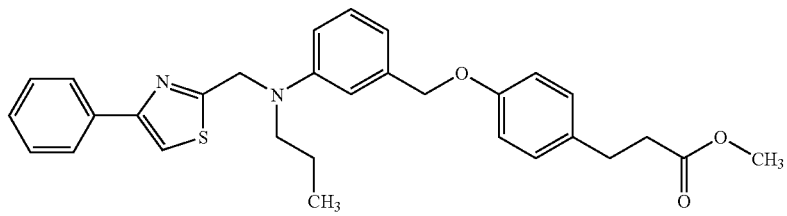

To a mixture of 4-phenyl-1,3-thiazole-2-carbaldehyde (210 mg, 1.1 mmol), methyl 3-{4-[(3-aminobenzyl)oxy]phenyl}-propanoate (285 mg, 1.0 mmol), acetic acid (0.2 mL) and 1,2-dichloroethane (5 mL) was added sodium triacetoxyborohydride (0.6 g, 2.8 mmol) under ice-cooling, and the mixture was warmed to room temperature and stirred for 1 hr. Propanal (200 mg, 3.4 mmol) was added to the reaction mixture, and the mixture was further stirred at room temperature for 1 hr. The reaction mixture was poured into water and extracted with ethyl acetate. The organic layer was washed with saturated brine, dried over anhydrous magnesium sulfate and concentrated. The residue was purified by silica gel column chromatography (ethyl acetate:hexane=1:19-1:2 in volume ratio) to give the title compound (393 mg, yield 78%) as a yellow oil.

$^1$H NMR (CDCl$_3$) δ 0.96(3H, t, J=7.4 Hz), 1.65-1.77(2H, m), 2.58(2H, t, J=7.8 Hz), 2.87(2H, t, J=7.8 Hz), 3.40-3.47 (2H, m), 3.66(3H, s), 4.83(2H, s), 4.97(2H, s), 6.72(1H, dd, J=8.3,2.3 Hz), 6.77-6.89(4H, m), 7.06(2H, d, J=8.7 Hz), 7.18-7.25(1H, m), 7.30-7.37(1H, m), 7.34(1H, s), 7.39-7.46(2H, m), 7.87-7.91(2H, m).

Reference Example 38

3-[4-({3-[[(4-phenyl-1,3-thiazol-2-yl)methyl](propyl)amino]benzyl}oxy)phenyl]propanoic acid

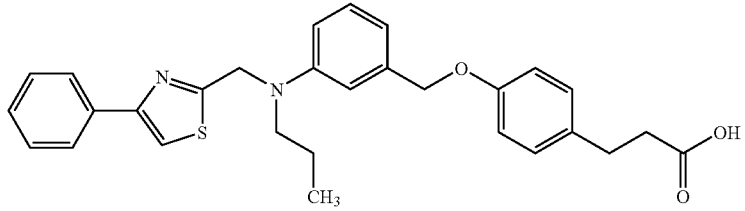

To a mixture of methyl 3-[4-({3-[[(4-phenyl-1,3-thiazol-2-yl)methyl](propyl)amino]benzyl}oxy)phenyl]propanoate (360 mg, 0.72 mmol), ethanol (5 mL) and tetrahydrofuran (5 mL) was added 2N aqueous sodium hydroxide solution (2 mL) and the mixture was stirred at room temperature for 2 hr. The reaction mixture was diluted with water, neutralized with 1N hydrochloric acid and extracted with ethyl acetate. The organic layer was concentrated and the residue was purified by silica gel column chromatography (ethyl acetate:hexane=1:4-4:1 in volume ratio) to give the title compound (262 mg, yield 75%) as colorless prism crystals (recrystallized from acetone-heptane).

MS: m/z 487 (M+H).

Reference Example 39 ethyl (2Z)-3-[4-(benzyloxy)phenyl]-2-fluoroacrylate

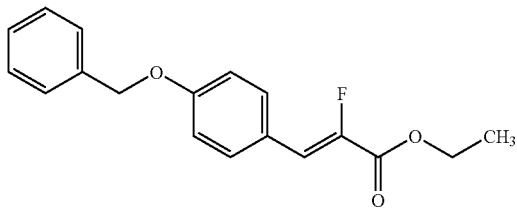

A solution of triethyl 2-fluoro-2-phosphonoacetate (4.90 g, 20.2 mmol) in tetrahydrofuran (40 mL) was stirred under a nitrogen atmosphere at 0° C., and 1.6 M n-butyl lithium/hexane solution (13.1 mL, 21.0 mmol) was added dropwise. The reaction mixture was stirred at 0° C. for 30 min and a solution of 4-benzyloxybenzaldehyde (4.29 g, 20.2 mmol) in tetrahydrofuran (20 mL) was added dropwise. The obtained mixture was stirred at room temperature for 3 hr and ice-cooled aqueous ammonium chloride solution was added, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=3:97-20:80) to give the title compound (4.90 g, yield 81%) as a yellow oil.

$^1$H NMR (CDCl$_3$) δ 1.29(3H, t, J=7.1 Hz), 4.28(2H, q, J=7.1 Hz), 5.09(2H, s), 6.79-7.02(3H, m), 7.29-7.63(7H, m).

Reference Example 40 ethyl 2-fluoro-3-(4-hydroxyphenyl)propanoate

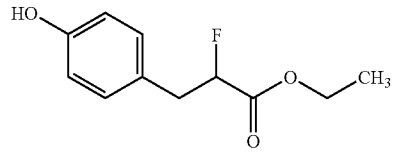

The title compound was obtained as a colorless oil in the same manner as in Reference Example 27 from ethyl(2Z)-3-[4-(benzyloxy)phenyl]-2-fluoroacrylate. Yield 50%.

$^1$H NMR (CDCl$_3$) δ 1.22-1.30(3H, m), 3.00-3.25(2H, m), 4.17-4.27(2H, m), 4.76-4.78(1H, m), 4.92-5.15(1H, m), 6.74-6.81(2H, m), 7.08-7.15(2H, m).

Reference Example 41 ethyl 2,2-difluoro-3-(4-hydroxyphenyl)propanoate

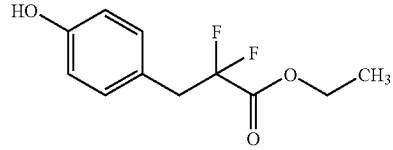

To a solution of ethyl 2,2-difluoro-3-(4-methoxyphenyl)propanoate (1.72 g, 7.05 mmol) synthesized according to the method described in Synthesis, vol. 13, pages 1917-1924, 2000 and aluminum chloride (2.82 g, 21.2 mmol) in dichloromethane (50 mL) was added dropwise 1-octanethiol (2.06 g, 14.1 mmol) and the mixture was stirred at room temperature for 2.5 hr. The reaction mixture was poured into ice water and stirred for 30 min. The organic layer was separated, washed with saturated brine, dried over anhydrous magnesium sulfate, and concentrated under reduced pressure. The residue was purified by silica gel column chromatography (ethyl acetate:hexane=8:92-60:40) to give the title compound (0.90 g, yield 56%) as a colorless oil.

$^1$H NMR (CDCl$_3$) δ 1.26(3H, t, J=7.1 Hz), 3.30(2H, t, J=16.3 Hz), 4.25(2H, q, J=7.2 Hz), 4.84(1H, s), 6.74-6.82 (2H, m), 7.13(2H, d, J=8.3 Hz).

Reference Example 42

N-(3-methylbutyl)-4-[4-(trifluoromethyl)phenyl]-1,3-thiazole-2-amine

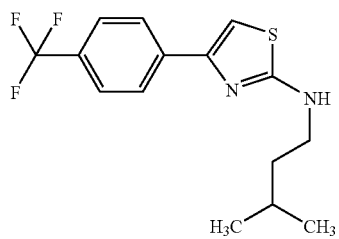

A solution of N-(3-methylbutyl)thiourea (3.00 g, 20.5 mmol), 2-bromo-1-[4-(trifluoromethyl)phenyl]ethanone (5.45 g, 20.5 mmol) and sodium acetate (2.19 g, 26.7 mmol) in ethanol (50 mL) was stirred at 90° C. for 4 hr. The reaction mixture was poured into water and extracted with ethyl acetate. The extract was dried over anhydrous sodium sulfate and concentrated under reduced pressure. The obtained solid was recrystallized from dichloromethane-hexane to give the title compound (1.76 g, yield 74%) as pale-yellow crystals.

$^1$H NMR (CDCl$_3$) δ 0.95(6H, d, J=6.7 Hz), 1.55(2H, q, J=7.0 Hz), 1.63-1.79(1H, m), 3.24-3.36(2H, m), 5.29(1H,br s), 6.80(1H, s), 7.61(2H, d, J=8.3 Hz), 7.90(2H, d, J=8.3 Hz).

Reference Example 43 methyl 3-[4-({4-[((3-methylbutyl){4-[4-(trifluoromethyl)phenyl]-1,3-thiazol-2-yl}amino)methyl]-benzyl}oxy)phenyl]propanoate

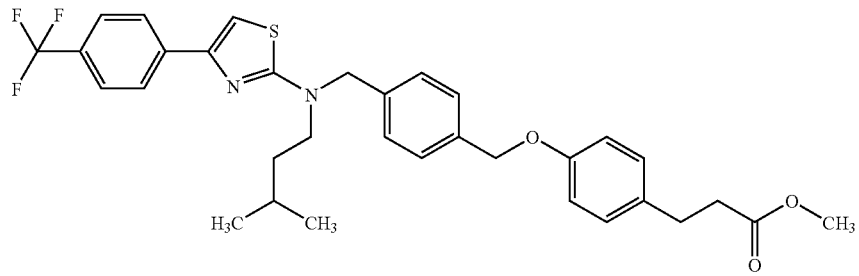

To a solution of N-(3-methylbutyl)-4-[4-(trifluoromethyl)phenyl]-1,3-thiazole-2-amine (500 mg, 1.59 mmol) in N,N-dimethylformamide (10 mL) was added 60% sodium hydride (63.6 mg, 1.59 mmol) and the mixture was stirred for 30 min. Methyl 3-(4-{[4-(chloromethyl)benzyl]oxy}phenyl)propanoate (462 mg, 1.45 mmol) was added and the obtained mixture was stirred at room temperature for 13 hr. Water was added to the reaction mixture, and the mixture was extracted with ethyl acetate. The extract was washed with saturated brine, dried over anhydrous magnesium sulfate and concentrated under reduced pressure. The residue was purified by silica gel column chromatography (ethyl acetate:hexane=5:95-40:60) to give the title compound (490 mg, yield 57%) as a yellow oil.

MS: m/z 597 (M+H).

Reference Example 44

3-[4-({4-[((3-methylbutyl){4-[4-(trifluoromethyl)phenyl]-1,3-thiazol-2-yl}amino)methyl]-benzyl}oxy)phenyl]propanoic acid

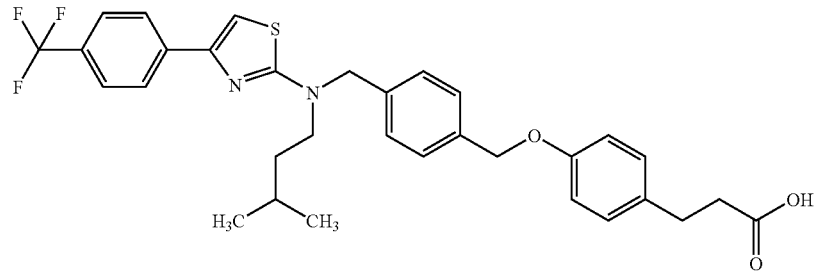

The title compound (yield 40%) was obtained as colorless crystals in the same manner as in below-mentioned Example 32 from methyl 3-[4-({4-[((3-methylbutyl){4-[4-(trifluoromethyl)phenyl]-1,3-thiazol-2-yl}amino)methyl]-benzyl}oxy)phenyl]propanoate.

MS: m/z 583 (M+H).

Reference Example 45

4-butyrylphenyl trifluoromethanesulfonate

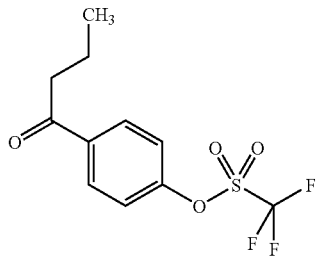

To an ice-cooled solution of 1-(4-hydroxyphenyl)butan-1-one (15.0 g, 91.4 mmol) in pyridine (100 mL) was added dropwise trifluoromethanesulfonic acid anhydride (30.9 g, 110 mmol). The obtained mixture was stirred at room temperature for 3 hr, diluted with water and extracted with ethyl acetate. The extract was washed with saturated brine, dried over anhydrous magnesium sulfate, and concentrated under reduced pressure. The residue was purified by silica gel column chromatography (ethyl acetate:hexane=5:95-40:60) to give the title compound (27.1 g, yield 100%) as a pale-yellow oil.

$^1$H NMR (CDCl$_3$) δ 1.01(3H, t, J=7.4 Hz), 1.71-1.85(2H, m), 2.95(2H, t, J=7.3 Hz), 7.34-7.41(2H, m), 8.02-8.09(2H, m).

Reference Example 46 methyl 4-butyrylbenzoate

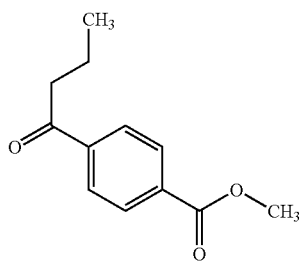

A mixture of 4-butyrylphenyl trifluoromethanesulfonate (27.1 g, 91.7 mmol), palladium (II) acetate (1.24 g, 5.50 mmol), 1,3-bis(diphenylphosphino)propane (2.45 g, 6.05 mmol), triethylamine (23.2 g, 229 mmol), methanol (200 mL) and dimethyl sulfoxide (100 mL) was heated under reflux under a CO atmosphere at 80° C. for 8 hr. After cooling the reaction mixture, 0.5N hydrochloric acid was added, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=3:97-30:70) and recrystallized from ethyl acetate-hexane to give the title compound (9.24 g, yield 49%) as colorless crystals.

MS: m/z 207 (M+H).

Reference Example 47

(4-{1-[(4-phenyl-1,3-thiazol-2-yl)methyl]butyl}phenyl)methanol

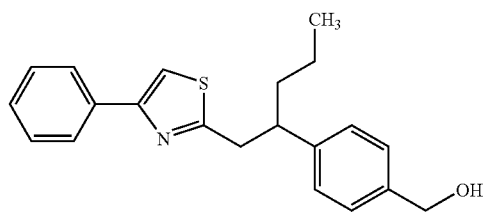

To a suspension of triphenyl[(4-phenyl-1,3-thiazol-2-yl)methyl]phosphonium bromide (1.00 g, 1.94 mmol) synthesized according to the method described in Liebigs Annalen der Chemie, vol. 4, pages 623-632, 1981 in benzene (20 mL) was added potassium-t-butoxide (239 mg, 2.13 mmol), and the mixture was stirred under an argon atmosphere at room temperature for 3 hr. To a reaction solution was added dropwise a solution of methyl 4-butyrylbenzoate (319 mg, 1.55 mmol) in benzene (20 mL), and the mixture was stirred at room temperature for 3 hr and then heated under reflux for 16 hr. The reaction mixture was cooled to room temperature, poured into water and extracted with ethyl acetate. The extract was washed with saturated brine, dried over anhydrous magnesium sulfate, and concentrated under reduced pressure. The residue was purified by silica gel column chromatography (ethyl acetate:hexane=5:95-20:80) to give a yellow oil. Tetrahydrofuran (20 mL), methanol (10 mL) and 10% palladium-carbon (200 mg) were added to the oil, and the mixture was stirred under a hydrogen atmosphere at room temperature for 2 days. The catalyst was filtered off, and the obtained filtrate was concentrated to give a colorless oil. To a solution of the oil in tetrahydrofuran (10 mL) was added dropwise 1.0M diisobutyl aluminum hydride toluene solution (10 mL, 10 mmol) under ice-cooling. The reaction mixture was stirred at room temperature for 2 hr, sodium sulfate 10 hydrate was added, and the mixture was further stirred at room temperature for 1 hr. The insoluble materials were filtered off and the filtrate was concentrated. The residue was purified by silica gel column chromatography (ethyl acetate:hexane=10:90-60:40) to give the title compound (250 mg, yield 48%) as a colorless oil.

MS: m/z 338 (M+H).

Reference Example 48 ethyl 3-{2-fluoro-4-[(4-{1-[(4-phenyl-1,3-thiazol-2-yl)methyl]butyl}benzyl)oxy]phenyl}propanoate

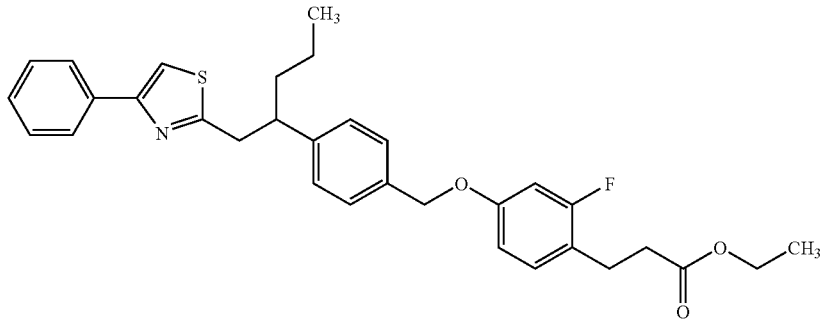

The title compound was obtained as a colorless oil in the same manner as in below-mentioned Example 31 from ethyl 3-(2-fluoro-4-hydroxyphenyl)propanoate and (4-{1-[(4-phenyl-1,3-thiazol-2-yl)methyl]butyl}phenyl)methanol (yield 89%).

MS: m/z 532 (M+H).

Reference Example 49

3-{2-fluoro-4-[(4-{1-[(4-phenyl-1,3-thiazol-2-yl)methyl]butyl}benzyl)oxy]phenyl}propanoic acid

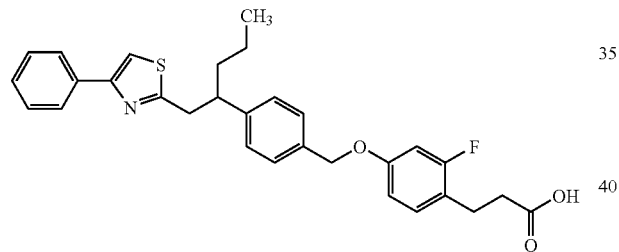

The title compound was obtained as colorless crystals in the same manner as in below-mentioned Example 32 from ethyl 3-{2-fluoro-4-[(4-{1-[(4-phenyl-1,3-thiazol-2-yl)methyl]butyl}benzyl)oxy]phenyl}propanoate (yield 72%).

MS: m/z 504 (M+H).

Reference Example 50

3-{2-fluoro-4-[(4-{1-[(4-phenyl-1,3-thiazol-2-yl)methyl]butyl}benzyl)oxy]phenyl}propanoic acid 0.5 calcium salt

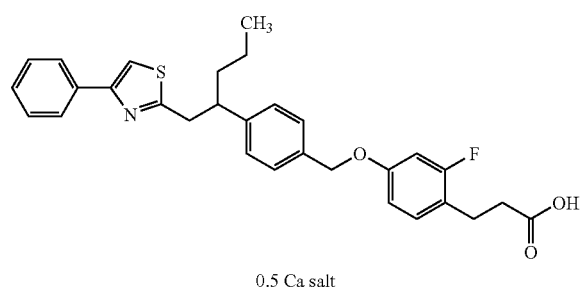

0.5 Ca salt

The title compound was obtained as colorless crystals in the same manner as in below-mentioned Example 33 from 3-{2-fluoro-4-[(4-{1-[(4-phenyl-1,3-thiazol-2-yl)methyl]butyl}benzyl)oxy]phenyl}propanoic acid (yield 70%).

MS: m/z 504 (M+H) (free).

Reference Example 51 methyl 6-{[(2-phenylethyl)(4-phenyl-1,3-thiazol-2-yl)amino]methyl}nicotinate

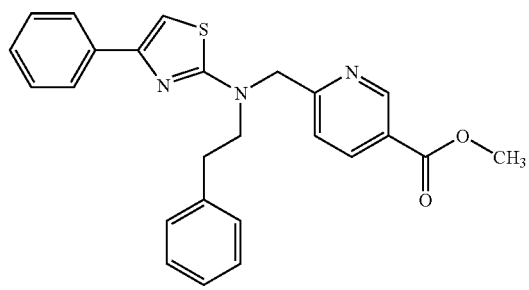

The title compound was obtained as a yellow oil in the same manner as in Reference Example 15 from 4-phenyl-N-(2-phenylethyl)-1,3-thiazole-2-amine and methyl 6-(bromomethyl)nicotinate (yield 65%).

$^1$H NMR (CDCl$_3$) δ 2.96-3.11(2H, m), 3.71-3.84(2H, m), 3.94(3H, s), 4.87(2H, s), 6.76(1H,s), 7.13-7.48(9H, m), 7.80-7.89(2H, m), 8.20(1H, dd, J=8.2,2.2 Hz), 9.16(1H, d, J=2.1 Hz).

Reference Example 52

(6-{[(2-phenylethyl)(4-phenyl-1,3-thiazol-2-yl)amino]methyl}pyridin-3-yl)methanol

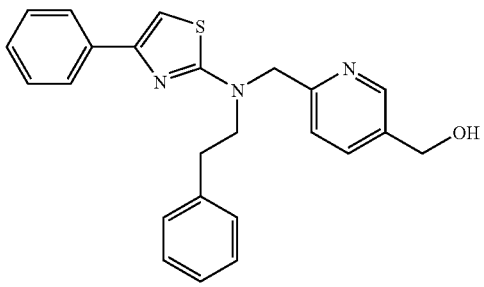

The title compound was obtained as a yellow oil in the same manner as in Reference Example 16 from methyl 6-{[(2-phenylethyl)(4-phenyl-1,3-thiazol-2-yl)amino]methyl}nicotinate (yield 65%).

$^1$H NMR (CDCl$_3$) δ 2.95-3.09(2H, m), 3.70-3.85(2H, m), 4.70(2H, s), 4.81(2H, s), 6.74(1H, s), 7.14-7.44(9H, m), 7.64(1H, dd, J=8.0,2.2 Hz), 7.80-7.92(2H, m), 8.54(1H, d, J=1.7 Hz).

Reference Example 53

4-(1-hydroxybutyl)benzaldehyde

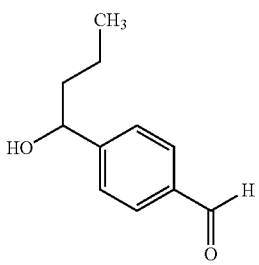

A solution of 4-(diethoxymethyl)benzaldehyde (10.4 g, 50.0 mmol) in tetrahydrofuran (200 mL) was stirred at room temperature under a nitrogen atmosphere, 2 M n-propylmagnesium bromide tetrahydrofuran solution (27.5 mL, 55.0 mmol) was added dropwise. After 30 min, aqueous ammonium chloride solution was added to the reaction mixture, and the mixture was extracted with ethyl acetate. The extract was washed with saturated brine, dried over anhydrous sodium sulfate, and concentrated under reduced pressure. The residue was purified by silica gel column chromatography (ethyl acetate:hexane=10:90-20:80) to give 1-[4-(diethoxymethyl)phenyl]butane-1-ol (6.39 g, 25.3 mmol) as a colorless oil. The oil was dissolved in a mixture of tetrahydrofuran (75 mL) and water (25 mL) and p-toluenesulfonic acid monohydrate (0.500 g, 2.63 mmol) was added. The mixture was stirred at room temperature for 5 hr. The reaction mixture was diluted with water and extracted with ethyl acetate. The extract was washed with saturated brine, dried over anhydrous magnesium sulfate, and concentrated under reduced pressure. The residue was purified by silica gel column chromatography (ethyl acetate:hexane=10:90-40:60) to give the title compound (4.51 g, yield 51%, 2 step) as a colorless oil.

$^1$H NMR (CDCl$_3$) δ 0.95(3H, t, J=7.3 Hz), 1.29-1.53(2H, m), 1.63-1.86(2H, m), 1.94(1H, d, J=3.6 Hz), 4.75-4.83(1H, m), 7.52(2H, d, J=8.2 Hz), 7.87(2H, d, J=8.2 Hz), 10.00(1H, s).

Reference Example 54

1-[4-(hydroxymethyl)phenyl]butan-1-ol

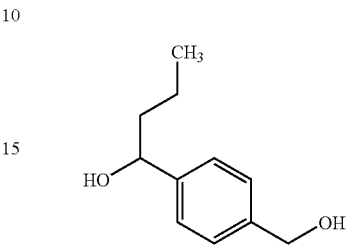

4-(1-Hydroxybutyl)benzaldehyde (4.51 g, 25.3 mmol) was dissolved in a mixture of methanol (10 mL) and tetrahydrofuran (20 mL), and sodium borohydride (0.479 g, 12.7 mmol) was added with stirring under ice-cooling. The mixture was stirred at the same temperature for 1.5 hr. Water and 1N hydrochloric acid were added to the reaction mixture and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=30:70-80:20) to give the title compound (4.32 g, yield 95%) as a colorless oil.

$^1$H NMR (CDCl$_3$) δ 0.93(3H, t, J=7.3 Hz), 1.22-1.52(2H, m), 1.61-1.86(4H, m), 4.65-4.73(3H, m), 7.35(4H, s).

Reference Example 55 ethyl 3-(2-fluoro-4-{[4-(1-hydroxybutyl)benzyl]oxy}phenyl)propanoate

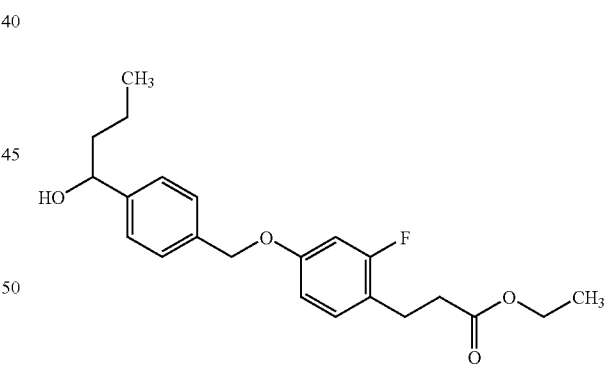

A solution of ethyl 3-(2-fluoro-4-hydroxyphenyl)propanoate (2.12 g, 10.0 mmol), 1-[4-(hydroxymethyl)phenyl]-butane-1-ol (1.80 g, 10.0 mmol) and tributylphosphine (4.04 mL, 20.0 mmol) in toluene (150 mL) was stirred under ice-cooling and 1,1'-(azodicarbonyl)dipiperidine (5.04 g, 20.0 mmol) was added by small portions. The mixture was warmed to room temperature and stirred for 22 hr. Hexane (75 mL) was added to the reaction mixture, and precipitated insoluble material was filtered off. The filtrate was concentrated under reduced pressure. The residue was purified by silica gel column chromatography (ethyl acetate:hexane=5:95-30:70) to give the title compound as a colorless oil (1.93 g, yield 52%).

¹H NMR (CDCl₃) δ 0.93(3H, t, J=7.3 Hz), 1.23(3H, t, J=7.1 Hz), 1.27-1.51(2H, m), 1.61-1.86(3H, m), 2.58(2H, t, J=7.6 Hz), 2.90(2H, t, J=7.6 Hz), 4.12(2H, q, J=7.1 Hz), 4.66-4.74(1H, m), 5.01(2H, s), 6.62-6.72(2H, m), 7.05-7.14 (1H, m), 7.33-7.43(4H, m).

Reference Example 56 ethyl 3-{2-fluoro-4-[(4-{1-[(4-phenyl-1,3-thiazol-2-yl)thio]butyl}benzyl)oxy]phenyl}propanoate

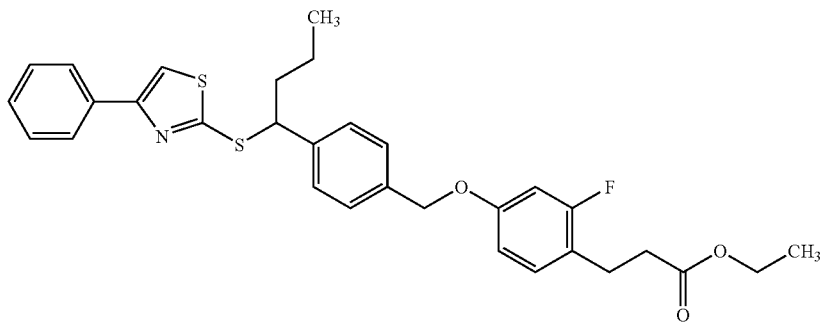

To a solution of ethyl 3-(2-fluoro-4-{[4-(1-hydroxybutyl) benzyl]oxy}phenyl)propanoate (0.500 g, 1.34 mmol), 2-mercapto-4-phenylthiazole (0.284 g, 1.47 mmol) and triphenylphosphine (0.700 g, 2.67 mmol) in toluene (10 mL) was added diethyl azodicarboxylate (40% toluene solution, 1.21 mL, 2.67 mmol) with stirring at room temperature, and the mixture was stirred at the same temperature for 1.5 hr. The reaction mixture was concentrated under reduced pressure, and the residue was purified by silica gel column chromatography (ethyl acetate:hexane=0:100-20:80) to give the title compound (0.555 g, yield 76%) as a colorless oil.

MS: m/z 550 (M+H).

Reference Example 57

3-{2-fluoro-4-[(4-{1-[(4-phenyl-1,3-thiazol-2-yl) thio]butyl}benzyl)oxy]phenyl}propanoic acid

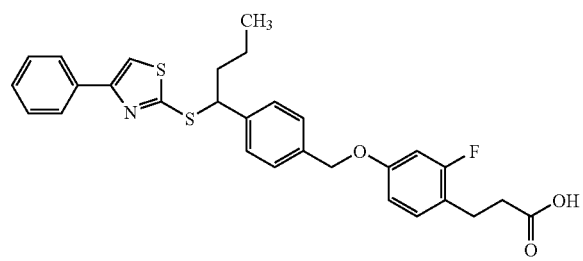

To a solution of ethyl 3-{2-fluoro-4-[(4-{1-[(4-phenyl-1, 3-thiazol-2-yl)thio]butyl}benzyl)oxy]phenyl}propanoate (0.130 g, 0.236 mmol) in a mixture of ethanol (0.5 mL) and tetrahydrofuran (1 mL) was added 2N aqueous sodium hydroxide solution (0.25 mL) and the mixture was stirred at 50° C. for 3 hr. Water was added to the reaction mixture, and the mixture was acidified with 1N hydrochloric acid and extracted with ethyl acetate. The extract was washed with saturated brine, dried over anhydrous magnesium sulfate, and concentrated under reduced pressure. The residue was purified by silica gel column chromatography (ethyl acetate:hexane=20:80-70:30) to give the title compound (0.119 g, yield 97%) as a colorless oil.

MS: m/z 522 (M+H).

Example 1

3-{4-[(4-{[benzyl(4-phenyl-1,3-thiazol-2-yl)amino]-methyl}benzyl)oxy]phenyl}propanoic acid

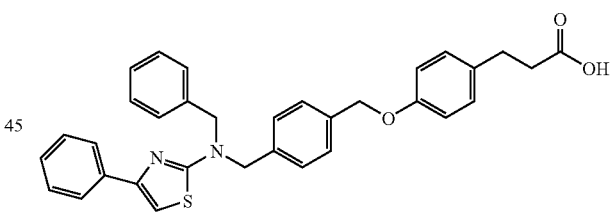

A mixture of 2-bromo-1-phenylethanone (100 mg), N-benzylthiourea (83 mg) and N,N-dimethylformamide (2 mL) was stirred at 80° C. for 1 hr. The reaction mixture was cooled to 0° C., sodium hydride (60% in oil, 80 mg) was added, and the mixture was stirred at room temperature for 30 min. Methyl 3-(4-{[4-(chloromethyl)benzyl]oxy}phenyl) propanoate (300 mg) was added to the reaction mixture at room temperature, and the mixture was stirred at room temperature for 1 hr. The reaction mixture was poured into water and extracted with ethyl acetate. The ethyl acetate layer was dried using a Presep Dehydration tube (manufactured by Wako Pure Chemical Industries, Ltd.) and concentrated. The residue was purified by silica gel column chromatography (ethyl acetate:hexane=1:19-1:0 in volume ratio) to give the title compound (110 mg, yield 41%) as colorless crystals.

MS: m/z 535 (M+H).

Example 2

3-{4-[(4-{[(4-isopropyl-1,3-thiazol-2-yl)(2-phenyl-ethyl)amino]methyl}benzyl)oxy]phenyl}propanoic acid

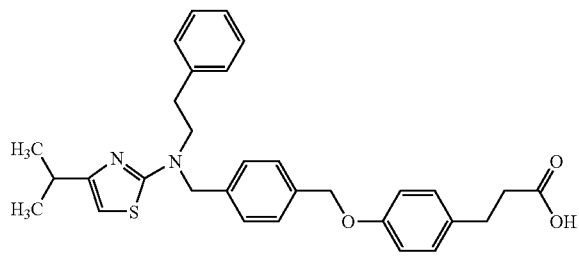

A mixture of methyl 3-{4-[(4-{[(4-isopropyl-1,3-thiazol-2-yl)(2-phenylethyl)amino]methyl}benzyl)oxy]phenyl}propanoate (350 mg), 2N aqueous sodium hydroxide solution (2 mL) and ethanol (5 mL) was stirred at room temperature for 1 hr. The reaction mixture was diluted with water, neutralized with 1N hydrochloric acid, and extracted with ethyl acetate. The ethyl acetate layer was dried over anhydrous magnesium sulfate and concentrated to give the title compound (210 mg, yield 62%) as colorless crystals.

MS: m/z 515 (M+H).

Example 3

3-{4-[(4-{[(2-phenylethyl)(4-pyridin-2-yl-1,3-thiazol-2-yl)amino]methyl}benzyl)oxy]phenyl}propanoic acid

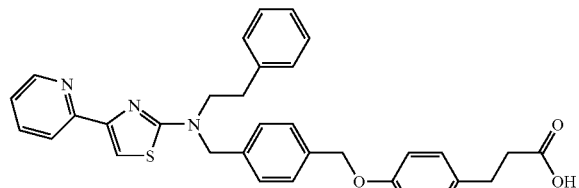

The title compound was obtained as pale-yellow crystals in the same manner as in Example 2 from methyl 3-{4-[(4-{[(2-phenylethyl)(4-pyridin-2-yl-1,3-thiazol-2-yl)amino]methyl}benzyl)oxy]phenyl}propanoate (yield 72%).

MS: m/z 550 (M+H).

Example 4

3-{4-[(4-([[2-(4-chlorophenyl)ethyl](4-phenyl-1,3-thiazol-2-yl)amino]methyl)benzyl)oxy]phenyl}propanoic acid

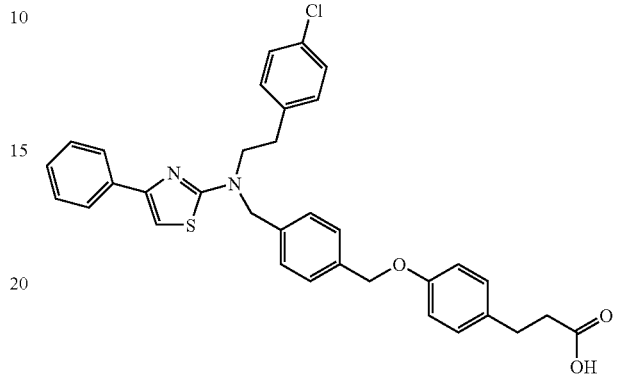

A mixture of N-[2-(4-chlorophenyl)ethyl]thiourea (108 mg), 2-bromo-1-phenylethanone (100 mg) and N,N-dimethylformamide (3 mL) was stirred at room temperature for 1 hr. Sodium hydride (60% in oil, 40 mg) was added to this mixture under ice-cooling, allowed to warm to room temperature and stirred for 1 hr. Methyl 3-(4-{[4-(chloromethyl)benzyl]oxy}phenyl)propanoate (159 mg) was added to the reaction mixture under ice-cooling, and the mixture was allowed to warm to room temperature and further stirred for 1 hr. The reaction mixture was poured into aqueous potassium dihydrogenphosphate solution, and the mixture was extracted with ethyl acetate. The ethyl acetate layer was concentrated and the residue was purified by preparative HPLC (gradient cycle A) to give the title compound (113 mg, yield 39%) as a yellow oil.

MS: m/z 583 (M+H).

Example 5

3-{4-[(4-{[[3-(diethylamino)propyl](4-phenyl-1,3-thiazol-2-yl)amino]methyl}benzyl)oxy]phenyl}propanoic acid A mixture of N-[3-(diethylamino)propyl]thiourea (90 mg), 2-bromo-1-phenylethanone (100 mg) and N,N-dimethylformamide (3 mL) was stirred at room temperature for 1 hr. Sodium hydride (60% in oil, 40 mg) was added to the mixture under ice-cooling. The mixture was allowed to warm to room temperature and stirred for 1 hr. Methyl 3-(4-{[4-(chloromethyl)benzyl]-oxy}phenyl)propanoate (159 mg) was added to the reaction mixture under ice-cooling, allowed to warm to room temperature and stirred for 1 hr. The reaction mixture was poured into aqueous potassium dihydrogenphosphate solution and the mixture was extracted with ethyl acetate. The ethyl acetate layer was concentrated and the residue was purified by basic silica gel column chromatography to give a yellow oil. A mixture of the yellow oil, 2N aqueous sodium hydroxide solution (2 mL) and ethanol (5 mL) was stirred at room temperature for 1 hr. The reaction mixture was poured into aqueous potassium dihydrogenphosphate solution, and extracted with ethyl acetate. The ethyl acetate layer was dried using a Presep Dehydration tube (manufactured by Wako Pure Chemical Industries, Ltd.) and concentrated to give the title compound (142 mg, yield 51%) as a yellow oil.

MS: m/z 558 (M+H).

Example 6

3-{4-[(4-{[(3-methoxypropyl)(4-phenyl-1,3-thiazol-2-yl)amino]methyl}benzyl)oxy]phenyl}propanoic acid

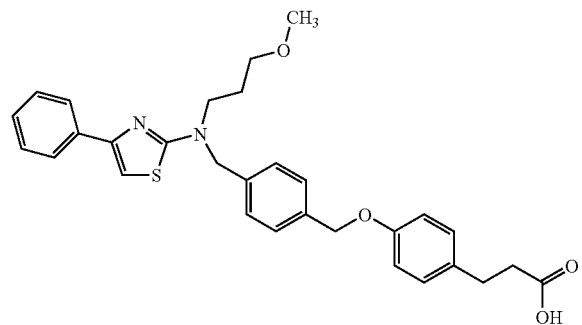

The title compound was synthesized in the same manner as in Example 4 from N-(3-methoxypropyl)thiourea (yield 49%). Yellow oil.

MS: m/z 517 (M+H).

Example 7

3-{4-[(4-{[[2-(4-methylphenyl)ethyl](4-phenyl-1,3-thiazol-2-yl)amino]methyl}benzyl)oxy]phenyl}propanoic acid

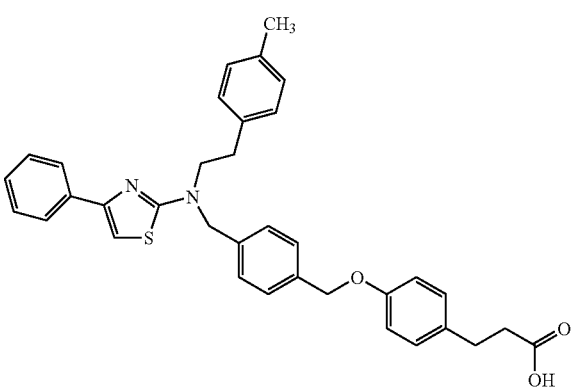

The title compound was synthesized in the same manner as in Example 4 from N-[2-(4-methylphenyl)ethyl]thiourea (yield 44%). Yellow oil.

MS: m/z 563 (M+H).

Example 8 ethyl 3-{2-fluoro-4-[(4-{[[2-(4-fluorophenyl)ethyl](4-isopropyl-1,3-thiazol-2-yl)amino]methyl}benzyl)oxy]phenyl}propanoate

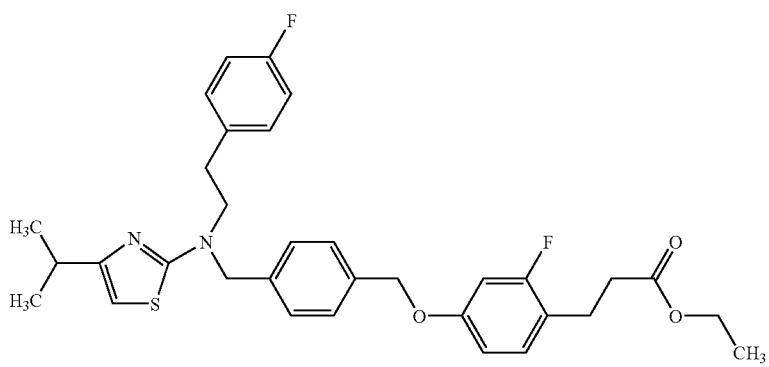

A solution of (4-{[[2-(4-fluorophenyl)ethyl](4-isopropyl-1,3-thiazol-2-yl)amino]methyl}phenyl)methanol (510 mg), ethyl 3-(2-fluoro-4-hydroxyphenyl)propanoate (280 mg), triphenylphosphine (420 mg) and diethyl azodicarboxylate (40% toluene solution, 750 mg) in toluene (3 mL) was stirred at room temperature for 1 hr. The reaction mixture was concentrated, and the residue was purified by silica gel column chromatography (ethyl acetate:hexane=1:19-1:1 in volume ratio) to give the title compound (490 mg, yield 64%) as a yellow oil.

MS: m/z 579 (M+H).

Example 9

3-{2-fluoro-4-[(4-{[[2-(4-fluorophenyl)ethyl](4-isopropyl-1,3-thiazol-2-yl)amino]methyl}benzyl)oxy]-phenyl}propanoic acid

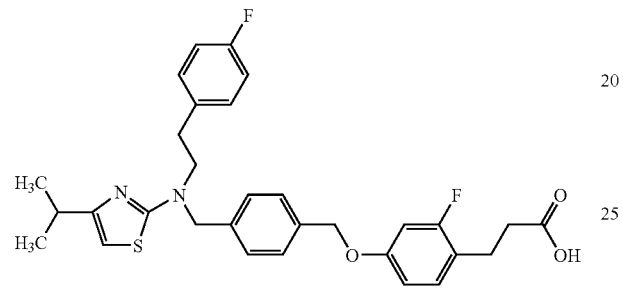

Ethyl 3-{2-fluoro-4-[(4-{[[2-(4-fluorophenyl)ethyl](4-isopropyl-1,3-thiazol-2-yl)amino]methyl}benzyl)oxy]phenyl}-propanoate (485 mg) was dissolved in ethanol (5 mL), 2N aqueous sodium hydroxide solution (2 mL) was added, and the mixture was stirred at room temperature for 1 hr. The reaction mixture was diluted with water, neutralized with 1N hydrochloric acid, and extracted with ethyl acetate. The extract was dried using a Presep Dehydration tube (manufactured by Wako Pure Chemical Industries, Ltd.) and concentrated to give the title compound (354 mg, yield 75%) as colorless crystals.

MS: m/z 551 (M+H).

Example 10 methyl 3-{4-[(4-{[(4-phenyl-1,3-thiazol-2-yl)(2-pyridin-2-ylethyl)amino]methyl}benzyl)oxy]phenyl}propanoate

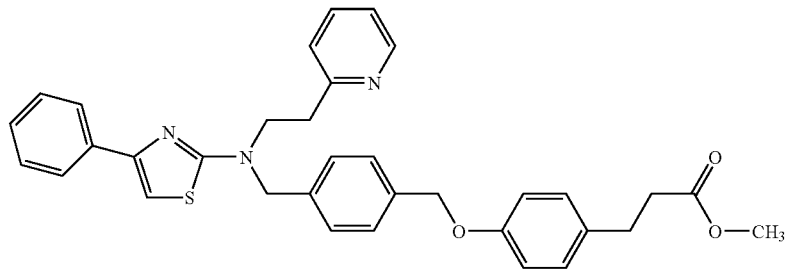

The title compound was synthesized in the same manner as in Example 8 from (4-{[(4-phenyl-1,3-thiazol-2-yl)(2-pyridin-2-ylethyl)amino]methyl}phenyl)methanol and methyl 3-(4-hydroxyphenyl)propanoate by Mitsunobu reaction (yield 57%). Yellow oil.

MS: m/z 564 (M+H).

Example 11 ethyl 3-{2-fluoro-4-[(4-{[(4-phenyl-1,3-thiazol-2-yl)(2-pyridin-2-ylethyl)amino]methyl}benzyl)oxy]phenyl}-propanoate

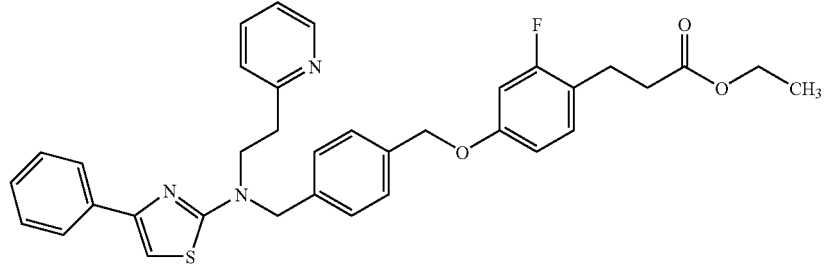

The title compound was synthesized in the same manner as in Example 8 from (4-{[(4-phenyl-1,3-thiazol-2-yl)(2-pyridin-2-ylethyl)amino]methyl}phenyl)methanol and ethyl 3-(2-fluoro-4-hydroxyphenyl)propanoate by Mitsunobu reaction (yield 41%). Yellow oil.

MS: m/z 596 (M+H).

Example 12

3-{4-[(4-([(4-phenyl-1,3-thiazol-2-yl)(2-pyridin-2-ylethyl)amino]methyl}benzyl)oxy]phenyl)propanoic acid

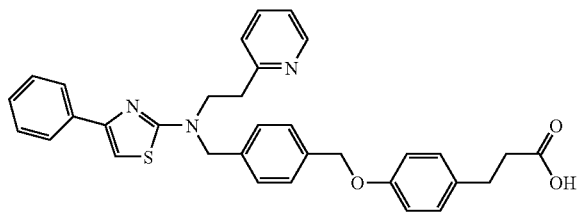

The title compound was synthesized in the same manner as in Example 9 from methyl 3-(4-[(4-{[(4-phenyl-1,3-thiazol-2-yl)(2-pyridin-2-ylethyl)amino]methyl)benzyl)oxy]phenyl}-propanoate by basic hydrolysis (yield 82%). Pale-yellow crystals.

MS: m/z 550 (M+H).

Example 13

3-{2-fluoro-4-[(4-{[(4-phenyl-1,3-thiazol-2-yl)(2-pyridin-2-ylethyl)amino]methyl}benzyl)oxy] phenyl}propanoic acid

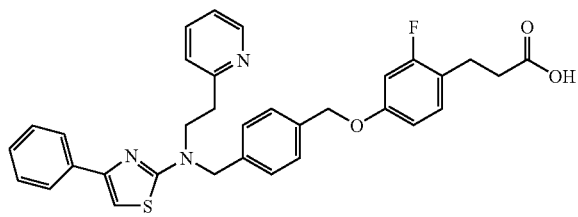

The title compound was synthesized in the same manner as in Example 9 from ethyl 3-{2-fluoro-4-[(4-{[(4-phenyl-1,3-thiazol-2-yl)(2-pyridin-2-ylethyl)amino]methyl}benzyl)oxy]-phenyl}propanoate by basic hydrolysis (yield 70%). Pale-yellow crystals.

MS: m/z 568 (M+H).

Example 14

3-{4-[(4-{[(3-phenylpropyl)(4-pyridin-2-yl-1,3-thiazol-2-yl)amino]methyl}benzyl)oxy] phenyl}propanoic acid

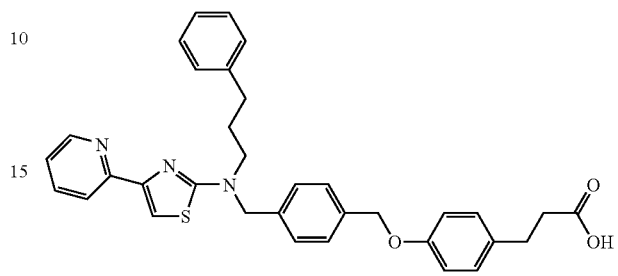

The title compound was synthesized in the same manner as in Example 4 from N-(3-phenylpropyl)thiourea and 2-bromo-1-pyridin-2-ylethanone (yield 27%). Brown solid.

MS: m/z 564 (M+H).

Example 15

3-{4-[(4-{[(4-isopropyl-1,3-thiazol-2-yl)(2-pyridin-2-ylethyl)amino]methyl}benzyl)oxy] phenyl}propanoic acid

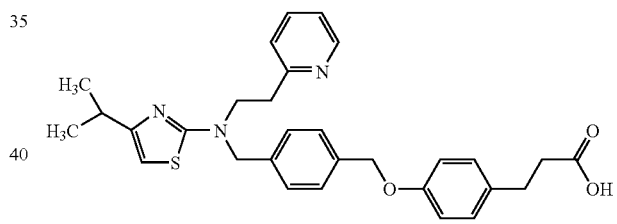

To a solution of 4-isopropyl-N-(2-pyridin-2-ylethyl)-1,3-thiazole-2-amine (127 mg) in N,N-dimethylformamide (2 mL) was added sodium hydride (20 mg), and the mixture was stirred at room temperature for 1 hr. Methyl 3-{4-([4-(chloromethyl)benzyl]oxy}phenyl)propanoate (159 mg) was added to the reaction mixture at room temperature, and the mixture was stirred at room temperature for 1 hr. The reaction mixture was poured into water and extracted with ethyl acetate. The ethyl acetate layer was dried using a Presep Dehydration tube (manufactured by Wako Pure Chemical Industries, Ltd.), and concentrated. The residue was purified by silica gel column chromatography (ethyl acetate:hexane=1:19-1:1 in volume ratio) to give a yellow oil. The oil was dissolved in methanol (5 mL), 2N aqueous sodium hydroxide solution (2 mL) was added, and the mixture was stirred at room temperature for 1 hr. The reaction mixture was diluted with water, neutralized with 1N hydrochloric acid, and extracted with ethyl acetate. The extract was dried using a Presep Dehydration tube (manufactured by Wako Pure Chemical Industries, Ltd.) and concentrated to give the title compound (105 mg, yield 41%) as colorless crystals.

MS: m/z 516 (M+H).

Example 16

3-(4-[(4-{[(4-isobutyl-1,3-thiazol-2-yl)(2-phenyl-ethyl)amino]methyl)benzyl)oxy]phenyl}propanoic acid

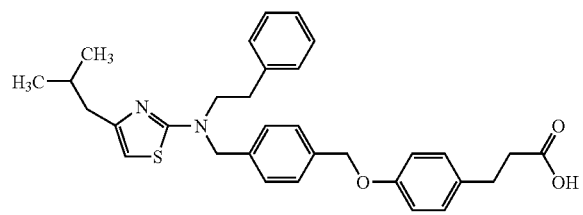

The title compound was synthesized in the same manner as in Example 15 from 4-isobutyl-N-(2-phenylethyl)-1,3-thiazole-2-amine (yield 45%). Colorless crystals.

MS: m/z 529 (M+H).

Example 17

3-{4-[(4-{[(3-phenylpropyl)(4-phenyl-1,3-thiazol-2-yl)amino]methyl}benzyl)oxy]phenyl}propanoic acid

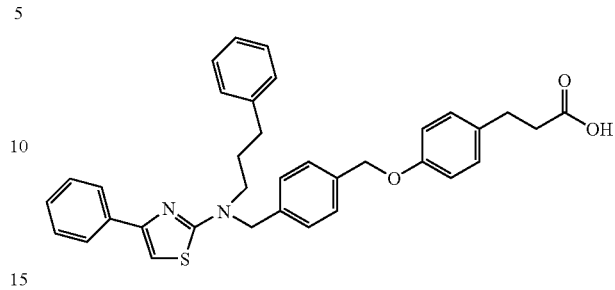

The title compound was synthesized in the same manner as in Example 15 from 4-phenyl-N-(3-phenylpropyl)-1,3-thiazole-2-amine (yield 41%). Pale-yellow crystals.

MS: m/z 563 (M+H).

Example 18 methyl 3-{4-[(4-{[(2-phenylethyl)(4-propyl-1,3-thiazol-2-yl)amino]methyl}benzyl)oxy]phenyl}propanoate

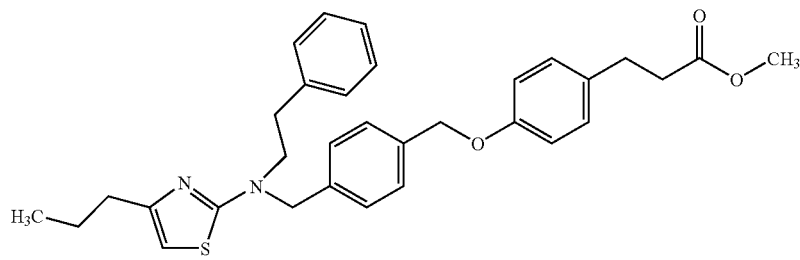

To a solution of N-(2-phenylethyl)-4-propyl-1,3-thiazole-2-amine (246 mg) in N,N-dimethylformamide (2 mL) was added sodium hydride (40 mg), and the mixture was stirred at room temperature for 1 hr. Methyl 3-(4-{[4-(chloromethyl)benzyl]-oxy}phenyl)propanoate (318 mg) was added to the reaction mixture at room temperature, and the mixture was stirred at room temperature for 1 hr. The reaction mixture was poured into water and extracted with ethyl acetate. The ethyl acetate layer was dried using a Presep Dehydration tube (manufactured by Wako Pure Chemical Industries, Ltd.), and concentrated. The residue was purified by silica gel column chromatography (ethyl acetate:hexane=1:19-1:1 in volume ratio) to give the title compound (380 mg) as a yellow oil.

MS: m/z 529 (M+H).

Example 19

3-{4-[(4-{[(2-phenylethyl)(4-propyl-1,3-thiazol-2-yl)amino]methyl}benzyl)oxy]phenyl}propanoic acid

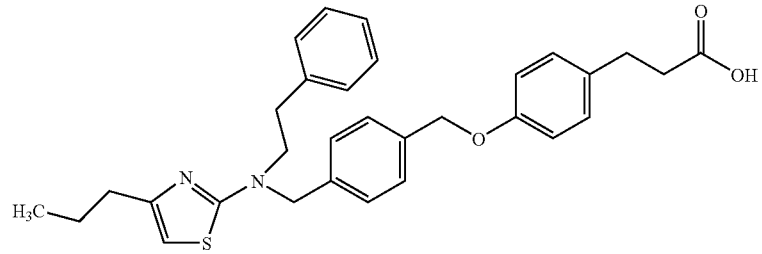

The title compound was synthesized in the same manner as in Example 9 from methyl 3-{4-[(4-{[(2-phenylethyl)(4-propyl-1,3-thiazol-2-yl)amino]methyl}benzyl)oxy]phenyl}propanoate by basic hydrolysis (yield 84%). Yellow oil.

MS: m/z 515 (M+H).

Example 20 methyl 3-{4-[(4-{[[3-(methylthio)propyl](4-phenyl-1,3-thiazol-2-yl)amino]methyl}benzyl)oxy]phenyl}propanoate

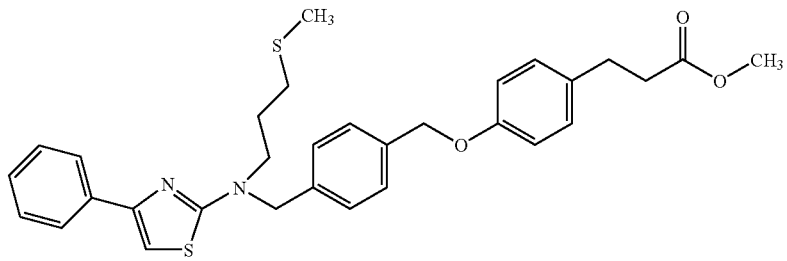

The title compound was synthesized in the same manner as in Example 18 from N-[3-(methylthio)propyl]-4-phenyl-1,3-thiazole-2-amine (yield 56%). Yellow oil.

$^1$H NMR (300 MHz, CDCl$_3$) δ ppm 1.90-2.02(2H, m), 2.08(3H, s), 2.42-2.72(4H, m), 2.89(2H, t, J=7.8 Hz), 3.54-3.64(2H, m), 3.66(3H, s), 4.78(2H, s), 5.02(2H, s), 6.71(1H, s), 6.82-6.94(2H, m), 7.11(2H, d, J=8.7 Hz), 7.18-7.55(7H, m), 7.74-7.97(2H, m).

Example 21

3-{4-[(4-{[[3-(methylthio)propyl](4-phenyl-1,3-thiazol-2-yl)amino]methyl}benzyl)oxy]phenyl}propanoic acid

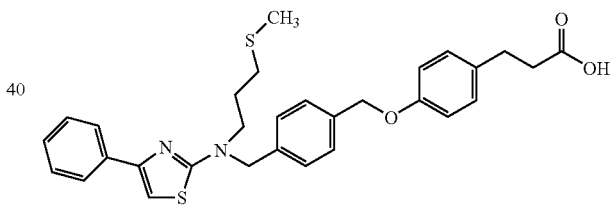

The title compound was synthesized in the same manner as in Example 9 from methyl 3-{4-[(4-{[[3-(methylthio)propyl](4-phenyl-1,3-thiazol-2-yl)amino]methyl}benzyl)oxy]phenyl}-propanoate by basic hydrolysis (yield 89%). Yellow oil.

MS: m/z 533 (M+H).

Example 22 methyl 3-{4-[(4-{[[3-(methylsulfinyl)propyl](4-phenyl-1,3-thiazol-2-yl)amino]methyl}benzyl)oxy]phenyl}-propanoate

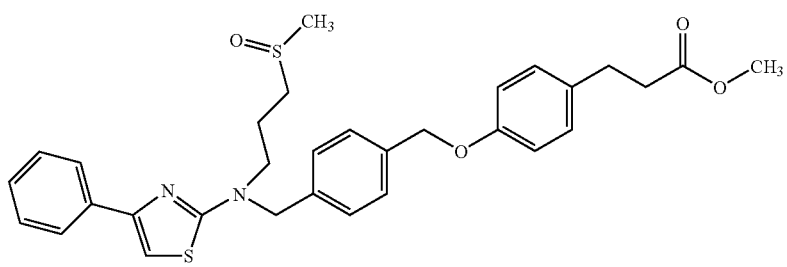

A mixture of methyl 3-{4-[(4-{[[3-(methylthio)propyl](4-phenyl-1,3-thiazol-2-yl)amino]methyl}benzyl)oxy]phenyl}-propanoate (280 mg), m-chloroperbenzoic acid (122 mg) and tetrahydrofuran (10 mL) was stirred at room temperature for 3 hr. The reaction mixture was concentrated and the residue was purified by silica gel column chromatography (ethyl acetate:hexane=1:19-1:0 in volume ratio) to give the title compound (180 mg, yield 62%) as a yellow oil.

MS: m/z 563 (M+H).

Example 23 methyl 3-{4-[(4-{[[3-(methylsulfonyl)propyl](4-phenyl-1,3-thiazol-2-yl)amino]methyl}benzyl)oxy]phenyl}-propanoate

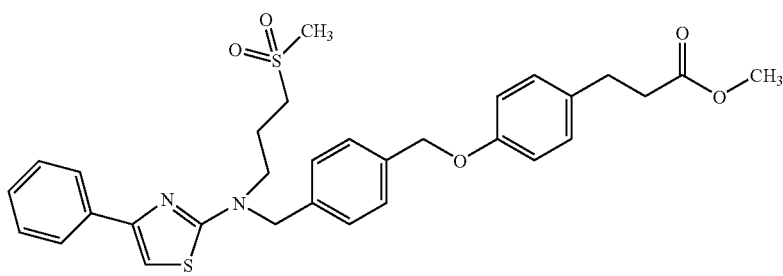

A mixture of methyl 3-{4-[(4-([[3-(methylthio)propyl](4-phenyl-1,3-thiazol-2-yl)amino]methyl)benzyl)oxy]phenyl}-propanoate (200 mg), m-chloroperbenzoic acid (263 mg) and tetrahydrofuran (10 mL) was stirred at room temperature for 3 hr. The reaction mixture was concentrated, and the residue was purified by silica gel column chromatography (ethyl acetate:hexane=1:19-1:0 in volume ratio) to give the title compound (141 mg, yield 67%) as a yellow oil.

MS: m/z 579 (M+H).

Example 24

3-{4-[(4-{[[3-(methylsulfinyl)propyl](4-phenyl-1,3-thiazol-2-yl)amino]methyl}benzyl)oxy]phenyl}propanoic acid

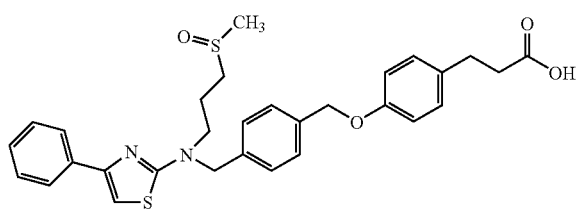

The title compound was synthesized in the same manner as in Example 9 from methyl 3-{4-[(4-{[[3-(methylsulfinyl)propyl](4-phenyl-1,3-thiazol-2-yl)amino]methyl}benzyl)oxy]phenyl}propanoate by basic hydrolysis (yield 75%). Colorless crystals.

MS: m/z 549 (M+H).

Example 25

3-{4-[(4-{[[3-(methylsulfonyl)propyl](4-phenyl-1,3-thiazol-2-yl)amino]methyl}benzyl)oxy]phenyl}propanoic acid

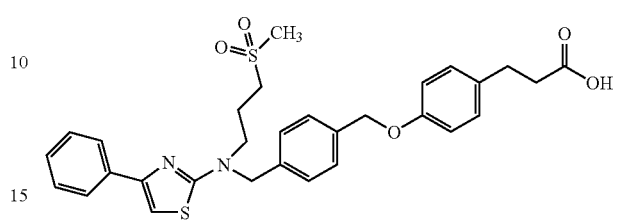

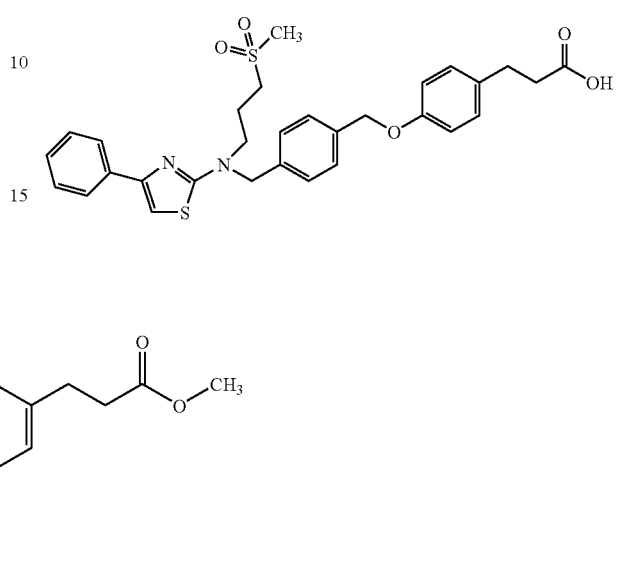

The title compound was synthesized in the same manner as in Example 9 from methyl 3-{4-[(4-{[[3-(methylsulfonyl)propyl](4-phenyl-1,3-thiazol-2-yl)amino]methyl}benzyl)oxy]-phenyl}propanoate by basic hydrolysis (yield 77%). Colorless crystals.

MS: m/z 565 (M+H).

Example 26

3-{2-fluoro-4-[(4-{[[2-(2-fluorophenyl)ethyl](4-isopropyl-1,3-thiazol-2-yl)amino]methyl}benzyl)oxy]phenyl}-propanoic acid

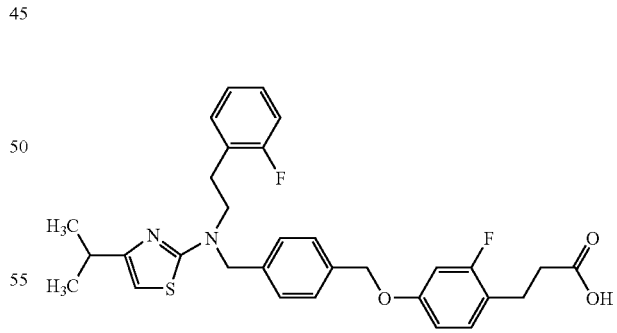

To a solution of N-[2-(2-fluorophenyl)ethyl]-4-isopropyl-1,3-thiazole-2-amine (139 mg) in N,N-dimethylformamide (2 mL) was added sodium hydride (20 mg), and the mixture was stirred at room temperature for 1 hr. Ethyl 3-(4-{[4-(chloromethyl)benzyl]oxy}-2-fluorophenyl)propanoate (175 mg) was added to the reaction mixture at room temperature, and the mixture was stirred at room temperature for 1 hr. The reaction mixture was poured into water and extracted with ethyl acetate. The ethyl acetate layer was dried using a Presep Dehydration tube (manufactured by Wako Pure Chemical Industries, Ltd.), and concentrated. The residue was purified by silica gel column chromatography (ethyl acetate:hexane=1:19-1:1 in volume ratio) to give a yellow oil. This oil was dissolved in ethanol (5 mL), 2N aqueous sodium hydroxide solution (2 mL) was added, and the mixture was stirred at room temperature for 1 hr. The reaction mixture was diluted with water, neutralized with 1N hydrochloric acid, and extracted with ethyl acetate. The extract was dried using a Presep Dehydration tube (manufactured by Wako Pure Chemical Industries, Ltd.) and concentrated to give the title compound (206 mg, yield 71%) as a yellow oil.

MS: m/z 551 (M+H).

Example 27

3-{2-fluoro-4-[(4-{[[2-(4-fluorophenyl)ethyl](4-isobutyl-1,3-thiazol-2-yl)amino]methyl}benzyl)oxy]phenyl}propanoic acid

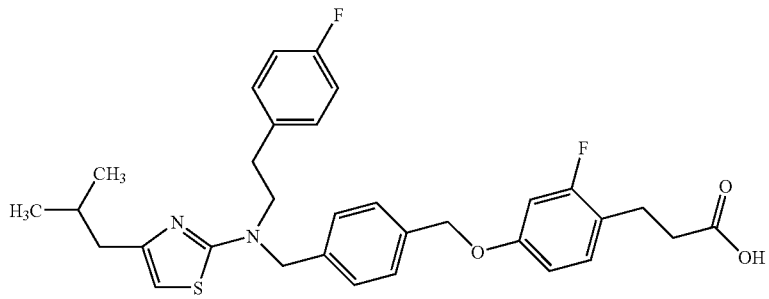

The title compound was synthesized in the same manner as in Example 26 from N-[2-(4-fluorophenyl)ethyl]-4-isobutyl-1,3-thiazole-2-amine (yield 33%). Yellow oil.

MS: m/z 565 (M+H).

Example 28 methyl 3-{4-[(4-{[(4-isopropyl-1,3-thiazol-2-yl)(2-phenylethyl)amino]methyl}benzyl)oxy]phenyl}propanoate

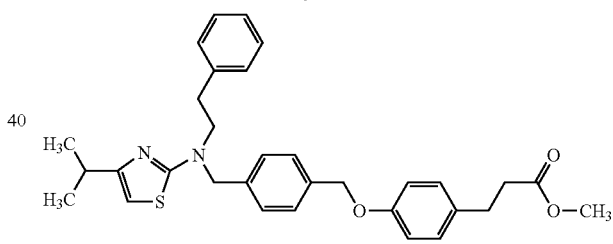

The title compound was synthesized in the same manner as in Example 18 from 4-isopropyl-N-(2-phenylethyl)-1,3-thiazole-2-amine (yield 68%). Yellow oil.

MS: m/z 529 (M+H).

Example 29 methyl 3-{4-[(4-{[(2-phenylethyl)(4-pyridin-2-yl-1,3-thiazol-2-yl)amino]methyl}benzyl)oxy]phenyl}propanoate

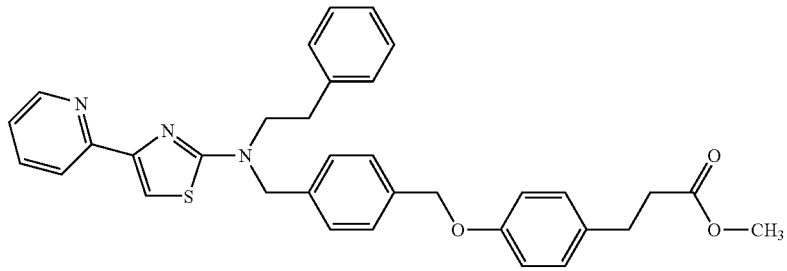

The title compound was synthesized in the same manner as in Example 18 from N-(2-phenylethyl)-4-pyridin-2-yl-1,3-thiazole-2-amine (yield 92%). Yellow oil.

MS: m/z 564 (M+H).

Example 30

3-{4-[(4-{[[4-(4-chlorophenyl)-5-methyl-1,3-oxazol-2-yl](ethyl)amino]methyl}benzyl)oxy]phenyl}propanoic acid

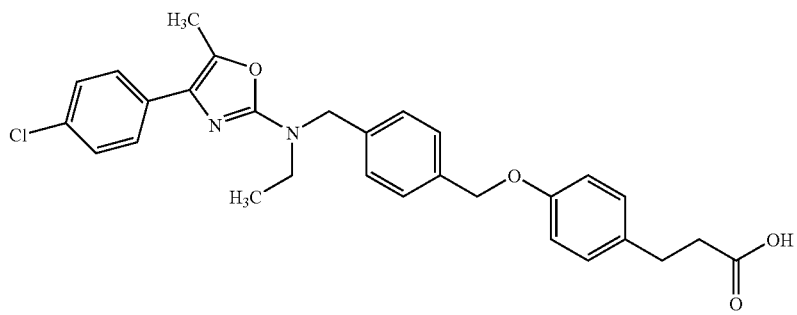

To a solution of methyl 3-(4-{[4-(chloromethyl)benzyl]-oxy}phenyl)propanoate (50 mg, 0.16 mmol) in N,N-dimethylformamide (1 mL) were added a solution of 4-(4-chlorophenyl)-N-ethyl-5-methyl-1,3-oxazole-2-amine (45 mg, 0.19 mmol) in N,N-dimethylformamide (0.5 mL) and potassium carbonate (33 mg, 0.24 mmol), and the mixture was stirred at 70° C. for 66 hr. Water (2 mL) was added to the reaction mixture and the mixture was extracted with dichloromethane (2 mL). The organic layer was concentrated under reduced pressure with a centrifugal concentration apparatus (GeneVac). The obtained resultant product was dissolved in methanol (2 mL), 1N aqueous sodium hydroxide solution (0.32 mL, 0.32 mmol) was added, and the mixture was stirred at room temperature for 18 hr. The reaction mixture was acidified with 1N hydrochloric acid, and extracted with dichloromethane (2 mL). The organic layer was concentrated under reduced pressure with a centrifugal concentration apparatus (GeneVac). The residue was purified by preparative HPLC (gradient cycle B) to give the title compound (4.6 mg, yield 5%).

MS: m/z 505 (M+H).

Example 31 methyl 3-[4-[[4-[[(2-phenylethyl)(4-phenyl-1,3-thiazol-2-yl)amino]methyl]benzyl]oxy]phenyl]propanoate

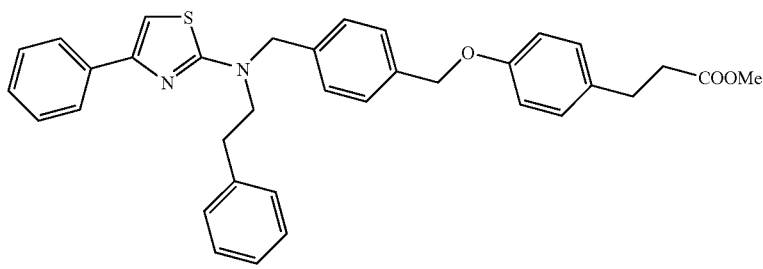

To a solution of [4-[[(2-phenylethyl)(4-phenyl-1,3-thiazol-2-yl)amino]methyl]phenyl]methanol (409 mg, 0.98 mmol), methyl 3-(4-hydroxyphenyl)propanoate (195 mg, 1.18 mmol) and tributylphosphine (297 mg, 1.47 mmol) in tetrahydrofuran (20 mL) was added 1,1'-(azodicarbonyl)dipiperidine (371 mg, 1.47 mmol), and the mixture was stirred at room temperature for 16 hr. The insoluble materials were filtered off and the filtrate was concentrated. The residue was purified by silica gel column chromatography to give the title compound (273 mg, yield 50%) as a colorless oil.

$^1$H NMR (CDCl$_3$) δ ppm 2.59(t, J=7.7 Hz, 2H), 2.88(t, J=7.7 Hz, 2H), 2.99(t, J=7.5 Hz, 2H), 3.66-3.71(m, 5H), 4.66(s, 2H), 5.01(s, 2H), 6.74(s, 1H), 6.88-6.91(m, 2H), 7.10 (d, J=8.5 Hz, 2H), 7.19-7.41(m, 12H), 7.87-7.90(m, 2H).

Example 32

3-[4-[[4-[[(2-phenylethyl)(4-phenyl-1,3-thiazol-2-yl)amino]methyl]benzyl]oxy]phenyl]propanoic acid

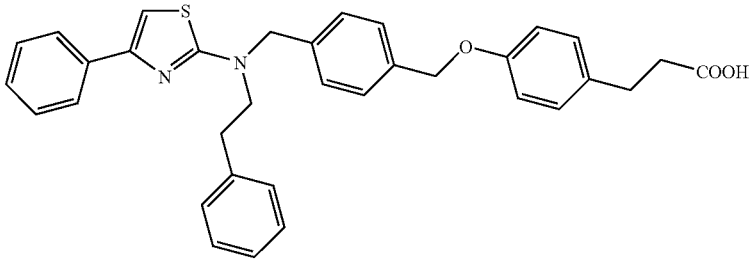

A mixture of methyl 3-[4-[[4-[[(2-phenylethyl)(4-phenyl-1,3-thiazol-2-yl)amino]methyl]benzyl]oxy]phenyl]propanoate (270 mg, 0.480 mmol), tetrahydrofuran (15 mL), methanol (10 mL), water (10 mL) and lithium hydroxide monohydrate (60.4 mg, 1.44 mmol) was stirred at room temperature for 3 hr. The reaction mixture was neutralized with 1N hydrochloric acid, and extracted with ethyl acetate. The organic layer was washed with saturated brine and dried over magnesium sulfate, and the solvent was evaporated under reduced pressure. The residue was recrystallized from ethyl acetate-hexane to give the title compound (162 mg, yield 62%) as colorless crystals.

MS: m/z 549 (M+H). melting point: 114-115° C. $^1$H NMR (CDCl$_3$) δ 2.64(t, J=7.7 Hz, 2H), 2.90(t, J=7.6 Hz, 2H), 2.99 (t, J=7.8 Hz, 2H), 3.68(t, J=7.8 Hz, 2H), 4.66(s,2H), 5.01(s, 2H), 6.74(s, 1H), 6.89(d, J=8.7 Hz, 2H), 7.11(d, J=8.7 Hz, 2H), 7.19-7.41(m, 12H), 7.87-7.90(m, 2H).

Example 33

3-[4-[[4-[[(2-phenylethyl)(4-phenyl-1,3-thiazol-2-yl)amino]methyl]benzyl]oxy]phenyl]propanoic acid 0.5 calcium salt

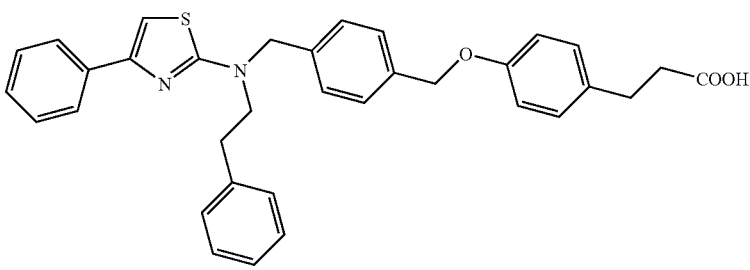

0.5 Ca salt

To a solution of 3-[4-[[4-[[(2-phenylethyl)(4-phenyl-1,3-thiazol-2-yl)amino]methyl]benzyl]oxy]phenyl]propanoic acid (150 mg, 0.274 mmol) in methanol (10 mL) was added 2N aqueous sodium hydroxide solution (0.27 mL, 0.54 mmol). The mixture was stirred and concentrated under reduced pressure. The residue was dissolved in water (15 mL), aqueous calcium chloride solution (0.137 M, 2 mL, 0.274 mmol) was added dropwise and the mixture was stirred. The crystals were collected by filtration, and the obtained crude crystals were washed with water and hexane. The crystals were recrystallized from diisopropyl ether-hexane to give the title compound (128 mg, yield 78%) as a white powder.

elemental analysis value for $C_{68}H_{62}N_4S_2O_6Ca \cdot 3.0H_2O$
Calculated: C, 68.66; H, 5.76; N, 4.71. Found: C, 68.86; H, 5.85; N, 4.60.

Example 34

3-[4-[[4-[[(2-phenylethyl)(4-phenyl-1,3-thiazol-2-yl)amino]methyl]benzyl]oxy]phenyl]propanoic acid (5-methyl-2-oxo-1,3-dioxol-4-yl)methyl ester

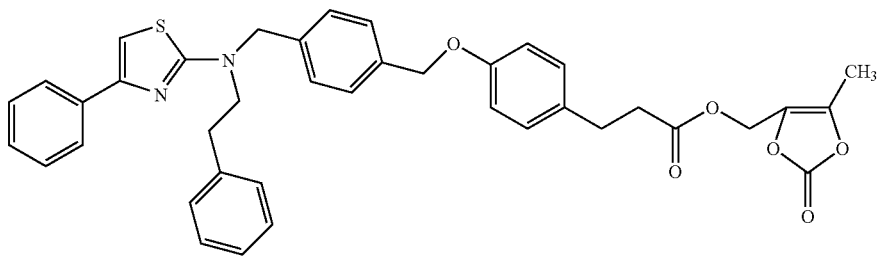

A solution of 3-[4-[[4-[[(2-phenylethyl)(4-phenyl-1,3-thiazol-2-yl)amino]methyl]benzyl]oxy]phenyl]propanoic acid (450 mg, 0.82 mmol), 4-(chloromethyl)-5-methyl-1,3-dioxol-2-one (146 mg, 0.99 mmol) and potassium carbonate (170 mg, 1.23 mmol) in N,N-dimethylformamide (10 mL) was stirred at room temperature for 5 hr. The reaction mixture was poured into water and extracted with ethyl acetate. The organic layer was washed with saturated brine and dried over anhydrous magnesium sulfate. The solvent was evaporated under reduced pressure. The residue was purified by silica gel column chromatography to give the title compound (175 mg, yield 32%) as a colorless oil.

$^1$H NMR (CDCl$_3$) δ 2.12(3H, s), 2.63(2H, t, J=7.5 Hz), 2.89(2H, t, J=7.5 Hz), 2.94-3.03(2H, m), 3.62-3.72(2H, m), 4.66(2H, s), 4.80(2H, s), 5.01(2H, s), 6.74(1H, s), 6.84-6.91 (2H, m), 7.08(2H, d, J=8.7 Hz), 7.19-7.41(12H, m), 7.84-7.91 (2H, m).

Example 35 ethyl 3-[2-fluoro-4-[[4-[[(2-phenylethyl)(4-phenyl-1,3-thiazol-2-yl)amino]methyl]benzyl]oxy]phenyl]propanoate

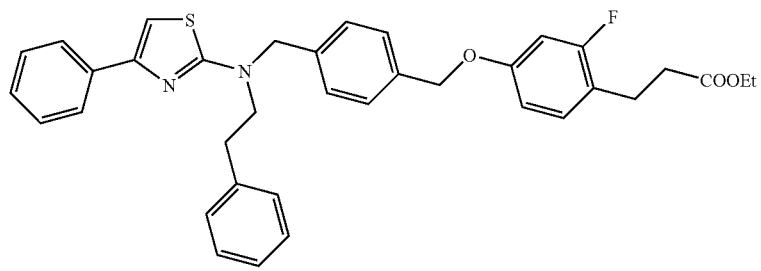

The title compound was obtained as a colorless oil in the same manner as in Example 31 from ethyl 3-(2-fluoro-4-hydroxyphenyl)propanoate and [4-[[(2-phenylethyl)(4-phenyl-1,3-thiazol-2-yl)amino]methyl]phenyl]methanol (yield 51%).

$^1$H NMR (CDCl$_3$) δ 1.20-1.28(3H, m), 2.57(2H, t, J=7.6 Hz), 2.89(2H, t, J=7.5 Hz), 3.00(2H, t, J=7.7 Hz), 3.63-3.73 (2H, m), 4.08-4.16(2H, m), 4.66(2H, s), 4.99(2H, s), 6.61-6.70(2H, m), 6.74(1H, s), 7.08(1H, t, J=8.8 Hz), 7.19-7.41 (12H, m), 7.88(2H, d, J=7.4 Hz).

Example 36

3-[2-fluoro-4-[[4-[[(2-phenylethyl)(4-phenyl-1,3-thiazol-2-yl)amino]methyl]benzyl]oxy]phenyl]propanoic acid

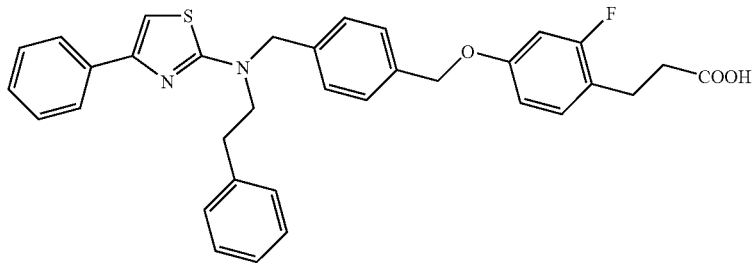

The title compound was obtained as colorless crystals in the same manner as in Example 32 from ethyl 3-[2-fluoro-4-[[4-[[(2-phenylethyl)(4-phenyl-1,3-thiazol-2-yl)amino]methyl]benzyl]oxy]phenyl]propanoate (yield 39%).

$^1$H NMR (CDCl$_3$) δ 2.63(t, J=7.5 Hz, 2H), 2.90(t, J=7.5 Hz, 2H), 2.99(t, J=8.1 Hz, 2H), 3.68(t, J=8.1 Hz, 2H), 4.66(s, 2H), 4.99(s, 2H), 6.63-6.99(m, 2H), 6.74(s, 1H), 7.09(t, J=8.8 Hz, 1H), 7.19-7.41(m, 12H), 7.87-7.90(m, 2H).

Example 37 methyl 3-[4-[[3-[[(2-phenylethyl)(4-phenyl-1,3-thiazol-2-yl)amino]methyl]benzyl]oxy]phenyl]propanoate

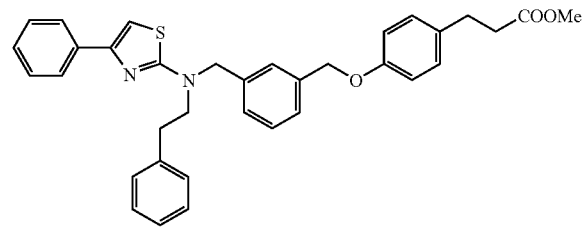

The title compound was obtained as a colorless oil in the same manner as in Example 31 from methyl 3-(4-hydroxyphenyl)propanoate and [3-[[(2-phenylethyl)(4-phenyl-1,3-thiazol-2-yl)amino]methyl]phenyl]methanol (yield 87%).

$^1$H NMR (CDCl$_3$) δ 2.58(2H, t, J=7.8 Hz), 2.87(2H, t, J=7.8 Hz), 2.98(2H, t, J=7.2 Hz), 3.60-3.73(5H, m), 4.66(2H, s), 5.01(2H, s), 6.74(1H, s), 6.87(2H, d, J=8.7 Hz), 7.08(2H, d, J=8.5 Hz), 7.15-7.43(12H, m), 7.89(2H, d, J=7.4 Hz).

Example 38

3-[4-[[3-[[(2-phenylethyl)(4-phenyl-1,3-thiazol-2-yl)amino]methyl]benzyl]oxy]phenyl]propanoic acid

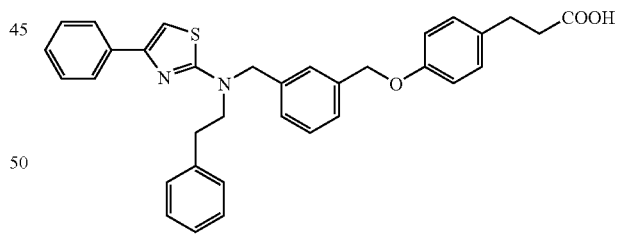

The title compound was obtained as colorless crystals in the same manner as in Example 32 from methyl 3-[4-[[3-[[(2-phenylethyl)(4-phenyl-1,3-thiazol-2-yl)amino]methyl]benzyl]oxy]phenyl]propanoate (yield 39%).

$^1$H NMR (CDCl$_3$) δ 2.62(2H, t, J=7.7 Hz), 2.87(2H, t, J=7.7 Hz), 2.97(2H, t, J=7.5 Hz), 3.67(2H, t, J=7.5 Hz), 4.66(2H, s), 5.01(2H, s), 6.74(1H, s), 6.87(2H, d, J=8.5 Hz), 7.08(2H, d, J=8.5 Hz), 7.16-7.44(12H, m), 7.88(2H, d, J=7.4 Hz).

Example 39 methyl 3-[4-[[4-[[(5-methyl-4-phenyl-1,3-oxazol-2-yl)(propyl)amino]methyl]benzyl]oxy]phenyl]propanoate

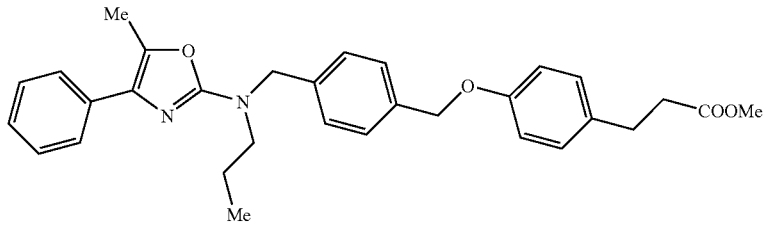

To a solution of 5-methyl-4-phenyl-N-propyl-1,3-oxazole-2-amine (407 mg, 1.88 mmol) in N,N-dimethylformamide (10 mL) was added sodium hydride (60% in oil, 82 mg, 2.04 mmol) at room temperature and the mixture was stirred for 30 min. Methyl 3-[4-[[4-(chloromethyl)benzyl]oxy]phenyl]propanoate (500 mg, 1.57 mmol) was added to the reaction mixture and the mixture was stirred at room temperature for 4 hr. The reaction mixture was poured into water and extracted with ethyl acetate. The organic layer was washed with saturated brine and dried over anhydrous magnesium sulfate. The solvent was evaporated under reduced pressure. The residue was purified by silica gel column chromatography to give the title compound (251 mg, yield 32%) as a pale-yellow oil.

$^1$H NMR (CDCl$_3$) δ 0.90(t, J=7.2 Hz, 3H), 1.58-1.75(m, 2H), 2.43(s, 3H), 2.59(t, J=7.7 Hz, 2H), 2.89(t, J=7.7 Hz, 2H), 3.31-3.35(m, 2H), 3.66(s, 3H), 4.67(2H, s), 5.02(s, 2H), 6.89 (d, J=8.4 Hz, 2H), 7.11(d, J=8.4 Hz, 2H), 7.22-7.43(m, 7H), 7.58-7.65(m, 2H).

Example 40

3-[4-[[4-[[(5-methyl-4-phenyl-1,3-oxazol-2-yl)(propyl)amino]methyl]benzyl]oxy]phenyl]propanoic acid

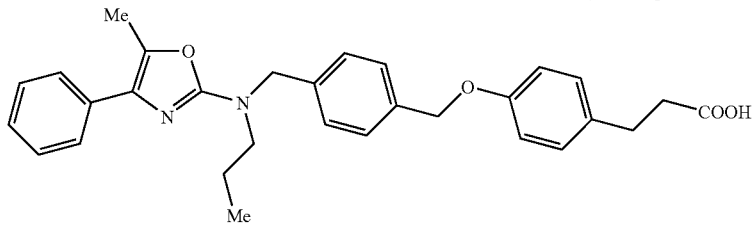

The title compound was obtained a pale-yellow oil in the same manner as in Example 32 from methyl 3-[4-[[4-[[(5-methyl-4-phenyl-1,3-oxazol-2-yl)(propyl)amino]methyl]benzyl]-oxy]phenyl]propanoate (yield 17%).

$^1$H NMR (CDCl$_3$) δ 0.89(t, J=7.5 Hz, 3H), 1.57-1.70(m, 2H), 2.42(s, 3H), 2.62(t, J=7.6 Hz, 2H), 2.88(t, J=7.6 Hz, 2H), 3.30-3.35(m, 2H), 4.67(s, 2H), 5.02(s, 2H), 6.87-6.90(m, 2H), 7.10-7.13(m, 2H), 7.22-7.41(m, 7H), 7.61-7.64(m, 2H).

Example 41 ethyl 3-[2,6-difluoro-4-[[4-[[(2-phenylethyl)(4-phenyl-1,3-thiazol-2-yl)amino]methyl]benzyl]oxy]phenyl]-propanoate

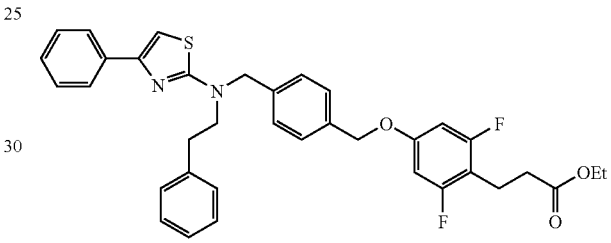

The title compound (300 mg, yield 56%) was obtained as a colorless oil in the same manner as in Example 31 from ethyl 3-(2,6-difluoro-4-hydroxyphenyl)propanoate (200 mg, 0.87 mmol).

That is, to a solution of [4-[[(2-phenylethyl)(4-phenyl-1,3-thiazol-2-yl)amino]methyl]phenyl]methanol (350 mg, 0.87 mmol), ethyl 3-(2,6-difluoro-4-hydroxyphenyl)propanoate (200 mg, 0.87 mmol) and tributylphosphine (0.31 mL, 1.24 mmol) in tetrahydrofuran (30 mL) was added 1,1'-(azodicarbonyl)dipiperidine (320 mg, 1.27 mmol), and the mixture was stirred at room temperature for 18 hr. The insoluble materials were filtered off and the filtrate was concentrated. The residue was purified by silica gel column chromatography to give the title compound (300 mg, yield 56%) as a colorless oil.

MS: m/z 613 (M+H). $^1$H NMR (CDCl$_3$) δ 1.23(3H, t, J=7.2 Hz), 2.54(2H, t, J=7.6 Hz), 2.91(2H, t, J=7.6 Hz), 3.00(2H, t, J=7.6 Hz), 3.69(2H, t, J=7.6 Hz), 4.12(2H, q, J=7.2 Hz), 4.66(2H, s), 4.97(2H, s), 6.47(2H, d, J=9.4 Hz), 6.75(1H, s), 7.17-7.44(12H, m), 7.89(2H, d, J=8.0 Hz).

Example 42

3-[2,6-difluoro-4-[[4-[[(2-phenylethyl)(4-phenyl-1,3-thiazol-2-yl)amino]methyl]benzyl]oxy]phenyl]propanoic acid

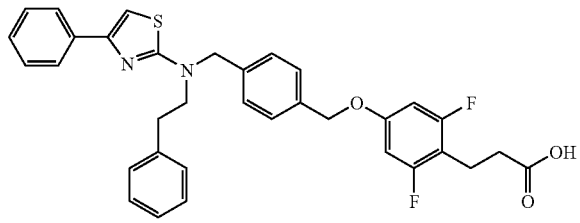

The title compound (271 mg, yield 94%) was obtained as colorless prism crystals from ethyl 3-[2,6-difluoro-4-[[4-[[(2-phenylethyl)(4-phenyl-1,3-thiazol-2-yl)amino]methyl]benzyl]oxy]phenyl]propanoate (300 mg, 0.49 mmol) in the same manner as in Example 2.

That is, ethyl 3-[2,6-difluoro-4-[[4-[[(2-phenylethyl)(4-phenyl-1,3-thiazol-2-yl)amino]methyl]benzyl]oxy]phenyl]-propanoate (300 mg, 0.49 mmol) was dissolved in a mixed solvent of tetrahydrofuran (8 mL) and ethanol (8 mL). Thereto was added an aqueous solution (5 mL) of 85% potassium hydroxide (100 mg, 1.51 mmol), and the mixture was stirred at room temperature for 18 hr. The reaction solution was diluted with ethyl acetate, washed successively with aqueous citric acid solution, water and saturated brine, dried over anhydrous magnesium sulfate, and concentrated under reduced pressure. The residue was purified by silica gel column chromatography, and crystallized from diethyl ether-hexane to give the title compound (271 mg, yield 94%) as colorless prism crystals.

MS: m/z 585 (M+H). $^1$H NMR (CDCl$_3$) δ2.60(2H, t, J=7.6 Hz), 2.93(2H, t, J=7.6 Hz), 2.99(2H, t, J=7.6 Hz), 3.69(2H, t, J=7.6 Hz), 4.67(2H, s), 4.98(2H, s), 6.58(2H, d, J=9.6 Hz), 6.75(1H, s), 7.16-7.43(12H, m), 7.84-7.93(2H, m).

Example 43 ethyl 3-[2-fluoro-4-({4-[((2-phenylethyl){4-[4-(trifluoromethyl)phenyl]-1,3-thiazol-2-yl}amino)methyl]-benzyl}oxy)phenyl]propanoate

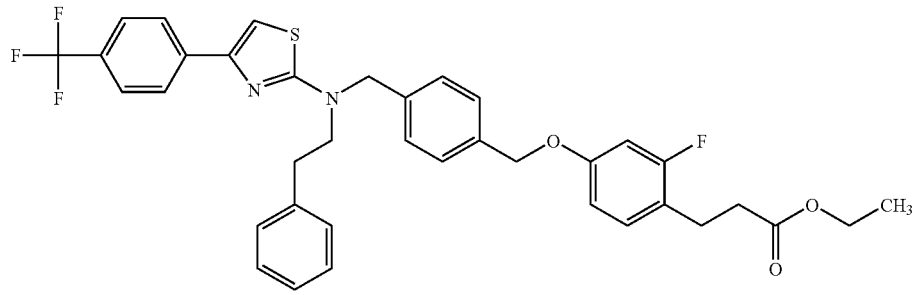

To a solution of N-(2-phenylethyl)-4-[4-(trifluoromethyl)phenyl]-1,3-thiazole-2-amine (500 mg, 1.43 mmol) in N,N-dimethylformamide (5 mL) was added sodium hydride (50 mg, in oil, 1.3 mmol) at room temperature, and the mixture was stirred at room temperature for 1 hr. Ethyl 3-(4-{[4-(chloromethyl)benzyl]oxy}-2-fluorophenyl)propanoate (350 mg, 1.0 mmol) was added, and the mixture was further stirred at room temperature for 2 hr. The reaction mixture was poured into 1N hydrochloric acid, and the mixture was extracted with ethyl acetate. The organic layer was concentrated. The residue was purified by silica gel column chromatography (ethyl acetate:hexane=1:19-3:2 in volume ratio) to give the title compound as a yellow oil.

MS: m/z 663 (M+H).

Example 44

3-[2-fluoro-4-({4-[((2-phenylethyl){4-[4-(trifluoromethyl)phenyl]-1,3-thiazol-2-yl}amino)methyl]-benzyl}oxy)phenyl]propanoic acid

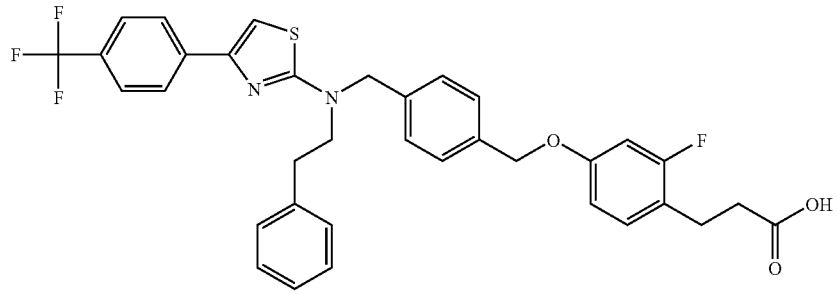

The yellow oil obtained in Example 43 was dissolved in a mixed solvent of ethanol (5 mL) and tetrahydrofuran (5 mL), and 2N aqueous sodium hydroxide solution (2 mL) was added. The mixture was stirred at room temperature for 2 hr. The reaction mixture was diluted with water and neutralized with 1N hydrochloric acid. The precipitated solid was collected by filtration, washed with water and dried to give the title compound (300 mg, yield 47%, 2 steps) as colorless crystals.

MS: m/z 635 (M+H).

Example 45

3-(2-fluoro-4-{[4-({[2-(4-fluorophenyl)ethyl][4-(4-fluorophenyl)-1,3-thiazol-2-yl]amino}methyl)benzyl]oxy}-phenyl)propanoic acid

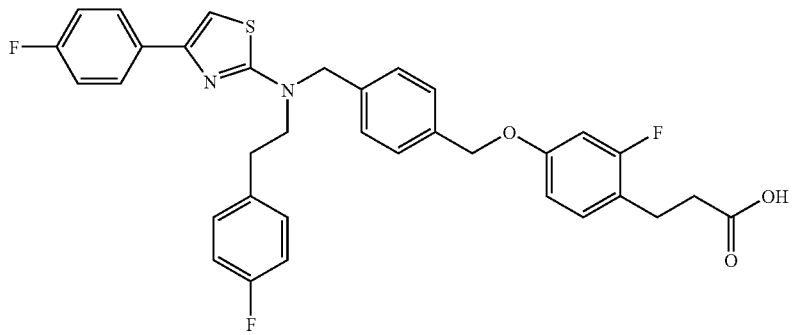

A mixture of 2-bromo-1-(4-fluorophenyl)ethanone (217 mg, 1.0 mmol), N-[2-(4-fluorophenyl)ethyl]thiourea (198 mg, 1.0 mmol) and N,N-dimethylformamide (5 mL) was stirred at room temperature for 1 hr. Sodium hydride (100 mg, in oil, 2.5 mmol) was added to the reaction mixture at room temperature, and the mixture was stirred at room temperature for 1 hr. Ethyl 3-(4-{[4-(chloromethyl)benzyl]oxy}-2-fluorophenyl)propanoate (350 mg, 1.0 mmol) was added, and the mixture was further stirred at room temperature for 2 hr. The reaction mixture was poured into 1N hydrochloric acid and the mixture was extracted with ethyl acetate. The organic layer was concentrated. The residue was purified by silica gel column chromatography (ethyl acetate:hexane=1:19-3:2 in volume ratio) to give a yellow oil. The oil was dissolved in a mixed solvent of ethanol (5 mL) and tetrahydrofuran (5 mL), and 2N aqueous sodium hydroxide solution (2 mL) was added. The mixture was stirred at room temperature for 2 hr. The reaction mixture was poured into 1N hydrochloric acid, and the mixture was extracted with ethyl acetate. The organic layer was dried over anhydrous magnesium sulfate and concentrated to give the title compound (264 mg, yield 44%, 3 steps) as a pale-green oil.

MS: m/z 603 (M+H).

Example 46

3-[4-({4-[([2-(4-fluorophenyl)ethyl]{4-[4-(trifluoromethyl)phenyl]-1,3-thiazol-2-yl}amino)methyl]-benzyl}oxy)phenyl]propanoic acid

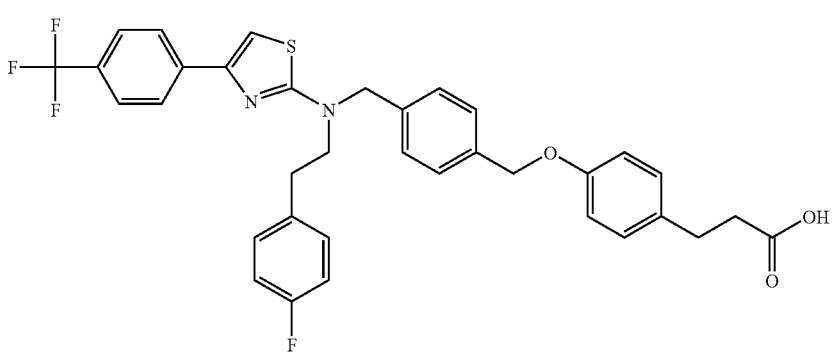

To a solution of N-[2-(4-fluorophenyl)ethyl]-4-[4-(trifluoromethyl)phenyl]-1,3-thiazole-2-amine (400 mg, 1.09 mmol) in N,N-dimethylformamide (5 mL) was added sodium hydride (50 mg, in oil, 1.3 mmol) at room temperature, and the mixture was stirred at room temperature for 1 hr. Methyl 3-(4-{[4-(chloromethyl)benzyl]oxy}phenyl)propanoate (318 mg, 1.0 mmol) was added, and the mixture was further stirred at room temperature for 1 hr. The reaction mixture was poured into 1N hydrochloric acid and extracted with ethyl acetate. The organic layer was concentrated. The residue was purified by silica gel column chromatography (ethyl acetate:hexane=1:19-1:1 in volume ratio) to give a yellow oil. The oil was dissolved in a mixed solvent of ethanol (5 mL) and tetrahydrofuran (5 mL), and 2N aqueous sodium hydroxide solution (2 mL) was added. The mixture was stirred at room temperature for 2 hr. The reaction mixture was diluted with water and neutralized with 1N hydrochloric acid. The precipitated solid was collected by filtration, washed with water and dried to give the title compound (109 mg, yield 17%, 2 steps) as colorless crystals.

MS: m/z 635 (M+H).

Example 47

3-[2-fluoro-4-({4-[([2-(4-fluorophenyl)ethyl]{4-[4-(trifluoromethyl)phenyl]-1,3-thiazol-2-yl}amino)methyl]-benzyl}oxy)phenyl]propanoic acid

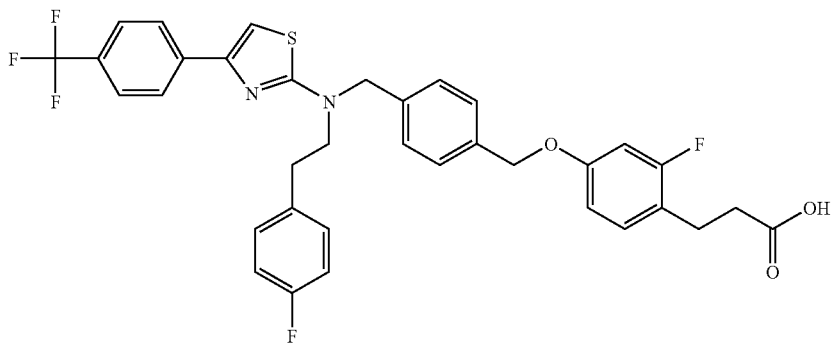

To a solution of N-[2-(4-fluorophenyl)ethyl]-4-[4-(trifluoromethyl)phenyl]-1,3-thiazole-2-amine (500 mg, 1.36 mmol) in N,N-dimethylformamide (5 mL) was added sodium hydride (40 mg, in oil, 1.0 mmol) at room temperature, and the mixture was stirred at room temperature for 1 hr. Ethyl 3-(4-{[4-(chloromethyl)benzyl]oxy}-2-fluorophenyl)propanoate (350 mg, 1.0 mmol) was added, and the mixture was further stirred at room temperature for 1 hr. The reaction mixture was poured into 1N hydrochloric acid and extracted with ethyl acetate. The organic layer was concentrated. The residue was purified by silica gel column chromatography (ethyl acetate:hexane=1:19-1:1 in volume ratio) give a yellow oil. The oil was dissolved in a mixed solvent of ethanol (5 mL) and tetrahydrofuran (5 mL), and 2N aqueous sodium hydroxide solution (2 mL) was added. The mixture was stirred at room temperature for 2 hr. The reaction mixture was poured into 1N hydrochloric acid, and the mixture was extracted with ethyl acetate. The organic layer was concentrated, and the residue was purified by preparative HPLC. The obtained fraction was concentrated, neutralized with 10% aqueous sodium hydrogencarbonate solution and extracted with ethyl acetate. The ethyl acetate layer was filtered with a Presep Dehydration tube (manufactured by Wako Pure Chemical Industries, Ltd.) and concentrated to give the title compound (139 mg, yield 21%, 2 steps) as a yellow oil.

MS: m/z 653 (M+H).

Example 48

3-(4-{[4-({(2-phenylethyl)[4-(trifluoromethyl)-1,3-thiazol-2-yl]amino}methyl)benzyl]oxy}phenyl)propanoic acid

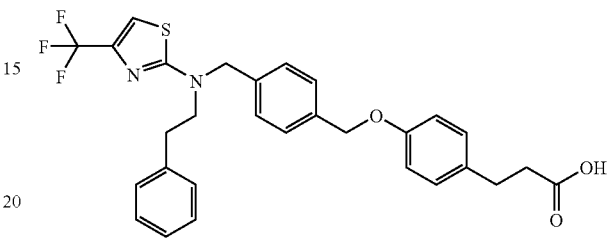

The title compound was obtained in the same manner as in Example 47 from N-(2-phenylethyl)-4-(trifluoromethyl)-1,3-thiazole-2-amine and methyl 3-(4-{[4-(chloromethyl)benzyl]oxy}phenyl)propanoate (yield 27%, 2 steps).

MS: m/z 541 (M+H).

Example 49

3-{4-[(4-{(2-phenylethyl)[(4-phenyl-1,3-thiazol-2-yl)methyl]amino}benzyl)oxy]phenyl}propanoic acid

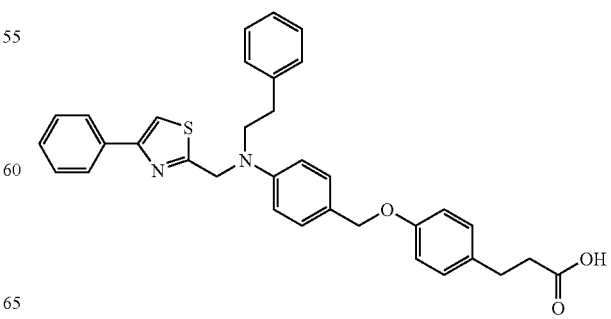

To a mixture of 4-phenyl-1,3-thiazole-2-carbaldehyde (380 mg, 2.0 mmol), methyl 3-{4-[(4-aminobenzyl)oxy]phenyl}-propanoate (570 mg, 2.0 mmol), acetic acid (0.1 mL) and 1,2-dichloroethane (5 mL) was added sodium triacetoxyborohydride (1.2 g, 5.7 mmol) under ice-cooling. The mixture was allowed to warm to room temperature and stirred for 1 hr. Phenylacetoaldehyde (35-50% diethyl phthalate solution, 480 mg) was added to the reaction mixture, and the mixture was further stirred at room temperature for 1 hr. The reaction mixture was poured into water and extracted with ethyl acetate. The organic layer was washed with saturated brine, dried over anhydrous magnesium sulfate, and concentrated. The residue was purified by silica gel column chromatography (ethyl acetate:hexane=1:19-1:2 in volume ratio) to give a yellow oil. To a mixture of the oil, ethanol (5 mL) and tetrahydrofuran (5 mL) was added 2N aqueous sodium hydroxide solution (2 mL), and the mixture was stirred at room temperature for 14 hr. The reaction mixture was diluted with water, neutralized with 10% aqueous citric acid solution, and extracted with ethyl acetate. The organic layer was concentrated and the residue was purified by silica gel column chromatography (ethyl acetate:hexane=1:4-4:1 in volume ratio) to give the title compound (267 mg, yield 24%) as a yellow oil.

MS: m/z 549 (M+H).

Example 50 ethyl 2-fluoro-3-{4-[(4-([(2-phenylethyl)(4-phenyl-1,3-thiazol-2-yl)amino]methyl)benzyl)oxy]phenyl}propanoate

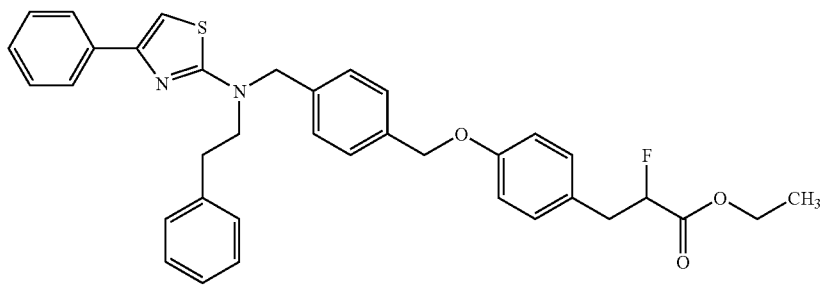

To a solution of [4-[[(2-phenylethyl)(4-phenyl-1,3-thiazol-2-yl)amino]methyl]phenyl]methanol (725 mg, 1.81 mmol), ethyl 2-fluoro-3-(4-hydroxyphenyl)propanoate (300 mg, 1.81 mmol) and tributylphosphine (550 mg, 2.72 mmol) in tetrahydrofuran (30 mL) was added 1,1'-(azodicarbonyl)-dipiperidine (685 mg, 2.72 mmol), and the mixture was stirred at room temperature for 16 hr. The insoluble materials were filtered off and the filtrate was concentrated, and the residue was purified by silica gel column chromatography (ethyl acetate:hexane=3:97-40:60) to give the title compound (798 mg, yield 78%, 2 steps) as a colorless oil.

MS: m/z 595 (M+H). $^1$H NMR (CDCl$_3$) δ 1.21-1.30(3H, m), 2.95-3.03(2H, m), 3.04-3.25(2H, m), 3.64-3.71(2H, m), 4.21(2H, q, J=7.1 Hz), 4.66(2H, s), 4.91-5.14(3H, m), 6.74 (1H, s), 6.86-6.94(2H, m), 7.12-7.42(14H, m), 7.85-7.91(2H, m).

Example 51

2-fluoro-3-{4-[(4-{[(2-phenylethyl)(4-phenyl-1,3-thiazol-2-yl)amino]methyl}benzyl)oxy]phenyl}propanoic acid

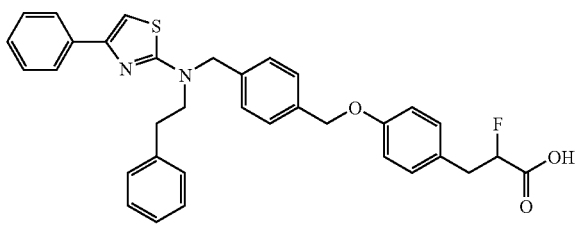

A mixture of ethyl 2-fluoro-3-{4-[(4-{[(2-phenylethyl)(4-phenyl-1,3-thiazol-2-yl)amino]methyl}benzyl)oxy]phenyl}-propanoate (740 mg, 1.31 mmol), tetrahydrofuran (15 mL), methanol (10 mL), water (10 mL) and lithium hydroxide monohydrate (165 mg, 3.92 mmol) was stirred at room temperature for 3 hr. The reaction mixture was neutralized with 1N hydrochloric acid and extracted with ethyl acetate. The organic layer was washed with saturated brine and dried over anhydrous magnesium sulfate. The solvent was evaporated under reduced pressure. The residue was recrystallized from hexane-diisopropyl ether to give the title compound (505 mg, yield 68%) as colorless crystals.

MS: m/z 567 (M+H). $^1$H NMR (CDCl$_3$) δ 2.95-3.03(2H, m), 3.03-3.31(2H, m), 3.63-3.72(2H, m), 4.65(2H, s), 4.98-5.20(3H, m), 6.73(1H, s), 6.90(2H, d, J=8.5 Hz), 7.12-7.43 (14H, m), 7.85-7.90(2H, m).

Example 52 ethyl 2,2-difluoro-3-{4-[(4-{[(2-phenylethyl)(4-phenyl-1,3-thiazol-2-yl)amino]methyl}benzyl)oxy]phenyl}-propanoate

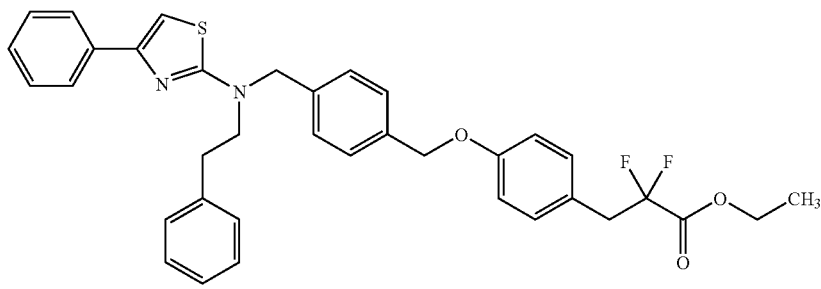

The title compound was obtained as a colorless oil in the same manner as in Example 31 from ethyl 2,2-difluoro-3-(4-hydroxyphenyl)propanoate and [4-[[(2-phenylethyl)(4-phenyl-1,3-thiazol-2-yl)amino]methyl]phenyl]methanol (yield 98%).
MS: m/z 613 (M+H).

Example 53

2,2-difluoro-3-{4-[(4-{[(2-phenylethyl)(4-phenyl-1,3-thiazol-2-yl)amino]methyl}benzyl)oxy]phenyl}propanoic acid

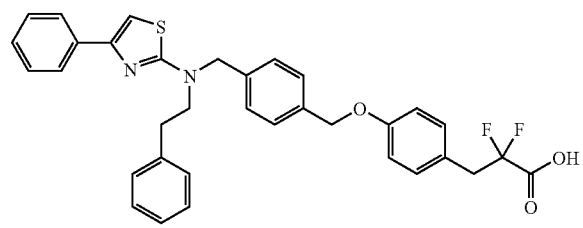

The title compound was obtained as a pale-blue oil in the same manner as in Example 32 from ethyl 2,2-difluoro-3-{4-[(4-{[(2-phenylethyl)(4-phenyl-1,3-thiazol-2-yl)amino]methyl}benzyl)oxy]phenyl}propanoate (yield 67%).
MS: m/z 585 (M+H).

Example 54 methyl 3-{4-[(6-{[(2-phenylethyl)(4-phenyl-1,3-thiazol-2-yl)amino]methyl}pyridin-3-yl)methoxy]phenyl}-propanoate

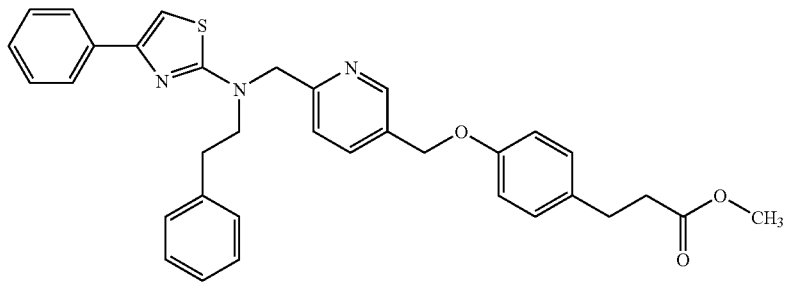

The title compound was obtained as a colorless oil in the same manner as in Example 31 from methyl 3-(4-hydroxyphenyl)propanoate and (6-{[(2-phenylethyl)(4-phenyl-1,3-thiazol-2-yl)amino]methyl}pyridin-3-yl)methanol (yield 70%).
MS: m/z 564 (M+H).

Example 55

3-{4-[(6-{[(2-phenylethyl)(4-phenyl-1,3-thiazol-2-yl)amino]methyl}pyridin-3-yl)methoxy]phenyl}propanoic acid

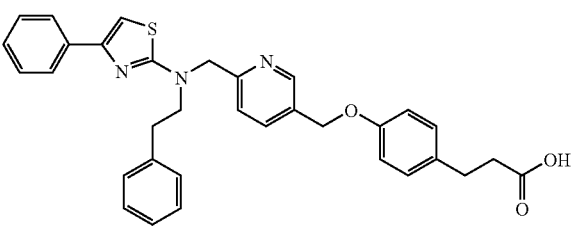

The title compound was obtained as colorless crystals in the same manner as in Example 32 from methyl 3-{4-[(6-{[(2-phenylethyl)(4-phenyl-1,3-thiazol-2-yl)amino]methyl}pyridin-3-yl)methoxy]phenyl}propanoate (yield 63%).
MS: m/z 550 (M+H).

Example 56 ethyl 3-{2-fluoro-4-[(4-{1-[(4-phenyl-1,3-thiazol-2-yl)sulfonyl]butyl}benzyl)oxy]phenyl}propanoate

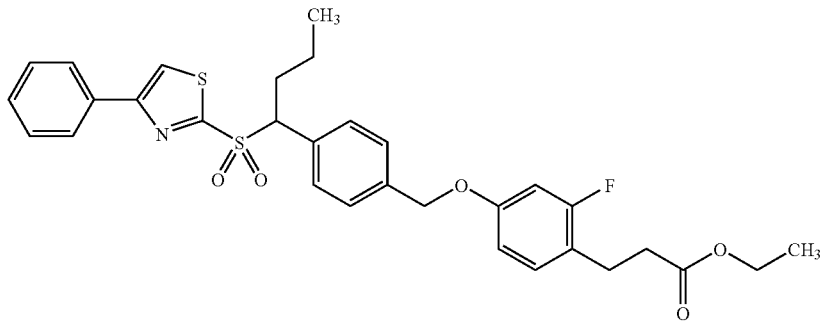

To a solution of ethyl 3-{2-fluoro-4-[(4-{1-[(4-phenyl-1,3-thiazol-2-yl)thio]butyl}benzyl)oxy]phenyl}propanoate (0.392 g, 0.713 mmol) in ethyl acetate (5 mL) was added m-chloroperbenzoic acid (72%, 0.513 g, 2.14 mmol), and the mixture was stirred at room temperature for 22 hr. The reaction mixture was washed with 1N aqueous sodium hydroxide solution and extracted with ethyl acetate. The extract was washed with saturated brine, dried over anhydrous magnesium sulfate, and concentrated under reduced pressure. The residue was purified by silica gel column chromatography (ethyl acetate:hexane=10:90-40:60) to give the title compound (0.397 g, yield 96%) as a pale-yellow oil.

MS: m/z 582 (M+H). $^1$H NMR (CDCl$_3$) δ 0.92(3H, t, J=7.3 Hz), 1.19-1.42(5H, m), 2.22-2.50(2H, m), 2.58(2H, t, J=7.5 Hz), 2.90(2H, t, J=7.5 Hz), 4.11(2H, q, J=7.1 Hz), 4.65(1H, dd, J=11.3,4.0 Hz), 4.97(2H, s), 6.58(1H, dd, J=11.9,2.5 Hz), 6.64(1H, dd, J=8.4,2.5 Hz), 7.10(1H, t, J=8.7 Hz), 7.22-7.32 (4H, m), 7.38-7.51(3H, m), 7.65(1H, s), 7.87-7.93(2H, m).

Example 57

3-{2-fluoro-4-[(4-{1-[(4-phenyl-1,3-thiazol-2-yl)sulfonyl]butyl}benzyl)oxy]phenyl}propanoic acid

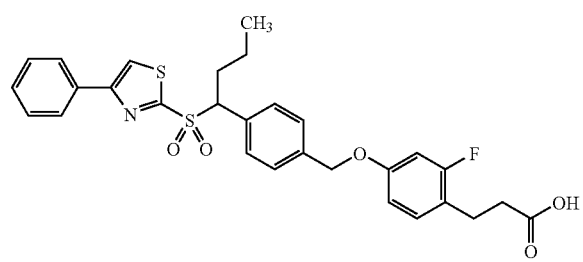

To a solution of ethyl 3-{2-fluoro-4-[(4-{1-[(4-phenyl-1,3-thiazol-2-yl)sulfonyl]butyl}benzyl)oxy]phenyl}propanoate (0.360 g, 0.619 mmol) in a mixture of ethanol (1.5 mL) and tetrahydrofuran (3 mL) was added 1N aqueous sodium hydroxide solution (0.75 mL), and the mixture was stirred at 50° C. for 1.5 hr. Water was added to the reaction mixture, and the mixture was weak acidified with 10% aqueous citric acid solution and extracted with ethyl acetate. The extract was washed with saturated brine, dried over anhydrous magnesium sulfate, and concentrated under reduced pressure. The residue was purified by silica gel column chromatography (ethyl acetate:hexane=30:70-80:20) and recrystallized from ethyl acetate-hexane to give the title compound (0.300 g, yield 88%) as colorless crystals.

MS: m/z 554 (M+H). $^1$H NMR (CDCl$_3$) δ 0.92(3H, t, J=7.3 Hz), 1.21-1.42(2H, m), 2.22-2.50(2H, m), 2.65(2H, t, J=7.5 Hz), 2.91(2H, t, J=7.5 Hz), 4.65(1H, dd, J=11.4,4.1 Hz), 4.97(2H, s), 6.59(1H, dd, J=11.9,2.4 Hz), 6.65(1H, dd, J=8.4, 2.5 Hz), 7.10(1H, t, J=8.7 Hz), 7.22-7.32(4H, m), 7.38-7.51 (3H, m), 7.65(1H, s), 7.87-7.93(2H, m).

Formulation Example 1

(Production of Capsule)

| | |
|---|---|
| 1) compound of Example 1 | 30 mg |
| 2) microcrystalline cellulose | 10 mg |
| 3) lactose | 19 mg |
| 4) magnesium stearate | 1 mg |
| total | 60 mg |

The above-mentioned 1), 2), 3) and 4) are mixed and filled in a gelatin capsule.

Formulation Example 2

(Production of Tablet)

| | |
|---|---|
| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

Experimental Example 1

Determination of $EC_{50}$ of the Compound of the Present Invention Against Human GPR40

For determination of $EC_{50}$, CHO cell line that stably expressed human GPR40 was used. Unless otherwise indicated, the CHO cell line was cultured using α-MEM medium (Invitrogen) containing 10% fetal calf serum (Invitrogen).

The cells cultured to nearly confluent were rinsed with PBS (Invitrogen) on the previous day of the assay, peeled off with 0.05% Trypsin-EDTA solution (Invitrogen) and recovered by centrifugation. The number of the obtained cells was counted, and the cells were diluted such that $3\times10^5$ cells were contained per 1 mL of the medium, dispensed to a black welled 96-well plate (coster) by 100 μL per well and cultured overnight in a $CO_2$ incubator. Various test compounds were added to the CHO cells thus prepared, and the changes in the intracellular calcium concentration was measured using FLIPR (Molecular Device). The below-mentioned pre-treatment was applied to measure changes in the intracellular calcium concentration by FLIPR.

An assay buffer for adding a fluorescent dye Fluo3-AM (DOJIN) to the cells, or for washing the cells immediately before FLIPR assay was prepared. To a solution of 1M HEPES (pH 7.4, DOJIN, 20 mL) added to HBSS (Invitrogen, 1000 mL) (hereinafter HBSS/HEPES solution) was added a solution (10 mL) obtained by dissolving probenecid (Sigma, 710 mg) in 1N NaOH (5 mL), and adding and mixing an HBSS/HEPES solution (5 mL), and the resulting solution was used as an assay buffer. Fluo3-AM (50 μg) was dissolved in dimethylsulfoxide (Wako, 21 μL), and an equivalent amount of 20% pluronic acid (Molecular Probes) was added and mixed. The solution was added to the assay buffer (10.6 mL) supplemented with fetal calf serum (105 μL) to give a fluorescent dye solution. On the previous day of assay, the medium of the CHO cells newly inoculated to the black welled 96-well plate was removed, the fluorescent dye solution was immediately dispensed by 100 μL per well and the cells were cultured in a $CO_2$ incubator for 1 hr to allow intake of the fluorescent dye by the cells. The cells after the culture were washed with the above-mentioned assay buffer and set on FLIPR. The test compound was diluted with dimethylsulfoxide in advance, dispensed to polypropylene 96-well plate (sample plate) by 2 μL, and cryopreserved at −20° C. To the thawed sample plate was added an assay buffer containing 0.015% CHAPS (DOJIN) by 198 μL, and simultaneously set on FLIPR together with the cell plate. After the aforementioned pre-treatment, changes in the intracellular calcium concentration upon addition of various test compounds was measured by FLIPR. Based on the results, a dose-response curve of each test compound was formed and $EC_{50}$ was calculated. The results are shown in Table 1.

TABLE 1

| Compound No. | $EC_{50}$ (nM) |
|---|---|
| Example 2 | 48 |
| Example 9 | 38 |
| Example 12 | 19 |
| Example 40 | 55 |
| Example 42 | 65 |

INDUSTRIAL APPLICABILITY

The compound (I) of the present invention, a salt thereof and a prodrug thereof have a superior GPR40 receptor function modulating action and can be used as an agent for the prophylaxis or treatment of diabetes and the like.

This application is based on patent application No. 2003-435089 filed in Japan, the contents of which are hereby incorporated by reference.

The invention claimed is:

1. A compound represented by the formula (I)

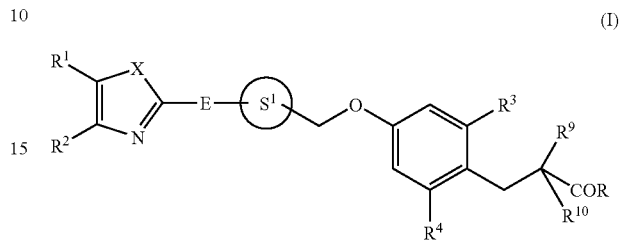

wherein X is S or O,
R$^1$ and R$^2$ are the same or different and each is a hydrogen atom, an optionally substituted $C_{6-14}$ aryl group, an optionally substituted heterocyclic group or an optionally substituted $C_{1-6}$ alkyl group, or R$^1$ and R$^2$ are bonded to each other to form a ring together with the carbon atom they are bonded to,
E is —W$^1$—N(R$^5$)—W$^2$—, —W$^1$—CH(R$^6$)—O—W$^2$—, —W$^1$—O—CH(R$^6$)—W$^2$—, —W$^1$—S(O)n-W$^2$— or —W$^1$—CH(R$^6$)—W$^2$— (W$^1$ and W$^2$ are the same or different and each is a bond or an optionally substituted $C_{1-3}$ alkylene group, R$^5$ and R$^6$ are each an optionally substituted heterocyclic group or an optionally substituted hydrocarbon group, and n is 1 or 2, provided that when X is S, then R$^5$ and R$^6$ are not $C_{1-6}$ alkyl groups),
ring S$^1$ is a benzene ring or pyridine ring each optionally further having substituent(s) selected from an optionally substituted $C_{1-6}$ alkyl group, an optionally substituted $C_{1-6}$ alkoxy group and a halogen atom,
R$^3$ and R$^4$ are the same or different and each is a hydrogen atom, a halogen atom, an optionally substituted $C_{1-6}$ alkyl group or an optionally substituted $C_{1-6}$ alkoxy group,
R$^9$ and R$^{10}$ are the same or different and each is a hydrogen atom, a halogen atom or a $C_{1-6}$ alkoxy group, and
R is an optionally substituted hydroxy group or an optionally substituted amino group, or a prodrug or a salt thereof.

2. The compound of claim 1, wherein E is —W$^1$—N(R$^5$)—W$^2$—, —W$^1$—CH(R$^6$)—O—W$^2$—, —W$^1$—O—CH(R$^6$)—W$^2$— or —W$^1$—CH(R$^6$)—W$^2$— (W$^1$ and W$^2$ are the same or different and each is a bond or an optionally substituted $C_{1-3}$ alkylene group, and R$^5$ and R$^6$ are each an optionally substituted heterocyclic group or an optionally substituted hydrocarbon group, provided that when X is S, then R$^5$ and R$^6$ are not $C_{1-6}$ alkyl groups),
ring S$^1$ is a benzene ring optionally further having substituent(s) selected from an optionally substituted $C_{1-6}$ alkyl group, an optionally substituted $C_{1-6}$ alkoxy group and a halogen atom, and
R$^9$ and R$^{10}$ are hydrogen atoms,
or a salt thereof.

3. The compound of claim 1, wherein R$^3$ and R$^4$ are the same or different and each is a hydrogen atom or a halogen atom, or a salt thereof.

4. The compound of claim 1, wherein E is —W$^1$—N(R$^5$)—W$^2$— (W$^1$ and W$^2$ are the same or different and each is a bond or an optionally substituted $C_{1-3}$ alkylene group, and $R^5$ is an optionally substituted heterocyclic group or an optionally substituted hydrocarbon group, provided that when X is S, then $R^5$ is not a $C_{1-6}$ alkyl group), or a salt thereof.

5. The compound of claim 4, wherein $R^5$ is an optionally substituted $C_{7-16}$ aralkyl group, or a salt thereof.

6. The compound of claim 1, wherein R is a hydroxy group, or a salt thereof.

7. The compound of claim 1, wherein X is S, or a salt thereof.

8. The compound of claim 1, wherein ring $S^1$ is a benzene ring, or a salt thereof.

9. The compound of claim 1, wherein both $R^9$ and $R^{10}$ are hydrogen atoms, or a salt thereof.

10. 3-[4-[[4-[[(2-Phenylethyl)(4-phenyl-1,3-thiazol-2-yl) amino]methyl]benzyl]oxy]phenyl]propanoic acid, 3-[2,6-difluoro-4-[[4-[[(2-phenylethyl)(4-phenyl-1,3-thiazol-2-yl) amino]methyl]benzyl]oxy]phenyl]propanoic acid, 2-fluoro-3-{4-[(4-{[(2-phenylethyl)(4-phenyl-1,3-thiazol-2-yl) amino]methyl}benzyl)oxy]phenyl}propanoic acid, 3-{2-fluoro-4-[(4-{1-[(4-phenyl-1,3-thiazol-2-yl)sulfonyl] butyl}benzyl)oxy]phenyl}propanoic acid, or a salt thereof.

11. A pharmaceutical comprising a compound of claim 1 or a salt thereof or a prodrug thereof, together with a pharmaceutically acceptable carrier.

12. A method for activating GPR40 receptor function in a mammal, for treating type II diabetes, obesity, insulin resistance or impaired glucose tolerance, which comprises administering an effective amount of a compound of claim 1 or a salt thereof or a prodrug thereof to the mammal.

13. A method for the treatment of diabetes in a mammal, which comprises administering an effective amount of a compound of claim 1 or a salt thereof or a prodrug thereof to the mammal.

* * * * *